(12) United States Patent
Kornete et al.

(10) Patent No.: US 12,365,922 B2
(45) Date of Patent: *Jul. 22, 2025

(54) ALLELE EDITING AND APPLICATIONS THEREOF

(71) Applicant: UNIVERSITÄT BASEL, Basel (CH)

(72) Inventors: Mara Kornete, Basel (CH); Lukas Jeker, Riehen (CH)

(73) Assignee: UNIVERSITÄT BASEL, Basel (CH)

( * ) Notice: Subject to any disclaimer, the term of this patent is extended or adjusted under 35 U.S.C. 154(b) by 368 days.

This patent is subject to a terminal disclaimer.

(21) Appl. No.: 17/948,313

(22) Filed: Sep. 20, 2022

(65) Prior Publication Data

US 2023/0193320 A1 Jun. 22, 2023

Related U.S. Application Data

(63) Continuation of application No. 16/096,074, filed as application No. PCT/EP2017/059799 on Apr. 25, 2017, now Pat. No. 11,499,168.

(30) Foreign Application Priority Data

| Apr. 25, 2016 | (EP) | 16166854 |
| Apr. 25, 2016 | (EP) | 16166856 |
| Apr. 25, 2016 | (EP) | 16166857 |
| Nov. 2, 2016 | (EP) | 16196856 |
| Nov. 2, 2016 | (EP) | 16196858 |
| Nov. 2, 2016 | (EP) | 16196860 |

(51) Int. Cl.
| *A61K 35/28* | (2015.01) |
| *A61K 35/17* | (2015.01) |
| *A61P 35/00* | (2006.01) |
| *C12N 5/0783* | (2010.01) |
| *C12N 5/0789* | (2010.01) |
| *C12N 15/10* | (2006.01) |
| *C12N 15/90* | (2006.01) |

(52) U.S. Cl.
CPC ............ *C12N 15/902* (2013.01); *A61K 35/17* (2013.01); *A61K 35/28* (2013.01); *A61P 35/00* (2018.01); *C12N 5/0636* (2013.01); *C12N 5/0647* (2013.01); *C12N 15/102* (2013.01)

(58) Field of Classification Search
None
See application file for complete search history.

(56) References Cited

FOREIGN PATENT DOCUMENTS

| CN | 102271711 A | 12/2011 |
| TW | 201614072 A | 4/2016 |
| WO | 2010067671 A1 | 6/2010 |

*Primary Examiner* — Michail A Belyavskyi
(74) *Attorney, Agent, or Firm* — WCF IP

(57) ABSTRACT

The invention relates to a method to determine a homology directed repair (HDR) event within a eukaryotic cell, wherein the cell expresses a first isoform of a surface protein, which is different from a second isoform of said surface protein with regard to an amino acid marker. The method comprises the steps of inducing a DNA double strand break, providing a HDR template DNA construct comprising the amino acid marker corresponding to the second isoform of the surface protein and subsequently determining the expression of the first or second isoform of said surface protein on said cell, wherein expression of the second isoform indicates a successful HDR event. The invention also relates to a method for editing a genomic location of interest within a eukaryotic cell, and to a method of selectively depleting or enriching an edited cell in a composition of non-edited and edited cells.

7 Claims, 34 Drawing Sheets

Specification includes a Sequence Listing.

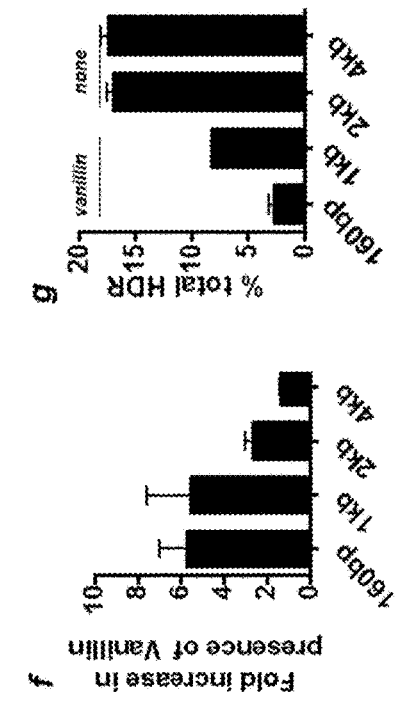
Fig. 2E
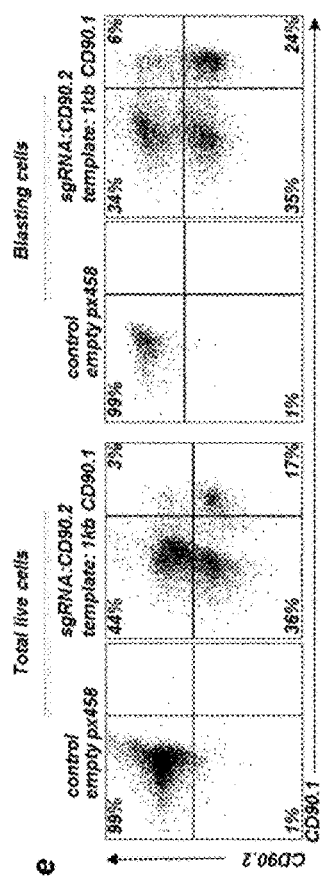
Fig. 2F
Fig. 2G
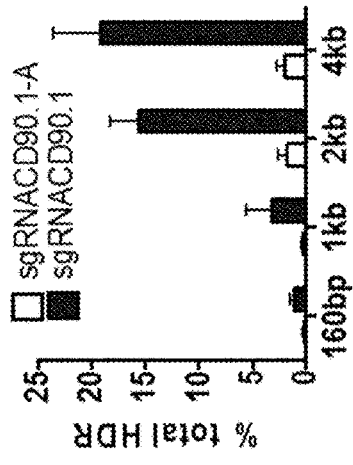
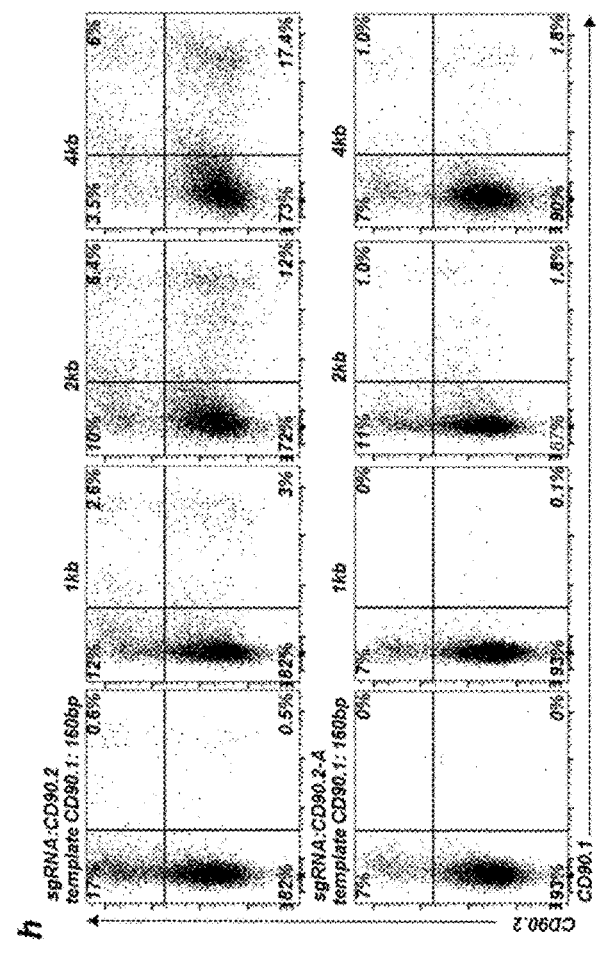
Fig. 2H

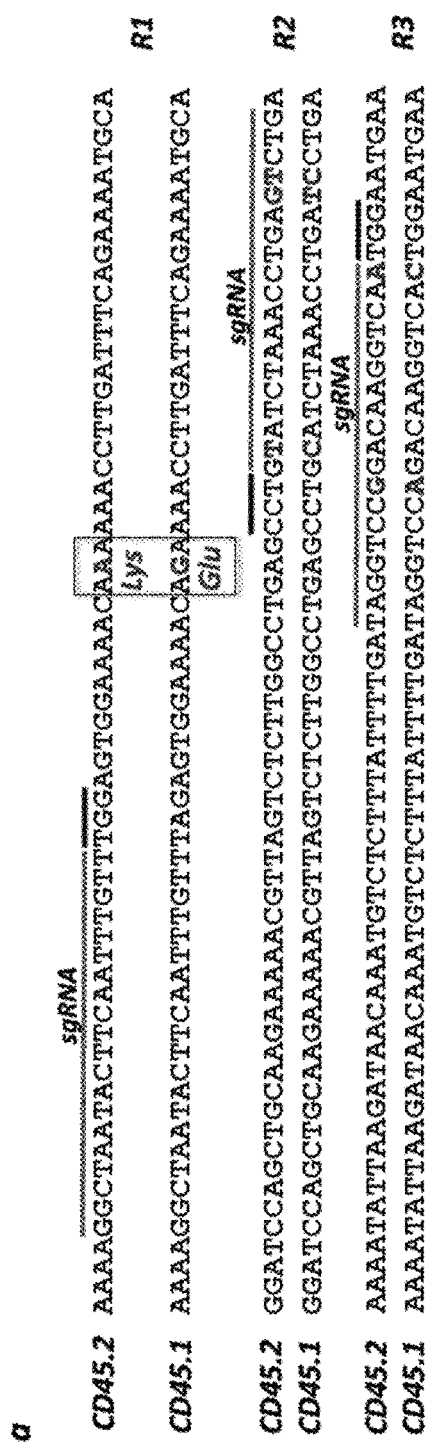
Fig. 3A
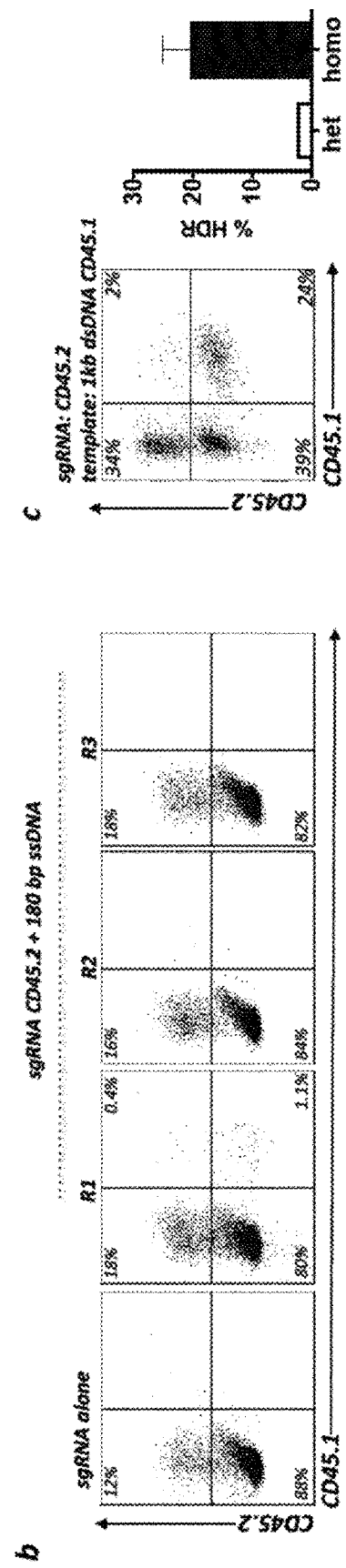
Fig. 3B
Fig. 3C

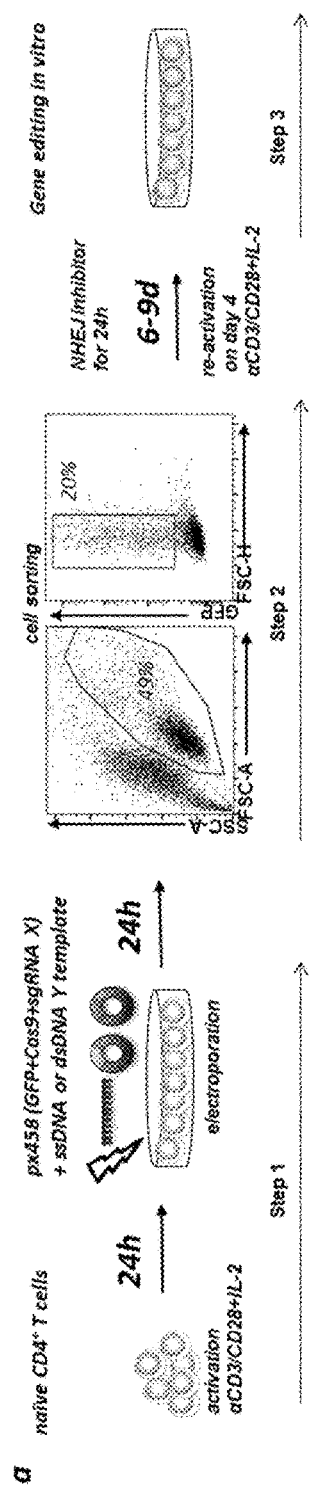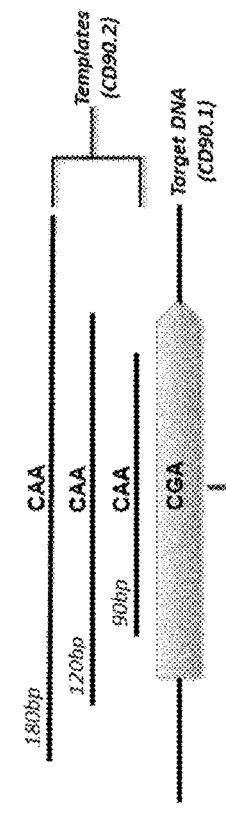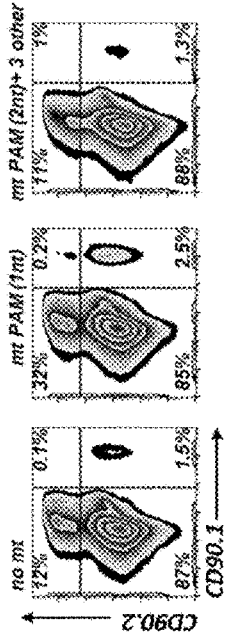
Fig. 5A
Fig. 5B
Fig. 5C
Fig. 5D

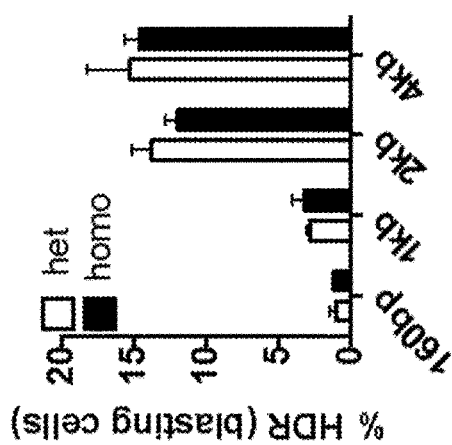
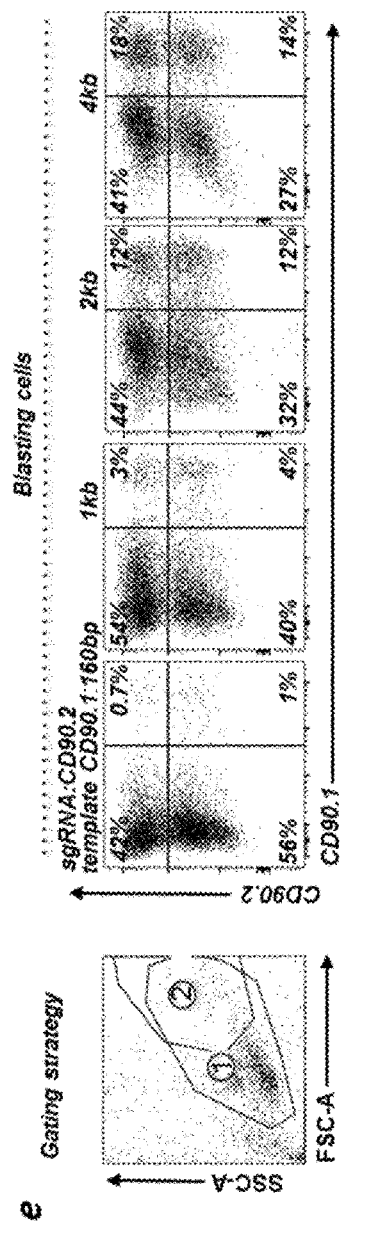
Fig. 5E
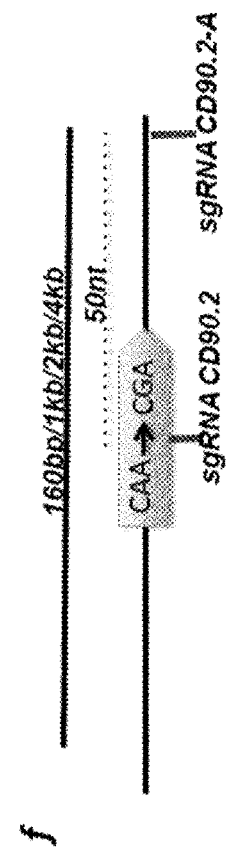
Fig. 5F

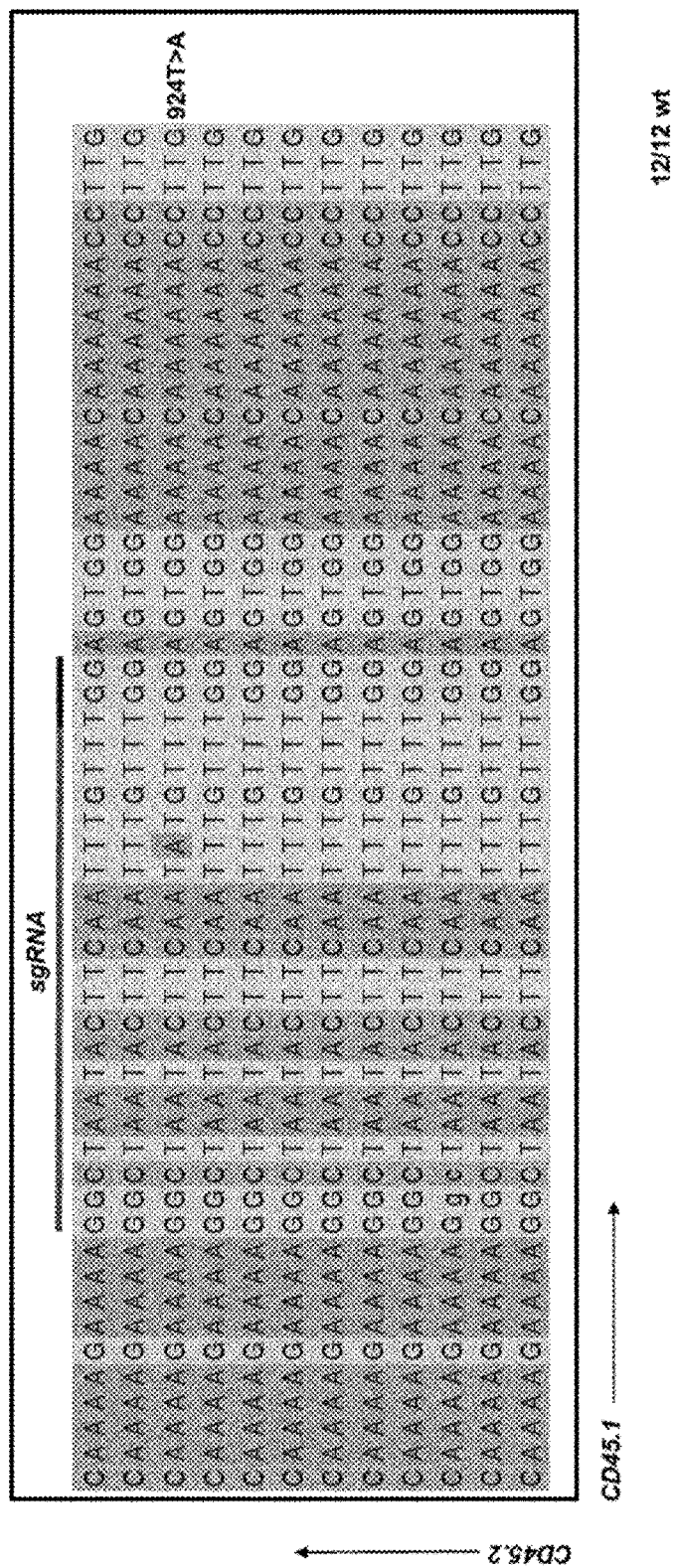
Fig. 6A-Q1

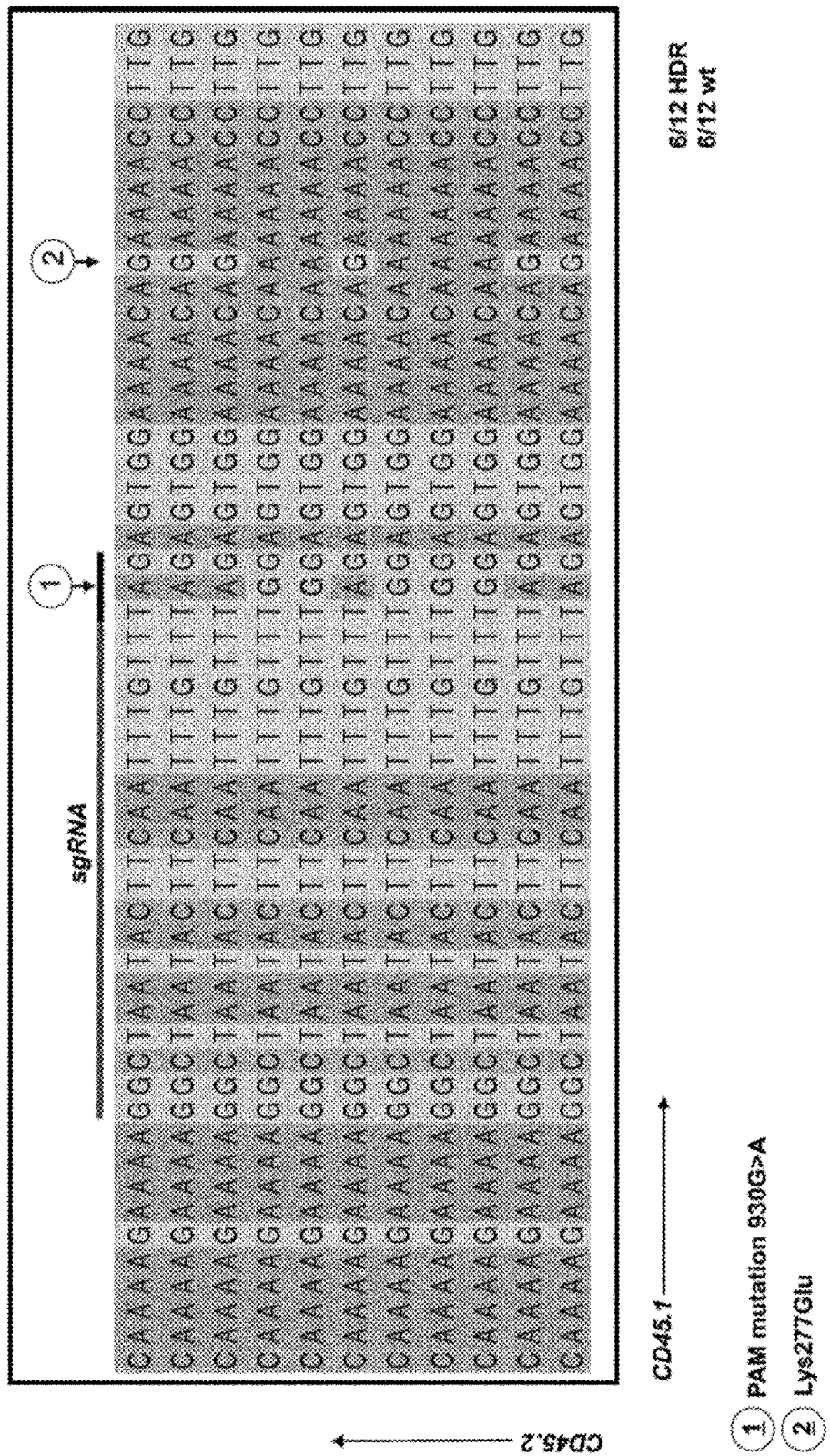
Fig. 6A-Q2

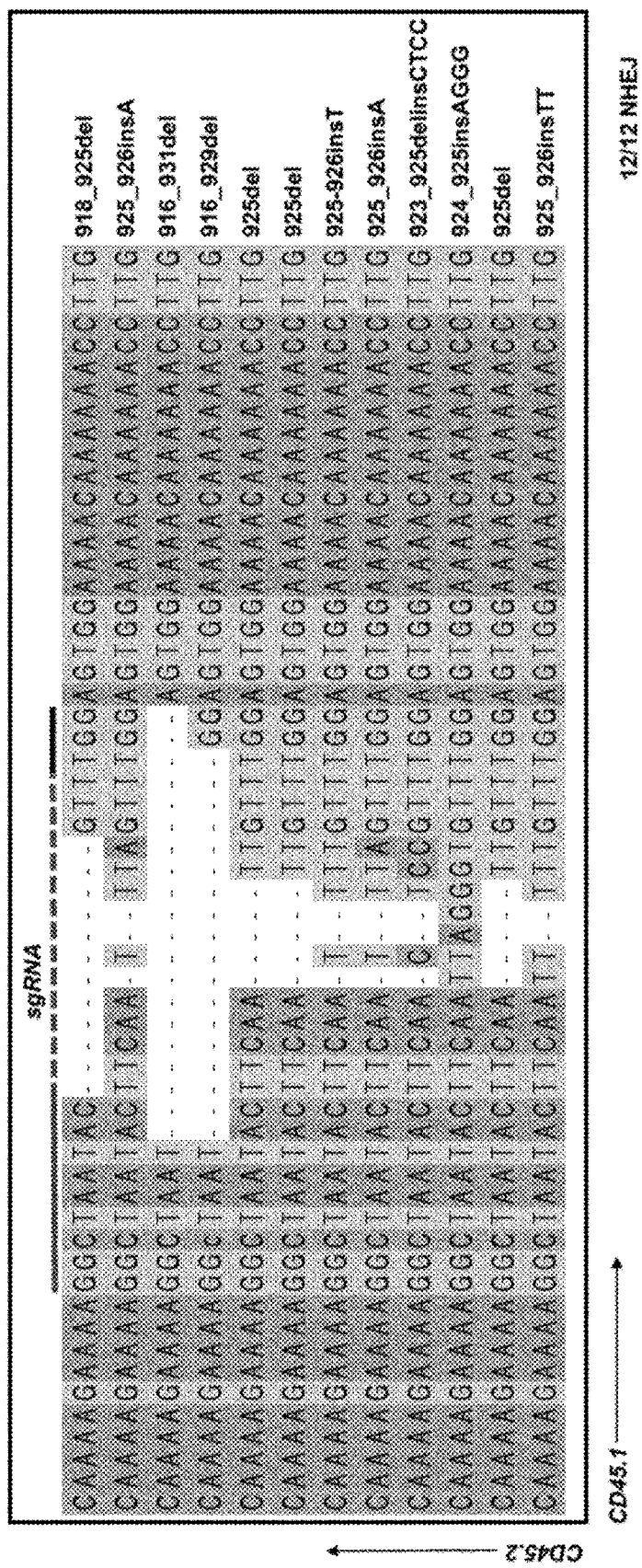
Fig. 6A-Q3

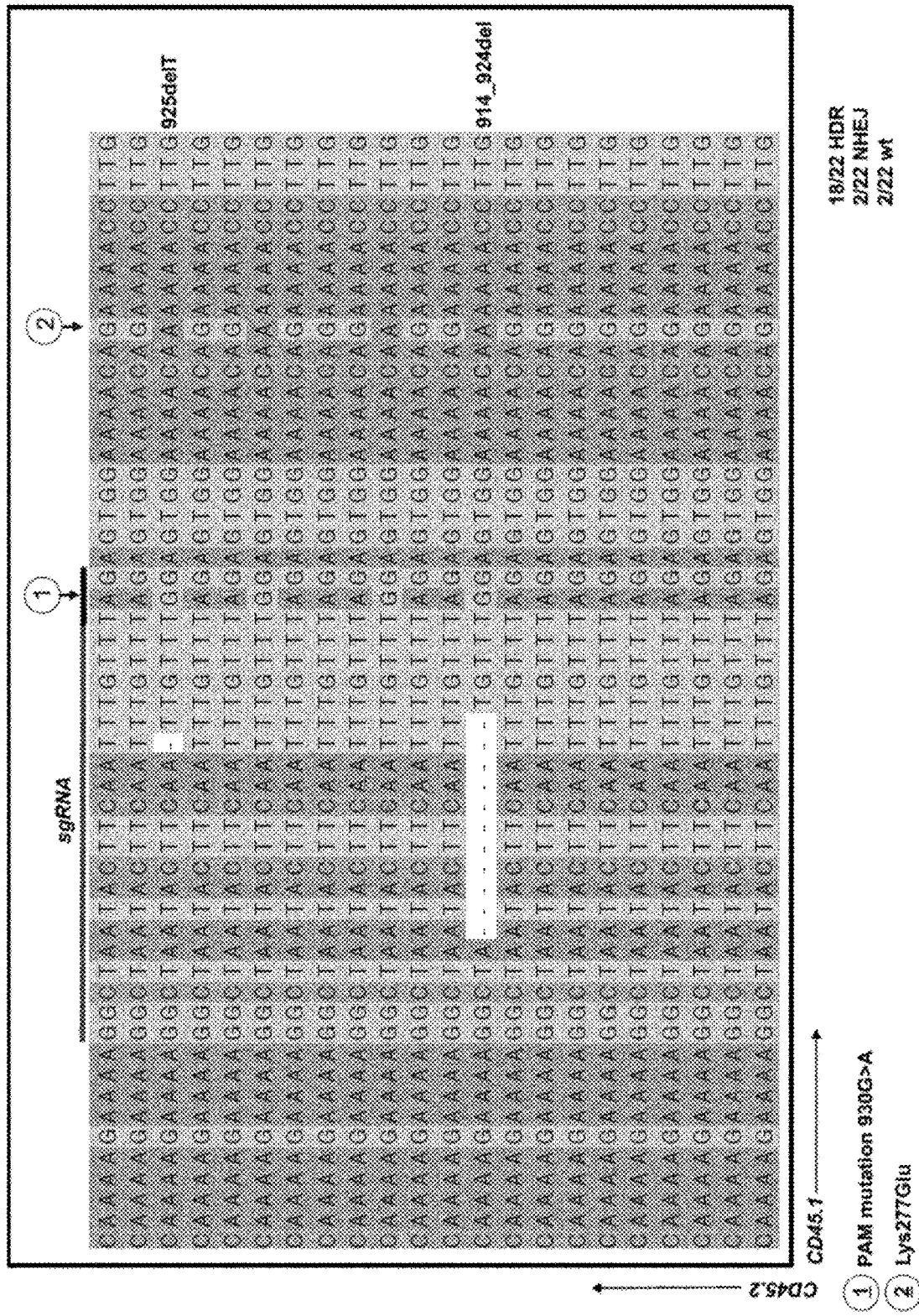
Fig. 6A-Q4

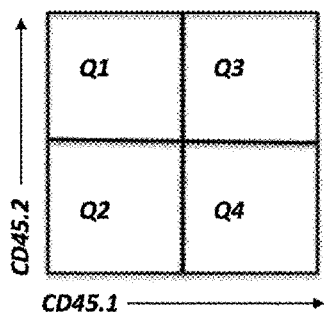 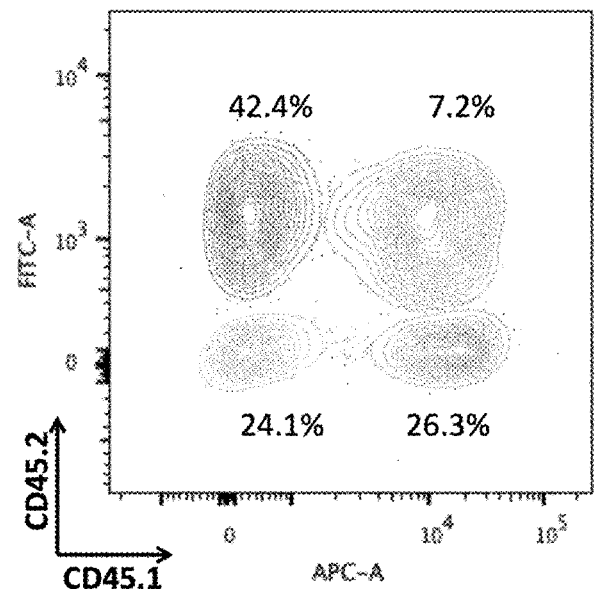
Fig. 6B
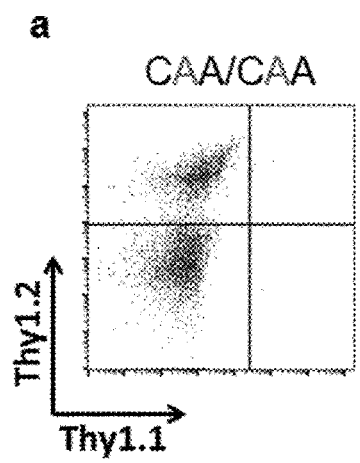 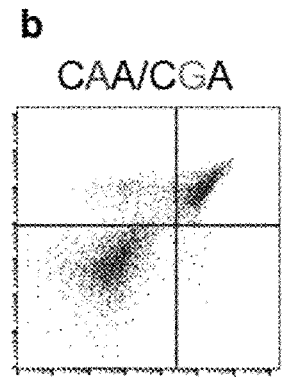 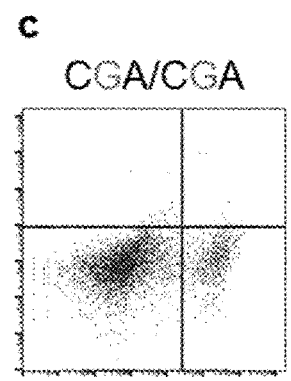
Fig. 7A      Fig. 7B      Fig. 7C

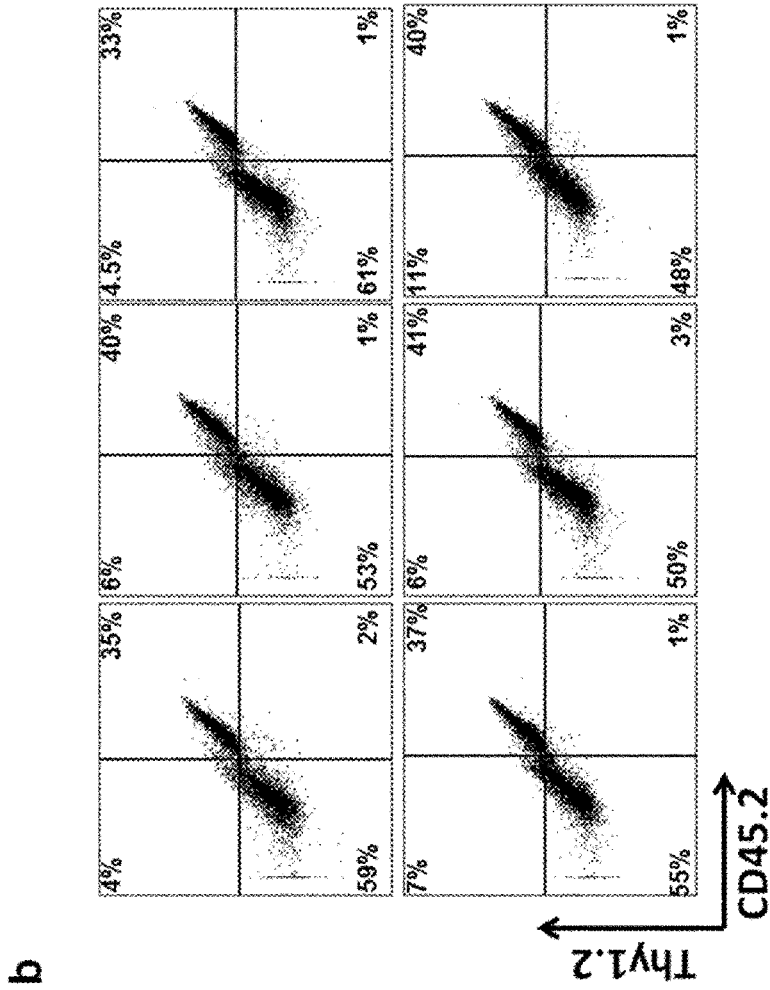
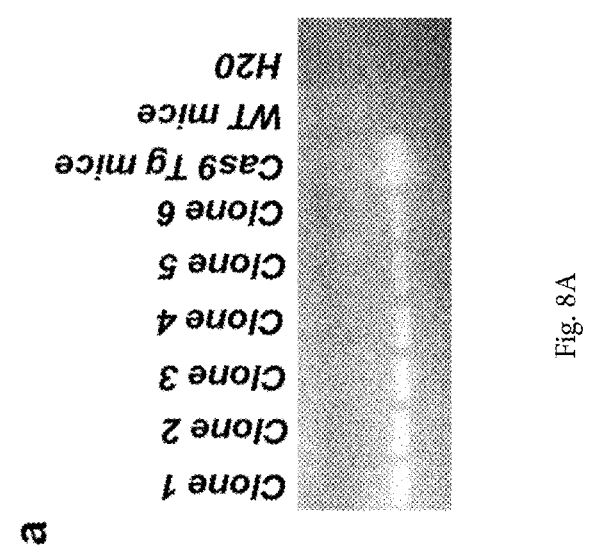
Fig. 8A
Fig. 8B

```
                           SEQUENCE LISTING

Sequence total quantity: 61
SEQ ID NO: 1             moltype = DNA  length = 20
FEATURE                  Location/Qualifiers
misc_feature             1..20
                         note = Synthetic guide RNA
source                   1..20
                         mol_type = other DNA
                         organism = synthetic construct
SEQUENCE: 1
gttttgtgag cttcaagtct                                                  20

SEQ ID NO: 2             moltype = DNA  length = 20
FEATURE                  Location/Qualifiers
misc_feature             1..20
                         note = Synthetic guide RNA
source                   1..20
                         mol_type = other DNA
                         organism = synthetic construct
SEQUENCE: 2
gaaagtatca gtgtgtatag                                                  20

SEQ ID NO: 3             moltype = DNA  length = 20
FEATURE                  Location/Qualifiers
misc_feature             1..20
                         note = Synthetic guide RNA
source                   1..20
                         mol_type = other DNA
                         organism = synthetic construct
SEQUENCE: 3
ggctaatact tcaatttgtt                                                  20

SEQ ID NO: 4             moltype = DNA  length = 20
FEATURE                  Location/Qualifiers
misc_feature             1..20
                         note = Synthetic guide RNA
source                   1..20
                         mol_type = other DNA
                         organism = synthetic construct
SEQUENCE: 4
gcagactcag gtttagatac                                                  20

SEQ ID NO: 5             moltype = DNA  length = 20
FEATURE                  Location/Qualifiers
misc_feature             1..20
                         note = Synthetic guide RNA
source                   1..20
                         mol_type = other DNA
                         organism = synthetic construct
SEQUENCE: 5
gtaggtccgg acaaggtcaa                                                  20

SEQ ID NO: 6             moltype = DNA  length = 20
FEATURE                  Location/Qualifiers
```

```
misc_feature            1..20
                        note = Synthetic guide RNA
source                  1..20
                        mol_type = other DNA
                        organism = synthetic construct
SEQUENCE: 6
gcaagatatc tagtccattg                                                     20

SEQ ID NO: 7            moltype = DNA   length = 20
FEATURE                 Location/Qualifiers
misc_feature            1..20
                        note = Synthetic guide RNA
source                  1..20
                        mol_type = other DNA
                        organism = synthetic construct
SEQUENCE: 7
gagagctctt ttgtccattg                                                     20

SEQ ID NO: 8            moltype = DNA   length = 20
FEATURE                 Location/Qualifiers
misc_feature            1..20
                        note = Synthetic guide RNA
source                  1..20
                        mol_type = other DNA
                        organism = synthetic construct
SEQUENCE: 8
gtttgtgagc ttcgagtctc                                                     20

SEQ ID NO: 9            moltype = DNA   length = 180
FEATURE                 Location/Qualifiers
source                  1..180
                        mol_type = other DNA
                        organism = Mus musculus
SEQUENCE: 9
gtttcctcca cagggactga caagttttcg ctacatgact gcacaccaaa agaaaaggct         60
aatacttcaa tttgtttaga gtggaaaaca gaaaaccttg atttcagaaa atgcaacagt        120
gacaatattt catatgtact ccactgtgag ccaggtacga tgctgggcag agaagttcta        180

SEQ ID NO: 10           moltype = DNA   length = 180
FEATURE                 Location/Qualifiers
source                  1..180
                        mol_type = other DNA
                        organism = Mus musculus
SEQUENCE: 10
agttccagaa acgcctaagc ctagttgtgg ggatccagct gcaagaaaaa cgttagtctc         60
ttggcctgag cctgcatcta aacctgatcc tgcatctaaa ccccatggat atgttttatg        120
ctataagaac aattcaggta atgtaaaatt ccactaggga aacaaaatca agaattttta        180

SEQ ID NO: 11           moltype = DNA   length = 180
FEATURE                 Location/Qualifiers
source                  1..180
                        mol_type = other DNA
                        organism = Mus musculus
SEQUENCE: 11
ttacattgta ctcatgcttc aaggtattta aactttttaca tgtcaaaata ttaagataac        60
aaatgtctct ttattttgat aggtccagac aaggtcactg gaatgaaaac ctcccgccg         120
acagacaata gtataaatgt tacatgtggt cctccttatg aaactaatgg ccctaaaacc        180

SEQ ID NO: 12           moltype = DNA   length = 180
FEATURE                 Location/Qualifiers
source                  1..180
                        mol_type = other DNA
                        organism = Mus musculus
SEQUENCE: 12
caaactaatg tttgaaaggc tacaatgaaa tgacaagctt aagtgtctcg attaccacac         60
ccctcccaac cctcaggcg tcaatggaca agagctcttg ctgcatcgta gccaccagta        120
ctcagggcag tgtgctcccg gcctggtctg ctcctcggga ggctccagac ggcggcctgt        180

SEQ ID NO: 13           moltype = DNA   length = 180
FEATURE                 Location/Qualifiers
source                  1..180
                        mol_type = other DNA
                        organism = Mus musculus
SEQUENCE: 13
cgtcaccctc tccaaccagc cctatatcaa ggtccttacc ctagccaact tcaccaccaa         60
ggatgagggc gactactttt gtgagcttcg agtctcgggc gcgaatccca tgagctccaa        120
taaaagtatc agtgtgtata gaggtgagac tggttcccag aaagataaaa tgtccaggtt        180

SEQ ID NO: 14           moltype = DNA   length = 180
```

```
FEATURE                 Location/Qualifiers
source                  1..180
                        mol_type = other DNA
                        organism = Mus musculus
SEQUENCE: 14
cgtcaccctc tccaaccagc cctatatcaa ggtccttacc ctagccaact tcaccaccaa   60
ggatgagggc gactactttt gtgagcttcg agtctcaggc gcgaatccca tgagctccaa  120
taaaagtatc agtgtgtata gaggtgagac tggttcccag aaagataaaa tgtccaggtt  180

SEQ ID NO: 15           moltype = DNA   length = 180
FEATURE                 Location/Qualifiers
source                  1..180
                        mol_type = other DNA
                        organism = Mus musculus
SEQUENCE: 15
cgtcaccctc tccaaccagc cctatatcaa ggtccttacc ctagccaact tcaccaccaa   60
ggatgagggc gactactttt gtgagcttcg agtaagcgga gcgaatccca tgagctccaa  120
taaaagtatc agtgtgtata gaggtgagac tggttcccag aaagataaaa tgtccaggtt  180

SEQ ID NO: 16           moltype = DNA   length = 90
FEATURE                 Location/Qualifiers
source                  1..90
                        mol_type = other DNA
                        organism = Mus musculus
SEQUENCE: 16
acactgatac ttttattgga gctcatggga ttcgcgcccg agacttgaag ctcacaaaag   60
tagtcgccct catccttggt ggtgaagttg                                    90

SEQ ID NO: 17           moltype = DNA   length = 120
FEATURE                 Location/Qualifiers
source                  1..120
                        mol_type = other DNA
                        organism = Mus musculus
SEQUENCE: 17
agtttgtctc tatacacact gatactttta ttggagctca tgggattcgc gcccgagact   60
tgaagctcac aaaagtagtc gccctcatcc ttggtggtga agttggctag ggtaaggacc  120

SEQ ID NO: 18           moltype = DNA   length = 180
FEATURE                 Location/Qualifiers
source                  1..180
                        mol_type = other DNA
                        organism = Mus musculus
SEQUENCE: 18
accagcaggc ttatgccgcc acacttgacc agtttgtctc tatacacact gatactttta   60
ttggagctca tgggattcgc gcccgagact tgaagctcac aaaagtagtc gccctcatcc  120
ttggtggtga agttggctag ggtaaggacc ttgatatagg gctggttgga gagggtgacg  180

SEQ ID NO: 19           moltype = DNA   length = 1000
FEATURE                 Location/Qualifiers
source                  1..1000
                        mol_type = other DNA
                        organism = Mus musculus
SEQUENCE: 19
caaatgggaa aaatcagccg tttatcttga tgtttccttg agttgcattt ataaaagcag   60
cacacatttc tactgaaatc tgtggtacga agaaaaatatg ttatcttccc taatgaatgg  120
caaatatctg agttgataaa caaactgcca gcaagtggtg tctacacata tagatatatc  180
aaaacactaa taatgtgcac atatttgtat aattgtgcat cagctgaaat ggagataaat  240
taaaaattag gaatgtgact agatcatgaa gaagcatcag accttgggag agcttagatg  300
tcccctagcg aaatctcctg cttgcaagac tgtactccat gagtcttatt tcagagttga  360
gagggttcac atctccacac caggaaccat cacctaagag cacctctccg tttcctccac  420
agggactgac aagttttcgc tacatgactg cacaccaaaa gaaaaggcta atacttcaat  480
ttgtttagag tggaaaacag aaaaccttga tttcagaaaa tgcaacagtg acaatatttc  540
atatgtactc cactgtgagc caggtacgat gctgggcaga gaagttctat tatcagaaat  600
tattccagac gtggcttaaa tgttctttct gtagccttgt cctcctcacc caccctcagt  660
gatccgccat aaattagaat aaaataaccc tagtatctct ggcactgaaa caaattcaca  720
acgtagataa atgaaaagag caacccatgg atgataaata ttatgaaaaa ttaattaaaa  780
gaattttctt gagtactgtt atataccaga cattgttgaa agggtgatga gatgcaggca  840
ttataaaaga aagatggtat ccatagtctg tagaaaggaa gcatagtatt atccacaccg  900
gaggttgctt tctcagactt tcatacatga aaatcattgg aaagttcaag aatctgcagg  960
tagcaaggaa aacaagtgct tctaggaggg aacatgggtt                        1000

SEQ ID NO: 20           moltype = DNA   length = 1995
FEATURE                 Location/Qualifiers
source                  1..1995
                        mol_type = other DNA
                        organism = Mus musculus
SEQUENCE: 20
atggtttaca gagcaagttt caagacagcc caggatacac agagaaaccc tgtctcaaaa   60
caaacaaaac aaaacaaaaa gcaaaaaaca caaaactaaa acaacataac aacaaaccat  120
```

```
caaaaagcag ttcctatgga ttagaaacag cctattttgt attttgtgaa ataattatac    180
ataagattgc tgttttttca ttttttttctt tcttctttttt ggtatttctt tttaaattca    240
aaatgttctc attagagaaa agaatgtagt taaacatcta atgttttctg gaaaaaaaaa    300
tcaaggggga aattctagtt atgttaatac caaagttgtg atcacagcac gtggaaggca    360
ggagtacctt atgtgttcaa agccagtcta tgctgtatct tgaattctgt ggcagccttc    420
acagtgtgag attacacctt gtttccaaaa ccccaaacag atcaacaaca agcgtgaaaa    480
cagcaaagaa attgttttttc aaatgggaaa aatcagccgt ttatcttgat gtttccttga    540
gttgcattta taaaagcagc acacatttct actgaaatct gtggtacgaa gaaaatatgt    600
tatcttccct aatgaatggc aaatatctga gttgataaac aaactgccag caagtggtgt    660
ctacacatat agatatatca aaacactaat aatgtgcaca tatttgtata attgtgcatc    720
agctgaaatg gagataaatt aaaaattagg aatgtgacta gatcatgaag aagcatcaga    780
ccttgggaga gcttagatgt cccctagcga aatctcctgc ttgcaagact gtactccatg    840
agtcttattt cagagttgag agggttcaca tctccacacc aggaaccatc acctaagagc    900
acctctccgt ttcctccaca gggactgaca agttttcgct acatgactgc acaccaaaag    960
aaaaggctaa tacttcaatt tgtttagagt ggaaaacaga aaaccttgat ttcagaaaat   1020
gcaacagtga caatatttca tatgtactcc actgtgagcc aggtacgatg ctgggcagag   1080
aagttctatt atcagaaatt attccagacg tggcttaaat gttctttctg tagccttgtc   1140
ctcctcaccc accctcagtg atccgccata aattagaata aataaccct agtatctctg   1200
gcactgaaac aaaattcacaa cgtagataaa tgaaaagagc aacccatgga tgataaatat   1260
tatgaaaaat taattaaaag aattttcttg agtactgtta tataccagac attgttgaaa   1320
gggtgatgag atgcaggcat tataaagaa agatggtatc catagtctgt agaaaggaag   1380
catagtatta tccacaccgg aggttgcttt ctcagacttt catacatgaa aatcattgga   1440
aagttcaaga atctgcaggt agcaaggaaa acaagtgctt ctaggaggga acatgggttt   1500
ctctagaggt tggatctttt aaaacatata tttgaattca gtgaggtgga ctcttttctcc   1560
tctaggcata cagctatgtg ccaggacaca cttgacaaga cagagggagg tacatacacc   1620
cagagcggga agaggaaatt tcactctgat tgtaaacatt gtgctaacag gaaattgctg   1680
ggctaagata caaataggat gttcacagct ggaacaaata tatgttgagt taacattttt   1740
ttaaaaaatt ttaaataagt cacaatactg atttctcaac aaaattgagt atagcaatgt   1800
tatctgcagg atcttggttt attatttcac cattttcaga gacttgacct taacatgaag   1860
tcttaaacac atggtgccat aaaagaagcc catttactat gtggcatttc atatactcat   1920
gtgcaatact tacttcttc agaaaataat acaaaatgca ttagaagaaa tacattcata   1980
cctgaaagat gtcag                                                    1995

SEQ ID NO: 21        moltype = DNA   length = 4000
FEATURE              Location/Qualifiers
source               1..4000
                     mol_type = other DNA
                     organism = Mus musculus
SEQUENCE: 21
ttaattcacc aagtattatt gaattgttga taacagacag atatatcata aacccgagtt      60
aatgataatg aacaaaatag actagttatg gttctcatgg acttttcaat ttagttggaa    120
agatagatac caaaccaata attatcatag tataaactgg gatcttttat aggagaaagg    180
atttcaaaat aatgatgtag gggtacatga tacagttctt ctattttttca tattcctgca    240
gatactgtgc tacaacctac aatctgcttt ggtgatattt tggtatatta cctctgctat    300
atgctaatta ttcttttact tctgcttgct gagtactgaa tttgaaaccc aaaatacact    360
tatttcatca gatcattctc tgtacaaaag aatatgttaa gacatttgta tccaatgtag    420
tatcattcat tctcgatgat gattgtacta atttccttt tttttttttc cagctgccat    480
gtttgggaac attactgtga attacaccta tgaatctagt aatcagactt ttaaggcaga    540
cctcaaagat gtccaaaatg ctaagtgtgg aaatgaggat tgtgaaaacg tgttaaataa    600
tctagaagaa tgctcacaga taaaaaacat cagtgtgtct aatgactcat gtgctccagc    660
tacaactata gatttatatg taccaccagg tgaatgtcaa tttctctcta tctgggtatt    720
tagagcaaca gaaggatttc atgtatgtgt tcctgtgctt cttcaagcta atgtggtcag    780
aaaaaagaac cgagggaaag caagtgagct ttgataagag tgtgtttcct gctgagaacc    840
ccggagagca gagagaaata cacacttatt ccttaggacc accacctggc tctcttattt    900
ctttataaa gagattccca gctgggaagt ggtgtccctc accttcaatc tcagcacttc    960
agaggcagag gcaggcagat ctcgggttc caaggcagcc atggtttaca gagcaagttt   1020
caagacagcc caggatacac agagaaaccc tgtctcaaaa caaacaaaac aaaacaaaaa   1080
gcaaaaaaca caaactaaa acaacataac aacaaaccat caaaaagcag ttcctatgga   1140
ttagaaacag cctattttgt attttgtgaa ataattatac ataagattgc tgttttttca   1200
ttttttttctt tcttctttttt ggtatttctt tttaaattca aaatgttctc attagagaaa   1260
agaatgtagt taaacatcta atgttttctg gaaaaaaaaa tcaaggggga aattctagtt   1320
atgttaatac caaagttgtg atcacagcac gtggaaggca ggagtacctt atgtgttcaa   1380
agccagtcta tgctgtatct tgaattctgt ggcagccttc acagtgtgag attacacctt   1440
gtttccaaaa ccccaaacag atcaacaaca agcgtgaaaa cagcaaagaa attgttttttc   1500
aaatgggaaa aatcagccgt ttatcttgat gtttccttga gttgcattta taaaagcagc   1560
acacatttct actgaaatct gtggtacgaa gaaaatatgt tatcttccct aatgaatggc   1620
aaatatctga gttgataaac aaactgccag caagtggtgt ctacacatat agatatatca   1680
aaacactaat aatgtgcaca tatttgtata attgtgcatc agctgaaatg gagataaatt   1740
aaaaattagg aatgtgacta gatcatgaag aagcatcaga ccttgggaga gcttagatgt   1800
cccctagcga aatctcctgc ttgcaagact gtactccatg agtcttattt cagagttgag   1860
agggttcaca tctccacacc aggaaccatc acctaagagc acctctccgt ttcctccaca   1920
gggactgaca agttttcgct acatgactgc acaccaaaag aaaaggctaa tacttcaatt   1980
tgtttagagt ggaaaacaga aaaccttgat ttcagaaaat gcaacagtga caatatttca   2040
tatgtactcc actgtgagcc aggtacgatg ctgggcagag aagttctatt atcagaaatt   2100
attccagacg tggcttaaat gttctttctg tagccttgtc ctcctcaccc accctcagtg   2160
atccgccata aattagaata aataaccct agtatctctg gcactgaaac aaaattcacaa   2220
cgtagataaa tgaaaagagc aacccatgga tgataaatat tatgaaaaat taattaaaag   2280
aattttcttg agtactgtta tataccagac attgttgaaa gggtgatgag atgcaggcat   2340
tataaagaa agatggtatc catagtctgt agaaaggaag catagtatta tccacaccgg   2400
```

```
aggttgcttt ctcagacttt catacatgaa aatcattgga aagttcaaga atctgcaggt 2460
agcaaggaaa acaagtgctt ctaggaggga acatgggttt ctctagaggt tggatctttt 2520
aaaacatata tttgaattca gtgaggtgga ctctttctcc tctaggcata cagctatgtg 2580
ccaggacaca cttgacaaga cagagggagg tacatacacc cagaggcgga agaggaaatt 2640
tcactctgat tgtaaacatt gtgctaacag gaaattgctg ggctaagata caaataggat 2700
gttcacagct ggaacaaata tatgttgagt taacattttt ttaaaaaatt ttaaataagt 2760
cacaatactg atttctcaac aaaattgagt atagcaatgt tatctgcagg atcttggttt 2820
attatttcac catttttcaga gacttgacct taacatgaag tcttaaacac atggtgccat 2880
aaaagaagcc catttactat gtggcatttc atatactcat gtgcaatact tacttcttc 2940
agaaaataat acaaaatgca ttagaagaaa tacattcata cctgaaagat gtcagttgga 3000
caaccttcgt gcccaaacaa attacacatg tgtagcagaa atcttatatc gcggtgtaaa 3060
actcgtcaaa aatgttataa atgtgcagac agatttgggg agtaagtata tcgtttatgt 3120
ttataaaata aataaaattt cttttctttt tatgggttta cttttatttt tggagagtca 3180
tagaaaataa tggtatagaa ttacagaaag catatcagtg aagaaaaaag tttaaatgca 3240
cttaaggtc aatttttaaaa actaggttat acaaacctaa ctaaagttct ttttctgttg 3300
ttcaaattgt gtctgccgta agtctggtag aaacacttga aatggtttac atagattatt 3360
cccatttat tcatttctc ctcccttctt tttataacac catttgttct gtattctaac 3420
acttcttca caattatgct ctgcttctaa tagaaataaa ataagcaaag aaactaataa 3480
aactcaagca aatctacatg tttaaacata aaatacggag tatagttatc aaattttggc 3540
aatagaatta ataaccggat aaaccttatt aaatagaaag gggttctact tgggaagtca 3600
gatgtgaaat tttcaaatta aatgtaacat ttgatggtaa atgctaatt ttttaaaatgg 3660
tgattaatga ataatcaacc ataaagaaga caaagatgt cattgctcac aagcagtaaa 3720
gacattttta gaaggaagag aagagaagca gtaggaaagg aggaagggag agatagatga 3780
tagatagata atagatagat agatagatag atagatagat agatagagac agacagacag 3840
acagaaagaa agagagagac agaaacagag agacacaaaa aaagaggaaa gagaagactg 3900
ggagaaaggg aaagtaaggg atggagaaaa aagggagaga gataaaaaga agacaaaaac 3960
ataaatgaaa gcaaggaatg atgatatata tctgttatgt             4000

SEQ ID NO: 22           moltype = DNA   length = 999
FEATURE                 Location/Qualifiers
source                  1..999
                        mol_type = other DNA
                        organism = Mus musculus
SEQUENCE: 22
tatatatata tatacataaa ataaaaagtg gaagccagat gtggtggcac acacttataa 60
tcctagcact ccagaggtag aactaggcta gaaggtgcaa ggccaactag agatatatag 120
tgagactgtc tcagacaaaa cgaaaatgaa taggcaaaca ctcaggaggc agaggaagtg 180
catctctgag agctgcaggc cagtcagggc tacatagtaa gaccctgtca ataataataa 240
taatgcaat aataatttta agaccaaaat aaatagacat ggatgaaggg ggaaaggaat 300
gagaagaagg aagataagcg atgagggagg agatagggtg aaagtggtct gtatgtatta 360
catacatgta caaaattgtc taaaaacaag tttaactaat aagaaaatac aaactaatgt 420
ttgaaaggct acaatgaaat gacaagctta agtgtctcga ttaccacacc cctcccaacc 480
cctcaggcgt caatggacaa gagctcttgc tgcatcgtag ccaccagtac tcagggcagt 540
gtgctcccgg cctggtctgc tcctcggag gctccagacg gcggcctgtt tgcagtgcgg 600
aggcacctct ggggaagcca tggcaatagt tccttcccag gtcagtggag tccacacccc 660
agtgccaggg ggtacaaagg agctccccca ccccctcac ccccactaag agctgggagg 720
aaactgcacc tgagttatt aggcttagaa gccctcaact gttataaatg catagccttg 780
ggccccgtgt tttggggat tggagccagg cctgacctat ttggcatctg ctacttcatt 840
cagtcaccat gagggaggag cctgccaagg tgagtccaaa gagccctctc ttccgtcccc 900
acctccagga agtcaggtgc actcaaccaa gctaaccaac cctctcccac ctgtcaggcc 960
tgggttgtga gtttaccagg gaccatagat atttggtgt                 999

SEQ ID NO: 23           moltype = DNA   length = 1999
FEATURE                 Location/Qualifiers
source                  1..1999
                        mol_type = other DNA
                        organism = Mus musculus
SEQUENCE: 23
actccagttc cagtggatcc aatgcacttt tctgccttcc acaggtacca ggcacacatg 60
cgatgcccag acatgcatgc aggcaaaact cccgtatacc taaaataaaa tgcaagctga 120
cttggcagta atctcagccc atcctgtgct acatagtaca tgttagacta gcctgtacta 180
catgctacat agtacatgtt agactagcct gtactacatg ctacatagta catgttagac 240
tagcctgtac tacagagcaa gagcccacct acataaaat ccaaccaagc aagcaatcat 300
tttttaaagt aaaatggaag actcagtgtg gtggcgcacg cacgccttta atcctagaac 360
tcgggaggca gatgcaggca gatctctgtg agttcgaagc cagtctggtc tacagagcct 420
ggtctataca ctgagctcca ggacagccaa gactacacag agaaacctg tctgaaagaa 480
aaaaaaaata tatatata tatatata tacataaa ataaaaagtg gaagccagat 540
gtggtggcac acacttataa tcctagcact ccagaggtag aactaggcta gaaggtgcaa 600
ggccaactag agatatatag tgagactgtc tcagacaaaa cgaaaatgaa taggcaaaca 660
ctcaggaggc agaggaagtg catctctgag agctgcaggc cagtcagggc tacatagtaa 720
gaccctgtca ataataataa taatgcaat aataatttta agaccaaaat aaatagacat 780
ggatgaaggg ggaaaggaat gagaagaagg aagataagcg atgagggagg agatagggtg 840
aaagtggtct gtatgtatta catacatgta caaaattgtc taaaaacaag tttaactaat 900
aagaaaatac aaactaatgt ttgaaaggct acaatgaaat gacaagctta agtgtctcga 960
ttaccacacc cctcccaacc cctcaggcgt caatggacaa gagctcttgc tgcatcgtag 1020
ccaccagtac tcagggcagt gtgctcccgg cctggtctgc tcctcggag gctccagacg 1080
gcggcctgtt tgcagtgcgg aggcacctct ggggaagcca tggcaatagt tccttcccag 1140
gtcagtggag tccacacccc agtgccaggg ggtacaaagg agctccccca ccccctcac 1200
ccccactaag agctgggagg aaactgcacc tgagttatt aggcttagaa gccctcaact 1260
```

-continued

```
gttataaatg catagccttg ggccccgtgt tttgggggat tggagccagg cctgacctat  1320
ttggcatctg ctacttcatt cagtcaccat gagggaggag cctggccaag tgagtccaaa  1380
gagccctctc ttccgtcccc acctccagga agtcaggtgc actcaaccaa gctaaccaac  1440
cctctcccac ctgtcaggcc tgggttgtga gtttaccagg gaccatagat atttggtgtc  1500
aggctggcta tgccacttga gctgcttaca tgcctttgat gtacaaatta cttgactcct  1560
ttttaaagtg aggagagcta tttggcagga gtactgcaaa gaagacacag cttacgcgg  1620
gtactcagta aacagtacta tgtgtgagca tagactgtcc ctcccccctt ggtgctagtg  1680
gtaggaattg agaccttgga ttcctgatgc agacaaaggt ggggtagggg gtgaggaggc  1740
caaaggctct gatctatgcc aaccttctgc agagttcttc cacaacatgg actacttcaa  1800
gtaccacaat atgcgacccc ctttcaccta tgccacccct atccgatgg taagcagggc   1860
aatagaggcc cagcagctgg tgggcggcag gggggggagtt gtggtgggga gtgcttgcct  1920
cctacattgc accaagagca gaattcaccc attaacaaac ctcagctctg aggagcccca  1980
agatgtgatc cttcttgat                                               1999

SEQ ID NO: 24          moltype = DNA   length = 2000
FEATURE                Location/Qualifiers
source                 1..2000
                       mol_type = other DNA
                       organism = Mus musculus
SEQUENCE: 24
aaatggggac ccacctgtcc taccagctgg ctgacctgta gctttcccca ccacagaatc    60
caagtcggaa ctcttggcac catgaaccca gccatcgtcg tcgctctcct gctctcaggt   120
actgggcaag ggtcagggct ggcattctaa ggaatctggc ttcctcccat cccgggaagt   180
agcctctttg ccatagtctc aggggcacag gtggttggga ggtgcggggg tggggagtgg   240
ggaggagcct caacctcacc agtggtggtc tttgacatat tagaaactcc ataatggatc   300
taggaactcc tcttgctggg tggtggtggt tgtggtaacc accttttaatc tcagcactca   360
ggaggcagag tcaggtggat ctgttagtct gaagccagcc tggtctacag agcaaattcc   420
aggacagcca gagctattct caagatagag aatccctttc ttgaaaaaac catttaaaaa   480
caaaaacaaa agcaacacac tcctcttgat ctcctgttct tgaaacacat tgtgggacc   540
cagaacttca gtagattgat ggaagttgga gtctgcaggt ggtggaacat cccaccaata   600
cctcaagggc gagtgcaaac cccacatccc cccagctcaa gtctacttttt cctgcaggtg   660
ggaggccccg ggtctgtgtc tccccaaatt cagagaaggc actgctgtgc cagtcttgca   720
ggtgtcccga gggcagaagg tgaccagcct gacagcctgc ctggtgaacc aaaaccttcg   780
cctggactgc cgccatgaga ataacaccaa ggataactcc atccagcatg agttcagctc   840
gacccgagag aagaggaagc acgtgctctc aggcacccctt gggataccg agcacacgta   900
ccgctcccgc gtcaccctct ccaaccagcc ctatatcaag gtccttaccc tagccaactt   960
caccaccaag gatgagggcg actactttg tgagcttcga gtctcaggcg cgaatcccat  1020
gagctccaat aaaagtatca gtgtgtatag aggtgagact ggttcccaga agataaaat   1080
gtccaggtta gccaggctgg ggtagccaat aaaaaaaaa aaaaaaaaaa aaaaaaaaac  1140
aggcacctcc attaccccttc ccctaactgc tggtctcctg ggaaactgct gctgtctatg  1200
tgagtggggc aagattaggg gccagaaagg gggagcttgt agtaaaagca cagttgagga  1260
aactaaatgg gaaaggcagt acagtggtga ttcttgtggt gtggaggttc tgttacagca  1320
tccggtggag ccgctaagat gagaaagcgc cagctagctg ccttgaacag tgacacctg   1380
tctttgcccg cctgagtcct gatctcccct cctcccggca ccccttctct atccacagac  1440
aagctggtca agtgtggcgg cataagcctg ctggttcaga acacatcctg gatgctgctg  1500
ctgctgcttt ccctctccct cctccaagcc ctggacttca tttctctgtg actggttggg  1560
cccaaggaga aacaggagcc ctcgaaggtcc ttcctctgca gaggtcttgc ttctcccggt  1620
cagctgactc cctccccaag tccttcaaat atctcagaac atggggagaa acggggacct  1680
tgtccctcct aaggaacccc agtgctgcat gccatcatcc cccccaccct cgccccccacc  1740
cccgccactt ctccctccat gcataccact agctgtcatt ttgtactctg tatttattcc   1800
agggctgctt ctgattattt agtttgttct ttccctggag acctgttaga acataagggc  1860
gtatggtggg tagggaggc aggatatcag tccctggggc gagttcctcc ctgccaacca  1920
agccagatgc ctgaaagaga tatggatgag ggaagttgga ctgtgcctgt acctggtaca  1980
gtcatactct gttgaaagaa                                              2000

SEQ ID NO: 25          moltype = DNA   length = 3679
FEATURE                Location/Qualifiers
source                 1..3679
                       mol_type = other DNA
                       organism = Mus musculus
SEQUENCE: 25
accccatcaa aatcctattt gagtgtacgg ttcggagaac ctcatttatc cggtaaatgt    60
cttttactct gctctcaggg agctgaggca ggacatcctg agatacattg ggagaggaga   120
tacagtttca ataaaataat aggttgggtg gaggtacatg cctataatgc caccactcag   180
gaaatggtgg cagcttcgtg agtttggagc caacccaaga aacatagtga aaccctgtca   240
gtaaataagt aagcaagtat ttgagtatct actatatgct agggctgacc tggacattag   300
gggtcatctt ctgaacaaac tagtgcttga gggaggtatt tgggggttttt gtttgtttaa   360
tggatctgaa tgagttccag agactggcta cacagcgata tgactgagct taacacccct   420
aaagcataca gtcagaccaa ttagacaata aaggtatgt atagcttacc aaataaaaaa   480
attgtatttt caagagagtg tctgtctgtg tagccctggc tgttcttgaa ctcactctgt   540
agaccaggct ggcctggaaa tccatctgcc tgcctctgcc tctctgcctc tctgcctctc   600
tgcctctctc tctgcctctc tctgcctctc tctgcccctc tctgccctc tctgcccctc   660
tctgcccctc tctgccgccc tctgccttct gcctcctgcc ctggcctc tggcctctgc   720
cctctgccct ctggcctctg gcctctgcct ctgctgcttg agtgctggga tcaaggtgt   780
gagctctgta ggtcttaagt tccagaagaa agtaatgaag tcaccagca ggaggtgct   840
cagggacagc acagacacac acccaggaca taggctccca cttccttggc tttctctgag   900
tggcaaagga cctttaggcag tgtcactccc taagagaagg ggataaagag aggggctgag  960
gtattcatca tgtgctccgt ggatctcaag ccctcaaggt aaatggggac ccacctgtcc  1020
taccagctgg ctgacctgta gctttcccca ccacagaatc caagtcggaa ctcttggcac  1080
```

-continued

```
catgaaccca gccatcagcg tcgctctcct gctctcaggt actgggcaag ggtcagggct   1140
ggcattctaa ggaatctggc ttcctcccat cccgggaagt agcctctttg ccatagtctc   1200
aggggcacag gtggttggga ggtgcggggg tggggagtgg ggaggagcct caacctcacc   1260
agtggtggtc tttgacatat tagaaactcc ataatggatc taggaactcc tcttgctggg   1320
tggtggtggt tgtggtacac acctttaatc tcagcactca aggacagag tcaggtggat   1380
ctgttagtct gaagccagcc tggtctacag agcaaattcc aggacagcca gagctattct   1440
caagatagag aatccctttc ttgaaaaaac catttaaaaa caaaaacaaa agcaacacac   1500
tcctcttgat ctcctgttct tgaaacacat tgttgggacc cagaacttca gtagattgat   1560
ggaagttgga gtctgcaagt ggtggaacat cccaccaata cctcaagggc gagtgcaaac   1620
cccacatccc cccagctcaa gtctacttt cctgcaggtg ggaggcccccg ggtctgtgtc   1680
tccccaaatt cagagaaggc actgctgtgc cagtcttgca ggtgtcccga gggcagaagg   1740
tgaccagcct gacagcctgc ctggtgaacc aaaaccttcg cctggactgc cgccatgaga   1800
ataacaccaa ggataactcc atccagcatg agttcagcct gacccgagag aagaggaagc   1860
acgtgctctc aggcacccct gggataccgg agcacacgta ccgtcccgc gtcacccctc   1920
ccaaccagcc ctatatcaag gtccttaccc tagccaactt caccaccaag gatgagggcg   1980
actactttgg tgagcttcga gtctcaggcg cgaatcccat gagctccaat aaaagtatca   2040
gtgtgtatag aggtgagact ggttcccaga agataaaat gtccaggtta gccaggctgg   2100
ggtagccaat aaaaaaaaaa aaaaaaaaaa aaaaaaaaa aggcacctcc attaccctc    2160
ccctaactgc tggtctcctg ggaaactgct gctgtctatg tgagtggggc aagattaggg   2220
gccagaaagg gggagcttgt agtaaaagca cagttgagga aactaaatgg gaaaggcagt   2280
acagtggtga ttcttgtggt gtggaggttc tgttacagca tccggtggag ccgctaagat   2340
gagaaagcgc cagctagctg cctttgaacag ctgacacctg tctttgcccg tctgagtcct   2400
gatctcccct cctcccggca cccccttctct atccacagac aagctggtca agtgtggcgg   2460
cataagcctg ctggttcaga acacatcctg gatgctgctg ctgctgcttt ccctctccct   2520
cctccaagcc ctggacttca tttctctgtg actggttggg cccaaggaga aacaggagcc   2580
ctcgagtgcc ttcctctgca gagtgcttgc ttctcccggt cagctgactc cctccccaag   2640
tccttcaaat atctcagaac atggggagaa acgggaccct tgtccctcct aaggaacccc   2700
agtgctgcat gccatcatcc ccccacccct cgccccccacc cccgccactt ctccctccat   2760
gcataccact agctgtcatt ttgtactctg tatttattcc agggctgctt ctgattattt   2820
agtttgttct ttccctggag acctgttaga acataaggc gtatggtggg tagggagggc   2880
aggatatcag tccctggggc gagttcctcc ctgccaacca agccagatgc ctgaaagaga   2940
tatgggatgag ggaagttgga ctgtgcctgt acctggtaca gtcatactct gttgaaagaa   3000
tcatcgggga gggggggggg ggctcaagat gggagagctc tgctgagcct ttgtggacca   3060
tccaatgagg atgagggctt agattctacc aggtcattct cagccaccac acacaagcgc   3120
tctgccatca ctgaagaagc ccctaggc tcttgggcca gggcacactc agtaaagatg   3180
caggttcagt cagggaatga tggggaaagg ggtaggaggt gggggaggga tcacccctc    3240
ctctaaaca cgagcctgct gtctccaaag gcctctgcct gtagtgaggg tggcagaaga   3300
agacaaggag ccagaactct gactccagga tctaagtccg tgcaggaagg ggatcctaga   3360
accatccggt tggacccagc ttaccaaggg agagccttta ttcttcttc ccttgcccct   3420
ctgtgccagc ccctcttgct gtccctgatc ccccagacag cgagagtctt gcaacctgcc   3480
tcttccaaga cctcctaatc tcaggggcag gcggtggagt gagatccggc gtgcacactt   3540
tttggaagat agctttccca aggatcctct cccccactgg cagctctgcc tgtcccatca   3600
ccatgtataa taccaccact gctacagcat ctcaccgagg aaagaaaact gcacaataaa   3660
accaagcctc tggagtgtg                                               3679
```

```
SEQ ID NO: 26           moltype = DNA   length = 960
FEATURE                 Location/Qualifiers
source                  1..960
                        mol_type = other DNA
                        organism = Mus musculus
SEQUENCE: 26
cacattgttg ggacccagaa cttcagtaga ttgatggaag ttggagtctg caagtggtgg    60
aacatcccac caatacctca agggcgagtg caaaccccac atcccccag ctcaagtcta   120
cttttcctgc aggtgggagg ccccgggtct gtgtctcccc aaattcagag aaggcactgc   180
tgtgccagtc ttgcaggtgt cccgagggca gaaggtgacc agcctgacag cctgcctggt   240
gaaccaaaac cttcgcctga ctgccgccat gagaataaca ccaaggataa ctccatccag   300
catgagttca gcctgacccg agagaagagg aagcacgtgc tctcaggcac ccttgggata   360
cccgagcaca cgtaccgctc ccgcgtcacc ctctccaacc agcctatat caaggtcctt   420
accctagcca acttcaccac caaggatgag ggcgactact tttgtgagct tcgagtctca   480
ggcgcgaatc ccatgagctc caataaaagt atcagtgtgt atagaggtga gactggttcc   540
cagaaagata aatgtccag gttagccagg ctggggtagc aataaaaaa aaaaaaaaaa   600
aaaaaaaaaa aaacaggcac ctccattacc cttcccctaa ctgctggtct cctgggaaac   660
tgctgctgtc tatgtgagtg gggcaagatt aggggccaga aaggggagc ttgtagtaaa   720
agcacagttg aggaaactaa atggaaagg cagtacagtg gtgattcttg tggtgggag   780
gttctgttac agcatccggt ggagccgcta agatgagaaa gcgccagcta gctgccttga   840
acagctgaca cctgtctttg cccgctgag tcctgatctc ccctcctccc ggcacccctt   900
ctctatccac agacaagctg gtcaagtgtg gcggcataag cctgctggtt cagaacacat   960
```

```
SEQ ID NO: 27           moltype = DNA   length = 160
FEATURE                 Location/Qualifiers
source                  1..160
                        mol_type = other DNA
                        organism = Mus musculus
SEQUENCE: 27
cgtcaccctc tccaaccagc cctatatcaa ggtccttacc ctagccaact tcaccaccaa    60
ggatgagggc gactactttt gtgagcttcg agtctcaggc gcgaatccca tgagctccaa   120
taaaagtatc agtgtgtata gaggtgagac tggttcccag                        160
```

```
SEQ ID NO: 28           moltype = DNA   length = 23
```

```
FEATURE                 Location/Qualifiers
misc_feature            1..23
                        note = Synthetic Primer
source                  1..23
                        mol_type = other DNA
                        organism = synthetic construct
SEQUENCE: 28
gagggcctat ttcccatgat tcc                                              23

SEQ ID NO: 29           moltype = DNA  length = 19
FEATURE                 Location/Qualifiers
misc_feature            1..19
                        note = Synthetic Primer
source                  1..19
                        mol_type = other DNA
                        organism = synthetic construct
SEQUENCE: 29
tcttctcgaa gacccggtg                                                   19

SEQ ID NO: 30           moltype = DNA  length = 20
FEATURE                 Location/Qualifiers
misc_feature            1..20
                        note = Synthetic Primer
source                  1..20
                        mol_type = other DNA
                        organism = synthetic construct
SEQUENCE: 30
aacagccgcg agagaatgaa                                                  20

SEQ ID NO: 31           moltype = DNA  length = 20
FEATURE                 Location/Qualifiers
misc_feature            1..20
                        note = SyntheticPrimer
source                  1..20
                        mol_type = other DNA
                        organism = synthetic construct
SEQUENCE: 31
tcggccttgg tcagattgtc                                                  20

SEQ ID NO: 32           moltype = DNA  length = 63
FEATURE                 Location/Qualifiers
source                  1..63
                        mol_type = other DNA
                        organism = Mus musculus
SEQUENCE: 32
aaaaggctaa tacttcaatt tgtttggagt ggaaaacaaa aaaccttgat ttcagaaaat      60
gca                                                                    63

SEQ ID NO: 33           moltype = DNA  length = 63
FEATURE                 Location/Qualifiers
source                  1..63
                        mol_type = other DNA
                        organism = Mus musculus
SEQUENCE: 33
aaaaggctaa tacttcaatt tgtttagagt ggaaaacaga aaaccttgat ttcagaaaat      60
gca                                                                    63

SEQ ID NO: 34           moltype = DNA  length = 63
FEATURE                 Location/Qualifiers
source                  1..63
                        mol_type = other DNA
                        organism = Mus musculus
SEQUENCE: 34
ggatccagct gcaagaaaaa cgttagtctc ttggcctgag cctgtatcta aacctgagtc      60
tga                                                                    63

SEQ ID NO: 35           moltype = DNA  length = 63
FEATURE                 Location/Qualifiers
source                  1..63
                        mol_type = other DNA
                        organism = Mus musculus
SEQUENCE: 35
ggatccagct gcaagaaaaa cgttagtctc ttggcctgag cctgcatcta aacctgatcc      60
tga                                                                    63

SEQ ID NO: 36           moltype = DNA  length = 63
FEATURE                 Location/Qualifiers
source                  1..63
                        mol_type = other DNA
```

```
                        organism = Mus musculus
SEQUENCE: 36
aaaatattaa gataacaaat gtctctttat tttgataggt ccggacaagg tcaatggaat    60
gaa                                                                 63

SEQ ID NO: 37           moltype = DNA   length = 63
FEATURE                 Location/Qualifiers
source                  1..63
                        mol_type = other DNA
                        organism = Mus musculus
SEQUENCE: 37
aaaatattaa gataacaaat gtctctttat tttgataggt ccagacaagg tcactggaat    60
gaa                                                                 63

SEQ ID NO: 38           moltype = DNA   length = 63
FEATURE                 Location/Qualifiers
source                  1..63
                        mol_type = other DNA
                        organism = Mus musculus
SEQUENCE: 38
gcctcaatgg acaagagctc ttgctgcatc gtagccacca gtactcaggg cagtgtgctc    60
ccg                                                                 63

SEQ ID NO: 39           moltype = DNA   length = 63
FEATURE                 Location/Qualifiers
source                  1..63
                        mol_type = other DNA
                        organism = Mus musculus
SEQUENCE: 39
gcctcaatgg actagatatc ttgctgcatc gtagccacca gtactcaggg cagtgtgctc    60
ccg                                                                 63

SEQ ID NO: 40           moltype = DNA   length = 63
FEATURE                 Location/Qualifiers
source                  1..63
                        mol_type = other DNA
                        organism = Mus musculus
SEQUENCE: 40
gcctcaatgg acaaaagagc tcttgctgca tcgtagccac cagtactcag gcagtgtgc    60
tcc                                                                 63

SEQ ID NO: 41           moltype = DNA   length = 24
FEATURE                 Location/Qualifiers
source                  1..24
                        mol_type = other DNA
                        organism = Mus musculus
SEQUENCE: 41
ttttgtgagc ttcgagtctc gggc                                          24

SEQ ID NO: 42           moltype = DNA   length = 24
FEATURE                 Location/Qualifiers
source                  1..24
                        mol_type = other DNA
                        organism = Mus musculus
SEQUENCE: 42
ttttgtgagc ttcaagtctc gggc                                          24

SEQ ID NO: 43           moltype = DNA   length = 22
FEATURE                 Location/Qualifiers
misc_feature            1..22
                        note = Synthetic Primer
source                  1..22
                        mol_type = other DNA
                        organism = synthetic construct
SEQUENCE: 43
actatcatat gcttaccgta ac                                            22

SEQ ID NO: 44           moltype = DNA   length = 33
FEATURE                 Location/Qualifiers
misc_feature            1..33
                        note = Synthetic Primer
source                  1..33
                        mol_type = other DNA
                        organism = synthetic construct
SEQUENCE: 44
taagcaggat ccattcctta ggaccaccac ctg                                33

SEQ ID NO: 45           moltype = DNA   length = 35
FEATURE                 Location/Qualifiers
```

```
misc_feature            1..35
                        note = Synthetic Primer
source                  1..35
                        mol_type = other DNA
                        organism = synthetic construct
SEQUENCE: 45
tgcttagtcg acacaccgcg atataagatt tctgc                         35

SEQ ID NO: 46           moltype = DNA  length = 20
FEATURE                 Location/Qualifiers
misc_feature            1..20
                        note = Synthetic Primer
source                  1..20
                        mol_type = other DNA
                        organism = synthetic construct
SEQUENCE: 46
gagaaagcaa cctccggtgt                                          20

SEQ ID NO: 47           moltype = DNA  length = 54
FEATURE                 Location/Qualifiers
source                  1..54
                        mol_type = other DNA
                        organism = Mus musculus
SEQUENCE: 47
caaaagaaaa ggctaatact tcaatttgtt tggagtggaa aacaaaaaac cttg    54

SEQ ID NO: 48           moltype = DNA  length = 54
FEATURE                 Location/Qualifiers
source                  1..54
                        mol_type = other DNA
                        organism = Mus musculus
SEQUENCE: 48
caaaagaaaa ggctaatact tcaatatgtt tggagtggaa aacaaaaaac cttg    54

SEQ ID NO: 49           moltype = DNA  length = 54
FEATURE                 Location/Qualifiers
source                  1..54
                        mol_type = other DNA
                        organism = Mus musculus
SEQUENCE: 49
caaaagaaaa ggctaatact tcaatttgtt tagagtggaa aacagaaaac cttg    54

SEQ ID NO: 50           moltype = DNA  length = 46
FEATURE                 Location/Qualifiers
source                  1..46
                        mol_type = other DNA
                        organism = Mus musculus
SEQUENCE: 50
caaaagaaaa ggctaatacg tttggagtgg aaaacaaaaa accttg             46

SEQ ID NO: 51           moltype = DNA  length = 55
FEATURE                 Location/Qualifiers
source                  1..55
                        mol_type = other DNA
                        organism = Mus musculus
SEQUENCE: 51
caaaagaaaa ggctaatact tcaatttagt ttggagtgga aaacaaaaaa ccttg   55

SEQ ID NO: 52           moltype = DNA  length = 38
FEATURE                 Location/Qualifiers
source                  1..38
                        mol_type = other DNA
                        organism = Mus musculus
SEQUENCE: 52
caaaagaaaa ggctaatagt ggaaaacaaa aaaccttg                      38

SEQ ID NO: 53           moltype = DNA  length = 40
FEATURE                 Location/Qualifiers
source                  1..40
                        mol_type = other DNA
                        organism = Mus musculus
SEQUENCE: 53
caaaagaaaa ggctaatgga gtggaaaaca aaaaaccttg                    40

SEQ ID NO: 54           moltype = DNA  length = 53
FEATURE                 Location/Qualifiers
source                  1..53
                        mol_type = other DNA
                        organism = Mus musculus
```

```
SEQUENCE: 54
caaaagaaaa ggctaatact tcaattgttt ggagtggaaa acaaaaaacc ttg            53

SEQ ID NO: 55           moltype = DNA   length = 55
FEATURE                 Location/Qualifiers
source                  1..55
                        mol_type = other DNA
                        organism = Mus musculus
SEQUENCE: 55
caaaagaaaa ggctaatact tcaattttgt ttggagtgga aaacaaaaaa ccttg          55

SEQ ID NO: 56           moltype = DNA   length = 55
FEATURE                 Location/Qualifiers
source                  1..55
                        mol_type = other DNA
                        organism = Mus musculus
SEQUENCE: 56
caaaagaaaa ggctaatact tcaatttagt ttggagtgga aaacaaaaaa ccttg          55

SEQ ID NO: 57           moltype = DNA   length = 55
FEATURE                 Location/Qualifiers
source                  1..55
                        mol_type = other DNA
                        organism = Mus musculus
SEQUENCE: 57
caaaagaaaa ggctaatact tcaactccgt ttggagtgga aaacaaaaaa ccttg          55

SEQ ID NO: 58           moltype = DNA   length = 58
FEATURE                 Location/Qualifiers
source                  1..58
                        mol_type = other DNA
                        organism = Mus musculus
SEQUENCE: 58
caaaagaaaa ggctaatact tcaattaggg tgtttggagt ggaaaacaaa aaaccttg      58

SEQ ID NO: 59           moltype = DNA   length = 56
FEATURE                 Location/Qualifiers
source                  1..56
                        mol_type = other DNA
                        organism = Mus musculus
SEQUENCE: 59
caaaagaaaa ggctaatact tcaattttg tttggagtgg aaaacaaaaa accttg         56

SEQ ID NO: 60           moltype = DNA   length = 53
FEATURE                 Location/Qualifiers
source                  1..53
                        mol_type = other DNA
                        organism = Mus musculus
SEQUENCE: 60
caaaagaaaa ggctaatact tcaattgttt ggagtggaaa acaaaaaacc ttg            53

SEQ ID NO: 61           moltype = DNA   length = 43
FEATURE                 Location/Qualifiers
source                  1..43
                        mol_type = other DNA
                        organism = Mus musculus
SEQUENCE: 61
caaaagaaaa ggctatgttt ggagtggaaa acaaaaaacc ttg                       43
```

ALLELE EDITING AND APPLICATIONS THEREOF

CROSS-REFERENCE TO RELATED APPLICATIONS

The patent application is continuation of U.S. application Ser. No. 16/096,074 filed Oct. 24, 2018, now U.S. Pat. No. 11,499,168, which is a 371 of PCT/EP2017/059799 filed on Apr. 25, 2017, which claimed the priority of European patent applications EP16166857.9 filed on Apr. 25, 2016, EP16166854.6 filed on Apr. 25, 2016, EP16166856.1 filed Apr. 25, 2016, EP16196858.1 filed Nov. 2, 2016, EP16196860.7 filed Nov. 2, 2016, and EP16196856.5 filed Nov. 2, 2016.

STATEMENT REGARDING FEDERALLY SPONSORED RESEARCH OR DEVELOPMENT

This invention was made with government support under Award Number R01AI106923 awarded by National Institute of Allergy and Infectious Diseases of the National Institutes of Health, USA. The government has certain rights in the invention.

SEQUENCE LISTING

This document incorporates by reference an electronic sequence listing text file, which was electronically submitted on Dec. 21, 2022. The text file is named 2022-12-21_13500094US2_seqlisting, is 79,428 bytes, and was created on Sep. 16, 2022.

FIELD OF THE INVENTION

The present invention relates to a method to monitor and optimize the efficiency of homology directed repair of DNA double strand breaks during gene editing, in particular CRISPR/Cas gene editing. The invention further relates to a method of enriching a cell preparation for cells that have undergone HDR, based on HDR multiplexing, and to a method for selective depletion of edited cells in vitro or in vivo.

INTRODUCTION

CRISPR-based genetic engineering is a flexible way of introducing genomic mutations in cells. Double strand DNA (dsDNA) breaks can be induced at desired genomic loci through the use of "programmable", user-defined short guide RNAs which complex with a nuclease. Frequently used nucleases include Gas proteins, particularly Cas9, but can be variations thereof. Variations include altered nucleases with altered DNA binding specificities or fusion proteins which add distinct features such as transcriptional activation or repression or enzymatic activity to directly edit nucleotides. Gas nucleases can also be modified to induce single-stranded "nicks" to genomic DNA. The cellular response to these induced DNA breaks is the activation of the DNA repair machinery which mainly consists of the non-homologous end joining (NHEJ) pathway and the homology directed repair (HDR) pathway. NHEJ usually results in random insertions and deletions (indels) which can be exploited to delete genes. This can be useful for experimental purposes, but for clinical use the inherently stochastic NHEJ repair pathway bears significant risks. Targeted, precise gene editing is safer and therefore more desirable.

The HDR pathway provides the opportunity to introduce precise mutations by repairing a (ds)DNA break based on a DNA template. However, exploiting the HDR pathway for biotechnology purposes is much less efficient than exploiting NHEJ. NHEJ and HDR happen in a ratio of approx. 9:1. A bottleneck to overcome the low HDR efficiency is the absence of simple systems to quantitate NHEJ and HDR events in single cells. Many assays to assess gene editing events are semi-quantitative. Sequencing of entire cell populations does not provide information about the frequency of events per cell and does not allow the discrimination of homozygosity vs. heterozygosity. Although cell lines can be cloned to obtain single cell information, this approach is tedious and is not possible in primary cells. Alternatively, flow cytometry-based reporter systems have been developed to quantify gene editing on a single cell basis. However, such systems depend on genetic manipulation of the assessed cells or organisms (mostly prior to their use), thus restricting their use.

The problem underlying the present invention is to provide a simple cost-effective system, which allows rapid single cell based quantification of gene editing events without the need for transgenes and without the need for prior manipulation of cells. Another problem underlying the present invention is to provide a system that serves to permanently mark and track cells and allows the selective depletion of the marked or unmarked cells in vitro or in vivo. These problems are solved by the subject-matter of the independent claims.

DESCRIPTION

According to a first aspect of the invention, a method to determine a first homology directed repair (HDR) event is provided. The HDR event occurs at a first genomic location within a eukaryotic cell. The cell expresses a first isoform (allele) of a first surface protein, which is different from a second isoform (allele) of said first surface protein with regard to an amino acid marker, wherein the first isoform comprises amino acid marker A encoded by nucleic acid sequence A, and the second isoform comprises amino acid marker B encoded by nucleic acid sequence B. The first genomic location comprises nucleic acid sequence A. The method comprises the steps of:

a. inducing a first DNA double strand break at said first genomic location;
b. providing a first DNA repair construct comprising said nucleic acid sequence B and a first pair of homology arms (which are homologous to the DNA sequences 5' and 3' of said first genomic location), in particular transfecting said cell with said first DNA repair construct;
c. determining the expression of the first and/or second isoform of the first surface protein on said cell and optionally purifying said cell based on the expression of the first and/or second isoform of the surface protein; and
d. determining the occurrence of said first HDR event, wherein expression of said second isoform of said first surface protein on said cell is equivalent to occurrence of said first HDR event.

In the context of the present specification, the expressions "first and/or second isoform of the cell surface protein" refer to a first and a second allele of the cell surface protein. The alleles can be distinguished by ligands specifically binding to each allele/isoform. In certain embodiments, the alleles are functionally identical.

In the context of the present specification, the expression "DNA repair construct" refers to a DNA construct that is used as a template to repair a DNA strand lesion, particularly a double strand break (DSB), within the genomic DNA by HDR. A DNA repair construct comprises homology arms and a transgenic sequence of interest. The homology arms are homologous to the genomic DNA sequences 5' and 3' of the DSB. The transgenic sequence of interest is located between the homology arms. During genomic DNA repair by HDR, the transgenic sequence of interest is inserted into the genomic DNA. The skilled person is aware that the DNA repair construct can be linear (single stranded or double stranded) or circular (e.g. plasmid, minicircle plasmid).

Ideally, the first genomic location (the location where the DSB occurs) corresponds to nucleic acid sequence A. In instances where this is not feasible (due to the requirements of guide RNA design) the first genomic location may also be up to 20 bp in 5' or 3' direction of nucleic acid sequence A. In instances where this is not feasible (due to the requirements of guide RNA design) the first genomic location may also be up to 50 bp in 5' or 3' direction of nucleic acid sequence A. With a distance greater than 20 bp, the HDR efficiency decreases significantly.

In certain embodiments, the occurrence of said first HDR event is determined at at least two different experimental conditions, and an increased ratio of expression of said second isoform to said first isoform at a first experimental condition compared to a second experimental condition indicates an increased HDR efficiency at said first experimental condition.

This system enables rapid single cell based quantification of gene editing events without the need for transgenes and without the need for prior manipulation. This system can therefore be employed in primary cells in contrast to cell lines or cell clones which are required if multiple manipulations are necessary to introduce the marker systems first.

In certain embodiments, step a and b are performed in cell culture medium comprising vanillin and/or of rucaparib, particularly at a concentration of 50 pM to 500 pM vanillin and/or 0.5 pM to 2.5 pM of rucaparib, more particularly approx. 300 pM vanillin and/or approx. 1 pM of rucaparib.

Within the context of the present specification, vanillin refers to 4-Hydroxy-3-methoxybenzaldehyde, CAS No. 121-33-5.

Within the context of the present specification, rucaparib refers to 8-Fluoro-2-{4-[(methylamino)methyl]phenyl}-1,3,4,5-tetrahydro-6H-azepino[5,4,3-cd]indol-6-one, CAS No. 283173-50-2.

In certain embodiments, the first and said second isoform of the first surface protein can be distinguished from each other by a first ligand and a second ligand specifically binding to said amino acid marker A and said amino acid marker B, respectively.

In the context of the present specification, the expression "ligand specifically binding" refers to an antibody or an antibody-like molecule.

In the context of the present specification, the term "antibody" is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region (VH) and a heavy chain constant region (CH). The heavy chain constant region is comprised of three domains, CH1, CH2 and CH3. Each light chain is comprised of a light chain variable region (abbreviated herein as VL) and a light chain constant region (CL). The light chain constant region is comprised of one domain, CL. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

The term "antibody-like molecule" in the context of the present specification refers to a molecule capable of specific binding to another molecule or target with high affinity/a $K_d<10E-8$ mol/l. An antibody-like molecule binds to its target similarly to the specific binding of an antibody. The term antibody-like molecule encompasses a repeat protein, such as a designed ankyrin repeat protein (Molecular Partners, Zurich), a polypeptide derived from armadillo repeat proteins, a polypeptide derived from leucine-rich repeat proteins, an antibody-derived molecule, such as a chimeric antigen receptor (CAR) and a polypeptide derived from tetratricopeptide repeat proteins.

The term antibody-like molecule further encompasses a polypeptide derived from protein A domains, a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide and a polypeptide derived from a knottin.

The ligand may be an antibody, a Fab (fragment antigen-binding) fragment, a chimeric antigen receptor (CAR) or any other ligand able to recognize a specific isoform of the surface protein. Ideally, two ligands are used, wherein one ligand is able to specifically recognize the first isoform and the other ligand is able to specifically recognize the second isoform. In other words, each ligand is able to specifically bind to one isoform, but not able to specifically bind to the other isoform. In the context of the present specification, the expression "specific binding" refers to binding with a dissociation constant $K_D<10$ E-7. In other words, the ligands (antibodies) are able to discriminate between the isoforms and bind only one isoform, but not the other one.

In certain embodiments, the first surface protein is a native protein. This native protein may or may not exist in various versions, i.e. different isoforms/allelic variants. In the context of the present specification, the expression "native protein" refers to a protein that is encoded by a nucleic acid sequence within the genome of the cell, wherein this nucleic acid sequence has not been inserted by genetic manipulation. In other words, a native protein is a protein that is not a transgenic protein. Allelic variants can occur in populations of organisms through variation of a single or a few nucleotides of a particular nucleic acid sequence. In certain embodiments, an artificial epitope has been introduced into the native protein. Such an artificial epitope may be introduced by genetic manipulation of a short nucleotide sequence, in particular 1 to 10 nucleotides. In instances where an artificial epitope is introduced into a native protein, the nucleic acid sequence encoding the entire protein has not been inserted by genetic manipulation, but only the short nucleic acid sequence encoding the artificial epitope.

In certain embodiments, the first surface protein is a transgenic protein. In the context of the present specification, the expression "transgenic protein" refers to a protein that is encoded by a nucleic acid sequence within the genome of the cell, wherein this nucleic acid sequence has been inserted by genetic manipulation.

In certain embodiments, the purifying is done by flow cytometry. In certain embodiments, the purifying is done by fluorescent activated cell sorting (FACS).

In certain embodiments, the purifying comprises magnetic-bead based enrichment of a cell expressing said first or said second isoform of said first surface protein. This enrichment may either be performed directly, by isolating cells that have undergone HDR (and thus express the second isoform of the surface protein) or indirectly, by removing cells that have not undergone HDR (and thus still express the first isoform of the surface protein). Potentially, binding of an antibody to a surface protein may cause unwanted biological effects within a cell. Indirect enrichment is thus preferred, because it leaves the edited cells "untouched".

In certain embodiments, the first surface protein is Thy1 or CD45.

Within the context of the present specification, "Thy1" refers to "*Mus musculus* thymus cell antigen 1", theta; alternative name: CD90; NCBI Gene ID 21838; NCBI protein ID NP 033408.1.

Within the context of the present specification, "CD45" refers to "*Mus musculus* protein tyrosine phosphatase, receptor type, C (Ptprc)"; NCBI Gene ID 19264; NCBI protein ID NP 001104786.

In certain embodiments, the first surface protein is CD4. In certain embodiments, the first surface protein is CD2. In certain embodiments, the first surface protein is CD8. In certain embodiments, the first surface protein is CD19. In certain embodiments, the first surface protein is HLA.

In certain embodiments, the double strand break is induced in the first genomic location by transfecting the cell with a DNA expression construct encoding a CRISPR-associated endonuclease (Cas9) and a guide RNA, wherein said guide RNA is capable of annealing to said first genomic location.

The skilled person is aware that the expression "the guide RNA is capable of annealing to the genomic location of interest" refers to the fact that part of the guide RNA (the user-defined "targeting sequence") is capable of annealing to the genomic location of interest under high stringency conditions. The guide RNA comprises other parts that are not capable of annealing to the genomic location of interest. By (partly) annealing to the genomic location of interest, the guide RNA directs the CRISPR-associated endonuclease to the genomic location of interest, thereby effecting a DSB at the genomic location of interest.

In the context of the present specification, "CRISPR-associated endonuclease" refers to a Cas9 endonuclease known in the art to facilitate CRISPR-like sequence-guided cleavage of DNA strands. Non-limiting examples of a CRISPR-associated endonuclease are the Cas9 endonucleases of *Streptococcus pyogenes* (SpyCas9), the Cpf1 endonuclease of *Francisella* (FnCpf1), Acidaminococcus (AsCpf1) and *Lachnospiraceae bacterium* (LbCpf1), to any orthologues of SpyCas9, FnCpf1, AsCpf1 or LbCpf1, or to any engineered protein variants of SpyCas9, FnCpf1, AsCpf1 or LbCpf1 or their orthologues. The skilled person is aware that the invention also encompasses newly discovered or engineered CRISPR/Cas variants.

In the context of the present specification, the term "orthologue" refers to a gene and its corresponding polypeptide that evolved by vertical descent from a single ancestral gene. In other words, orthologues genes/polypeptides share a common ancestor and were divided when a species diverged into two separate species. The copies of a single gene in the two resulting species are then referred to as orthologues. To ascertain that two genes are orthologues a person skilled in the art can carry out a phylogenetic analysis of the gene lineage by comparing the aligned nucleotide or amino acid sequences of genes or polypeptides.

In the context of the present specification, the term "guide RNA" refers to a synthetic RNA able to guide a CRISPR-associated endonuclease to a genomic location of interest (where the endonuclease will cleave a phosphodiester bond within the genomic DNA). The skilled person is aware that if a Cas9 endonuclease is used, the expression "guide RNA" may refer to a single guide RNA (sgRNA) comprising both a sequence necessary for Cas9-binding and a user-defined "targeting sequence", or to a combination of two RNA molecules, wherein one comprises the sequence necessary for Cas9-binding (tracrRNA) and the other comprises the user-defined "targeting sequence" (crRNA). If a Cpf1 endonuclease is used, the expression "guide RNA" refers to a single RNA molecule comprising both the sequence necessary for Cpf1-binding and the user-defined "targeting sequence" or several guide RNAs transcribed as a single crRNA array (Zetsche, Nat Biotech, 2016). The "targeting sequence" is able to anneal to the genomic location of interest and thus defines the genomic target to be modified and usually comprises approximately 20 nucleotides.

DNA cleavage by Cas9 is dependent on the presence of a short protospacer adjacent motif (PAM) in the target DNA, restricting the choice of targetable sequences. CAS9 from *Streptococcus pyogenes* (SpyCas9) for example corresponds to the PAM sequence 5-NGG-3'. In certain embodiments, the DNA repair construct comprises a mutated PAM sequence. The mutation renders the PAM sequence non-functional but does not affect protein expression, stability or function. The use of a DNA repair construct comprising a mutated PAM sequence enhances HDR efficiency.

The skilled person is aware that besides the CRISPR system, alternative means for site specific DNA editing exist, namely the use of Zinc finger endonucleases, transcription activator-like effector nucleases (TALEN), meganucleases or argonaute-based systems (Nat Biotechnol. 2016 July; 34(7):768-73) or base editors (Komor et al., Nature 533, 420-424, doi:10.1038/nature17946). The invention also encompasses the use of those alternative means for site specific DNA editing.

In certain embodiments, the first DNA repair construct is not a substrate for the CRISPR system employed in the first step of the method (introducing a strand break into the genomic DNA), because it does not comprise a PAM sequence. Thereby, the inserted sequence can no longer be cut after insertion by a second endonuclease event.

In certain embodiments, HDR enhancing reagents are used during step B.

In the context of the present specification, the expression "HDR enhancing reagent" refers to a reagent capable of impairing the non-homologous end joining (NHEJ) repair pathway and thus indirectly promoting the HDR pathway or to a reagent which directly enhances the HDR pathway. The cellular response to a DNA double strand break is the activation of the DNA repair machinery which mainly consists of the NHEJ pathway and the HDR pathway. NHEJ usually results in random insertions and deletions (indels), which can be exploited to delete genes. This can be useful for experimental purposes, but for clinical use the inherently stochastic NHEJ repair pathway bears significant risks. The probability of a DSB being repaired via the NHEJ pathway is much higher than a DSB being repaired via the HDR pathway (approx. 9:1). Blocking the NHEJ pathway results in a shift of the cellular response towards the HDR pathway.

In certain embodiments, the homology arms comprise approximately 2000 basepairs (bp) each.

In certain embodiments, a second HDR event is determined at a second genomic location within the same cell. The cell expresses a first isoform of a second surface protein, which is different from a second isoform of the second surface protein with regard to an amino acid marker, wherein the first isoform comprises amino acid marker Y encoded by nucleic acid sequence Y, and the second isoform comprises amino acid marker Z encoded by nucleic acid sequence Z. The second genomic location comprises the nucleic acid sequence Y. The method comprises the following additional steps e-h, which are conducted in parallel to steps a-d:
  e. inducing a second DNA double strand break at the second genomic location;
  f. providing a second DNA repair construct comprising nucleic acid sequence Z and a second pair of homology arms (which are homologous to the DNA sequences 5' and 3' of said second genomic location);
  g. determining the expression of the first and/or second isoform of the second surface protein on said cell and optionally sorting said cell based on the expression of the first and/or second isoform of the second surface protein; and
  h. determining the occurrence of said second HDR event, wherein expression of the second isoform of the second surface protein on said cell is equivalent to occurrence of said second HDR event.

According to a second aspect of the invention, a method for editing a genomic location of interest within a eukaryotic cell by inserting a transgenic nucleic acid sequence into the genomic location of interest is provided. The method comprises the determination of a first HDR event at a first genomic location according to the first aspect of the invention, wherein said first genomic location serves as a surrogate genomic location. The method further comprises the following steps, which are conducted in parallel to steps a-d:
  e. inducing a DNA double strand break at the genomic location of interest;
  f. providing a DNA repair construct comprising said transgenic DNA sequence and a pair of homology arms homologous to the DNA sequences 5' and 3' of said genomic location of interest; and
  g. isolating the cells in which said first HDR event has occurred at said first genomic location, thereby enriching for cells in which said transgenic nucleic acid sequence has been successfully inserted into a second genomic location, namely said genomic location of interest.

The inventors have demonstrated that multiplexed HDR is possible in individual cells. Surprisingly, the probability of HDR at a genomic location of interest is increased in cells that have undergone HDR at another (surrogate) genomic location compared to cells that have not undergone HDR at the surrogate genomic location (FIG. 3). Unexpectedly, the inventors could also show that it is possible to enrich for cells with heterozygous HDR at the genomic location of interest by isolating cells that have undergone heterozygous HDR at the surrogate genomic location, and to enrich for cells with homozygous HDR at the genomic location of interest by isolating cells that have undergone homozygous HDR at the surrogate genomic location (FIG. 3).

According to certain embodiments of the second aspect of the invention, the eukaryotic cell is a T cell, the genomic location of interest is the $Foxp3^{K276X}$ mutation, and the DNA template comprises the wild type allele of said Foxp3 mutation, in particular the DNA template is or comprises SEQ ID NO 022 or SEQ ID NO 023.

The inventors have shown that it is possible to correct the $Foxp3^{K276X}$ mutation in murine T cells using the method according to the invention (FIG. 4).

In certain embodiments of the first aspect of the invention, purification of cells based on the expression of the first and/or the second isoform of the surface protein is employed to effect selective depletion of cells expressing the first and/or the second isoform of the surface protein (FIG. 6).

According to another aspect of the invention, a method for selectively depleting or enriching an edited cell in a composition of edited and non-edited cells is provided. The non-edited cells express a first isoform of a surface protein and the edited cell has been edited by the method according to the first aspect of the invention to express a second isoform of the surface protein, which is different from the first isoform with regard to an amino acid marker. The first isoform comprises amino acid marker A encoded by nucleic acid sequence A, and the second isoform comprises amino acid marker B encoded by nucleic acid sequence B. The edited cell is selectively enriched or depleted based on the expression of the first or the second isoform of the surface protein (FIGS. 6 and 25-29).

Alternatively, this aspect of the invention can be formulated as a method for selectively depleting or enriching a cell in a composition of non-edited and edited cells. The method comprises the steps of
  a. providing a cell, wherein the cell expresses a first isoform of a surface protein, which is different from a second isoform of the surface protein with regard to an amino acid marker, wherein the first isoform comprises amino acid marker A encoded by nucleic acid sequence A, and the second isoform comprises amino acid marker B encoded by nucleic acid sequence B;
  b. inducing a DNA double strand break at a genomic location comprising the nucleic acid sequence A;
  c. providing a DNA repair construct comprising the nucleic acid sequence B and a pair of homology arms which are homologous to the DNA sequences 5' and 3' of the genomic location, in particular transfecting said cell with said DNA repair construct;
  d. selectively enriching/depleting the cell based on the expression of the first or the second isoform of the surface protein.

In the context of the present specification, the term "selective depletion of cells" relates to selectively reducing the total number or concentration of cells expressing a certain marker/allele.

By way of non-limiting example, selective depletion can be achieved by complement-dependent cytotoxicity (GDC), Antibody-dependent cellular cytotoxicity (ADCC), Antibody-drug conjugate (ADC) or cells carrying a natural antigen receptor or a chimeric antigen receptor (CAR).

The inventors have demonstrated that selective in vivo depletion is possible using antibodies against CD45.2 or CD45.1, respectively (FIGS. 25-29).

The skilled person is aware that the depletion of non-edited cells corresponds to enrichment of edited cells.

The inventors demonstrate that a single amino acid difference can be engineered into a cell and can be discriminated by two different ligands that specifically bind to the two isoforms/alleles (native vs. engineered). A specifically designed artificial mutation or a rare but naturally occurring mutation such as a single nucleotide polymorphism (SNP) is engineered into an endogenous surface expressed gene to change its antigenicity. The skilled person is aware that this mutation may be introduced by any method known in the field, including HDR and base editors. This altered epitope is subsequently exploited to selectively deplete successfully edited cells with a ligand which specifically and selectively recognizes this artificial epitope. Alternatively, the edited cells are rendered resistant to depletion by a ligand which recognizes the natural epitope (and hence can deplete host cells) but does not recognize the altered epitope and therefore spares the transferred cells.

In instances where the "edited/engineered cells" (cells in which the first isoform of the cell surface protein has been changed to the second isoform) are subsequently used for transplantation, in particular adoptive transfer, the two different isoforms can be used to discriminate between transferred cells and host cells. This enables tracking of the transferred cells since they are permanently marked. Tracking can be achieved with labelled ligands either in vivo or ex vivo e.g. by flow cytometry or histochemistry on cells or tissues. In vivo application of ligands specific for either the transferred cells or the host cells enables selectively depleting either the transferred cells or the host cells using the antibody that only binds to the transferred, engineered cells or the host cells, respectively. Alternatively, selective cell depletion could be achieved by cells carrying a natural or a chimeric antigen receptor (CAR) recognizing either the transferred cells or the host cells. The nucleotide sequence encoding such a CAR can be derived from the hybridoma cells producing the ligands recognizing the specific isoforms.

Selective depletion of the engineered cells constitutes an important safety feature by providing a "safety switch". The basic concept of safety switches and suicide genes is described in Jones et al., Front Pharmacol.; 5:254. doi: 10.3389. The approach of the inventors is simpler, safer and more versatile. In principle any cell which is adoptively transferred can be engineered to carry the altered allele/epitope as a combined in vitro or in vivo selection, tracking, safety and/or selective ablation switch. Non-exclusive examples include cells which only carry the engineered allele but are otherwise not genetically engineered or cells which carry additionally engineered features such as CAR cells. For instance, transferred allogeneic cells which are used for their graft vs leukemia effect can cause graft vs host disease (GvHD). If the engineered allele is incorporated before transfer they can be eliminated by the engineered allele to reduce/treat GvHD. Similarly, transferred autologous tumor infiltrating lymphocytes (TILs) or pathogen-specific lymphocytes can be engineered to carry the altered allele to eliminate them if unwanted side-effects occur due to off-target effects or too intense on-target effects. In the case of CAR cells the altered allele can serve as a safety switch. Moreover, transferred, engineered cells can also be eliminated in case they become malignant or cause any type of unwanted on-target or off-target damage. Alternatively, disease causing host cells can be selectively ablated while sparing autologous but engineered cells. In contrast to the inventors' method existing technology is restricted to ablation of the transferred cells but does not easily allow ablation of host cells. The altered isoform allows to transfer e.g. gene-repaired or otherwise engineered autologous cells during ablation of host cells. Without the isoform switch introduced by the method of the invention, the host cell ablation needs to be stopped when the healthy cells are transferred. In this case, while the newly transferred, repaired cells expand the host cells will also expand and can no longer be ablated, risking that the disease-causing host cells will outcompete the repaired cells. Therefore rendering the engineered cells resistant to depletion by the method of the invention is highly relevant as a therapeutic approach. As an example, the CD19 epitope recognized by anti-CD19-CAR cells could be mutated in autologous hematopoietic cells such that depleting anti-CD19 mAb or anti-CDl9-CAR cells no longer can bind and destroy the engineered cells but CD19 would remain functional. This would eliminate a major complication of today's effective anti-CD19-CAR cells. While anti-CD19-CAR have very high success rates eliminating CD19 expressing hematopoietic malignomas they concordantly lead to eliminating of CD19 expressing healthy host ceils. This leads to hypogammaglobulinemia and therefore increased risk for infections. A mutated CD19 would allow reconstitution of the host immune system with healthy autologous hematopoietic stem cells (HSCs), which will give rise to B cells which are resistant to the anti-CD19-CAR cells. The CAR 19 T cells might therefore continuously prevent a relapse while the edited resistant cells will provide natural protection from infections. Patients would therefore no longer depend on IVIG infusions. HSC transplantation could potentially be achieved as partial chimerism through non-genotoxic preconditioning, e.g. through antibodies (Nat Biotech, 2016). Alternatively, anti-CD45-CAR cells recognizing a natural CD45 epitope (e.g. CD45.2) could be used to eliminate all hematopoietic host cells including malignant or otherwise disease-causing hematopoietic cells. Transplantation of healthy autologous hematopoietic stem cells (HSCs) or other hematopoietic cells carrying an engineered CD45 epitope (e.g. CD45.1) as illustrated by the CD45.2 to CD45.1 switch experiments would allow to reconstitute the host with a healthy hematopoietic system which will no longer be depleted by the anti-CD45-CAR cells. A major advantage would be that all CD45 expressing malignancies (including but not restricted to T cell and myeloid malignancies) can be targeted without the need for tumor- or cell type-specific antigens, i.e. the invention would provide a universally applicable system to treat hematopoietic malignancies and other non-malignant hematopoietic diseases. In addition, hematopoietic tumors could be treated without the need for allogeneic cells therefore eliminating GvHD as a major complication. Moreover, reconstitution can start during the depletion phase, which will shorten time to recovery. Importantly, the mutation used to render the transferred cells resistant to depletion can later also be used to deplete those cells again should this become necessary. CAR cell dependent depletion of HSCs could potentially be used as an alternative way of achieving mild, i.e. non-genotoxic preconditioning. CAR cells directed against an antigen or a combination of antigens to restrict the target cells specifically to HSCs could be used to deplete endogenous HSCs. This could be e.

g. anti-CD45 or anti-CD34 plus a second antigen in a synthetic biology approach (e.g. with an AND gate) to specifically and exclusively direct the CAR ceils against HSCs.

This aspect of the invention represents a universal strategy to replace cells. The cells may be hematopoietic cells, autologous or allogeneic. If the replacing cells are HSCs, the described method can be used to treat any hematopoietic malignancy or other hematopoietic disorders.

Other advantages of the approach of the inventors compared to existing "safety switch" approaches include the following. The inventors' approach uses an endogenous protein. No transgene or tag has to be introduced into the cell. The two epitopes are functionally identical, but can be distinguished by specifically binding ligands. The approach enables both depletion of transferred cells or host cells, depending which ligand is used. Since the designed mutation is introduced into the genome the safety feature remains permanently in the cells and will not get silenced which can happen to virally introduced transgenic safety switches. In addition, the engineered epitope will be less antigenic than artificial large safety switch/suicide gene constructs and will therefore less likely be rejected by host cells. Moreover, the use of engineered isoforms relies on targeted mutations and is therefore likely safer than other safety switches/suicide genes which are randomly integrated into the genome, usually by viral delivery and can therefore lead to insertional mutagenesis (Cornu, Nat Med, 2017).

The skilled person is aware that in order to change the cell surface protein from the first isoform to the second isoform, alternative methods can be applied instead of HDR. Byway of non-limiting example, the isoform switch can be effected using base editors as described by way of non-limiting example in the following publication: Komor et al., Nature 533, 420-424, doi:10.1038/nature17946. This approach could increase the safety even further by allowing editing of the desired amino acid without the need for a dsDNA break. Base editors or related technologies can be delivered as plasmids or minicircles (dsDNA), mRNA or RNP.

In instances where the switching of a first isoform of a cell surface protein to a second isoform is combined with the repair of a disease causing gene by the method of the invention (e.g. the Foxp3 gene), it is possible to deplete the non-repaired cells in vivo (i.e. after transfer into the host) by depleting the cells expressing the first isoform. The inventors have demonstrated that the likelihood of a successfully repaired gene is increased in cells in which the isoform switch has occurred. Combining an isoform switch at a first gene with a genetic modification at a second gene allows to include a safety feature into genetically engineered cells.

The isoform switch can also be employed as a marker to trace edited, transferred cells in a host. According to an alternative of this aspect of the invention, a method for selectively depleting or enriching a cell in a composition of non-edited and edited cells is provided, wherein the method comprises the steps of
  a. providing a cell, wherein the cell expresses a first isoform of a surface protein, which is different from a second isoform of the surface protein with regard to an amino acid marker, wherein the first isoform comprises amino acid marker A encoded by nucleic acid sequence A, and the second isoform comprises amino acid marker B encoded by nucleic acid sequence B;
  b. inducing in said cell by site specific genetic manipulation the exchange of nucleic acid sequence A to nucleic acid sequence B, thereby changing in said cell the expression of the first isoform to the expression of the second isoform;
  c. selectively enriching/depleting the cell based on the expression of the first or the second isoform of the surface protein.

In certain embodiments of this alternative aspect, the genetic manipulation is effected by providing, in particular transfecting said cell with, a base editor (as described in Komor et al., Nature 533, 420-424, doi:10.1038/nature17946) capable of changing nucleic acid sequence A, encoding amino acid marker A, to nucleic acid sequence B, encoding amino acid marker B, and a guide RNA capable of directing said base editor to nucleic acid sequence A, encoding amino acid marker A.

According to another aspect of the invention, a kit comprising the following components is provided:
  a. A guide RNA targeting a genomic location of a gene encoding a cell surface protein, wherein said gene exists in two isoforms that differ with regard to a nucleic acid marker sequence, wherein isoform 1 comprises a first marker sequence and isoform 2 comprises a second marker sequence. The genomic location comprises a PAM sequence and said first or second marker sequence.
  b. A DNA construct comprising said first marker sequence or said second marker sequence, said PAM sequence, wherein in particular said PAM sequence is mutated and non-functional and a pair of homology arms homologous to the genomic DNA sequences 5' and 3' of said genomic location of the gene encoding said cell surface protein.
  c. Optionally a first and a second antibody that bind specifically to the gene products of isoform 1 and isoform 2, respectively.

The kit enables to transform isoform 1 into isoform 2 or to transform isoform 2 into isoform 1. The expression "DNA construct comprising said first marker sequence or said second marker sequence" refers to a construct comprising either the first marker sequence or the second marker sequence, wherein user of the kit is aware which marker sequence it is. If the kit comprises both constructs, these constructed are physically separated (e.g. in different tubes) and labelled accordingly.

In certain embodiments of this aspect of the invention, the kit comprises HDR enhancing reagents, in particular vanillin and/or rucaparib.

In certain embodiments of this aspect of the invention, the homology arms comprise at least 85 basepairs (bp) each, more particularly at least 450 bp each, even more particularly approx. 2000 bp each. In certain embodiments of this aspect of the invention, the homology arms comprise at least 2000 bp each. The inventors have shown that an increased length of the homology arms increases HDR efficiency (FIG. 4D). If longer templates are used, the amount of HDR enhancing reagent may be reduced. This is desirable in order to minimize possible side effects of HDR enhancing reagents in clinical applications. In certain instances long arms of homology may be more efficient and more desirable than HDR enhancing compounds in others the use of shorter templates, e.g. ssDNA templates combined with HDR enhancing molecules may be more desirable. The inventors have also shown that an increased length of the homology arms enables HDR in instances where distance between the induced DNA break and the mutation site is more than 50 bp (e.g. in instances where it is not possible to design a sgRNA within 50 bp of the mutation site due to sequence limitations) (FIG. 4H). This is an important and surprising finding, as others have described that it is not possible to achieve HDR if the distance between the induced DNA break and the mutation site is more than 50 bp (Paquet et al, Nature. 2016 May 5; 533(7601):125-9). Longer templates can also overcome the need to mutate the PAM sequence in cases where silent mutations are not possible.

In certain embodiments of this aspect of the invention, the cell surface protein is a human cell surface protein.

In certain embodiments of this aspect of the invention, the cell surface protein is murine Thy1 or murine CD45.

In certain embodiments of this aspect of the invention, the cell surface protein is murine Thy1, the guide RNA is SEQ ID NO 001 and said DNA construct is selected from SEQ ID NO 013 (no mut), SEQ ID NO 014 (mut), SEQ ID NO 015 (4×mut), SEQ ID NO 024 (2 kb), SEQ ID NO 025 (4 kb), SEQ ID NO 026 (1 kb) and SEQ ID NO 027 (160 bp).

In certain embodiments of this aspect of the invention, the cell surface protein is murine Thy1, the guide RNA is SEQ ID NO 008 and said DNA construct is selected from SEQ ID NO 017 (120 bp) and SEQ ID NO 018 (180 bp).

In certain embodiments of this aspect of the invention, the cell surface protein is murine CD45, the guide RNA is SEQ ID NO 003 and said DNA construct is selected from SEQ ID NO 009, SEQ ID NO 019 (1 kb), SEQ ID NO 020 (2 kb) and SEQ ID NO 021 (4 kb).

In certain embodiments of this aspect of the invention, the kit additionally comprises a murine T cell line that has been genetically engineered for stable Cas9 expression. The inventors have established such a T cell line (EL-4 ATCC TIB-39) with stable Cas9 expression (FIG. 8). An advantage of using a cell with stable Cas9 expression is that the amount of DNA that has to be transfected is reduced, which increases cell survival and can increase HDR efficiency. In these cells, only guide RNA and DNA repair construct have to be transfected.

According to another aspect, a method for editing a genomic location of interest in a hematopoietic cell is provided. The method comprises the following steps:
a. Providing a hematopoietic cell.
b. Culturing said hematopoietic cell in presence of a factor capable of activating said hematopoietic cell in a first culture step.
c. Transfecting the hematopoietic cell with
  i. a DNA expression construct encoding a CRISPR-associated endonuclease, a first marker gene and a guide RNA, wherein the guide RNA is capable of annealing to the genomic location of interest; and
  ii. a DNA repair construct, wherein the DNA repair construct comprises a transgenic DNA sequence of interest (to be inserted into the genomic DNA) and homology arms that are homologous to the genomic DNA sequences 5' and 3' of the genomic location of interest.
d. Culturing said hematopoietic cell in presence of a factor capable of activating said hematopoietic cell in a first culture step.
e. Isolating hematopoietic cells expressing the first marker gene in an isolation step.
f. Culturing the isolated hematopoietic cells in a third culture step, wherein the third culture step comprises the treatment of the hematopoietic cells with homology directed repair (HDR) enhancing reagents.

In the context of the present specification, the expression "DNA expression construct" may refer to a single DNA construct comprising CRISPR-associated endonuclease, marker gene and guide RNA, or to multiple DNA constructs comprising the components. An advantage of having all three components on one construct is that all cells that are positive for the marker gene are also positive for the other components. The skilled person is aware that the guide RNA may alternatively be provided in the form of in vitro transcribed guide RNA and that the endonuclease may alternatively be provided as mRNA or as a protein. Endonuclease and guide RNA may also be provided in combination in the form of ribonucleoprotein particles (RNPs). If the DNA expression construct comprises a marker gene, in particular a gene encoding a fluorescent protein, it can be used to identify cells that have taken up the DNA expression construct.

It has been reported that gene editing in primary cells requires the use of RNPs (Schumann et al., 2015, PNAS). It is also commonly reported that in cells of the blood and immune system the transfer of naked DNA by electroporation can lead to massive cell death owing to the activation of intrinsic cellular-defense mechanisms (Cornu, Nat Med, 2017). Surprisingly, the inventors were able to achieve electroporation and gene editing including HDR in primary T cells using a DNA expression construct comprising Cas9, guide RNA and GFP).

The cellular response to a DNA double strand break is the activation of the DNA repair machinery which mainly consists of the NHEJ pathway and the HDR pathway. NHEJ usually results in random insertions and deletions (indels) which can be exploited to delete genes. This can be useful for experimental purposes, but for clinical use the inherently stochastic NHEJ repair pathway bears significant risks. Blocking the NHEJ pathway results in a shift of the cellular response towards the HDR pathway.

In certain embodiments of this aspect of the invention, the homology arms of the DNA repair construct comprise approximately 2000 basepairs (bp) each. In certain embodiments, the homology arms comprise at least 2000 bp each. The inventors have shown that an increased length of the homology arms increases HDR efficiency (FIG. 4D). If longer templates are used, the amount of HDR enhancing reagent may be reduced. This is desirable in order to minimize possible side effects of HDR enhancing reagents in clinical applications. In certain instances long arms of homology may be more efficient and more desirable than HDR enhancing compounds in others the use of shorter templates, e.g. ssDNA templates combined with HDR enhancing molecules may be more desirable. The inventors have also shown that an increased length of the homology arms enables HDR in instances where distance between the induced DNA break and the mutation site is more than 50 bp (e.g. in instances where it is not possible to design a sgRNA within 50 bp of the mutation site due to sequence limitations) (FIG. 4H). This is an important and surprising finding, as others have described that it is not possible to achieve HDR if the distance between the induced DNA break and the mutation site is more than 50 bp (Paquet et al, Nature. 2016 May 5; 533(7601):125-9). Longer templates can also overcome the need to mutate the PAM sequence in cases where silent mutations are not possible.

DNA cleavage by Cas9 is dependent on the presence of a short protospacer adjacent motif (PAM) in the target DNA, restricting the choice of targetable sequences. CAS9 from *Streptococcus pyogenes* (SpyCas9) for example corresponds to the PAM sequence 5'-NGG-3'. In certain embodiments, the DNA repair construct comprises a mutated PAM sequence. The mutation renders the PAM sequence non-functional but does not affect protein expression, stability or function. The use of a DNA repair construct comprising a mutated PAM sequence enhances HDR efficiency (FIG. 3D).

In instances where no DNA repair construct is provided, DNA double strand breaks are predominantly repaired via the NHEJ pathway.

HDR enhancing reagents can be used to shift the cellular response towards the HDR pathway.

Commonly used HDR enhancing reagents are SCR7 (a ligase IV inhibitor) (Singh et al., 2014, Genetics) and RS-1 (Song et al., 2016, Nat Communications). There is an unmet need for additional reagents that are able to increase HDR efficiency. The general strategy of using small molecules to inhibit NHEJ and thus enhance HDR has been contemplated. The choice however of an individual molecule and the optimal conditions as presented in the current specification were never contemplated or suggested in the art.

In certain embodiments of this aspect of the invention, the HDR enhancing reagent is selected from the group comprising vanillin and rucaparib. Vanillin and its derivatives have been previously suggested to inhibit the NHEJ pathway (Durant and Karan, 2003, Nucleic Acids Research, Vol. 31, No. 19 5501-5512). The inventors have systematically tested the effect of vanillin and other HDR enhancing reagents on HDR efficiency (FIG. 1C, FIG. 2F) and have surprisingly found that vanillin indeed increases HDR efficiency, while its derivatives do not. An advantage of vanillin compared to other HDR enhancing reagents is the fact that it is water soluble. Other HDR enhancing components require DMSO for solvation in aqueous media.

Within the context of the present specification, vanillin refers to 4-Hydroxy-3-methoxybenzaldehyde, CAS No. 121-33-5.

Within the context of the present specification, rucaparib refers to 8-Fluoro-2-{4-[(methylamino)methyl]phenyl}-1,3,4,5-tetrahydro-6H-azepino[5,4,3-cd]indol-6-one, CAS No. 283173-50-2.

In certain embodiments of this aspect of the invention, the HDR enhancing reagents are vanillin and/or rucaparib. In certain embodiments, the HDR enhancing reagents are vanillin at a concentration of 50 pM to 500 pM and/or rucaparib at a concentration of 0.5 pM to 2.5 pM. In certain embodiments, the HDR enhancing reagents are vanillin at a concentration of approx. 300 pM and/or rucaparib at a concentration of approx. 1 pM.

In certain embodiments of this aspect of the invention, the hematopoietic cell is selected from the group comprising a hematopoietic stem cell (hemocytoblast), a CD4+ T cell, a CD8+ T cell, a memory T cell, a regulatory T cell (T reg), a natural killer cell (NK), an innate lymphoid cell (ILC), a dendritic cell (DC), a B-lymphocyte, a mucosal-associated invariant T cell (MAIT) and a gamma delta T cell (y6 T).

In certain embodiments of this aspect of the invention, the first and said second culture step comprise contacting said hematopoietic cell with activating monoclonal antibodies anti-CD3 and anti-CD28. The antibodies may be soluble or immobilized, in particular on culture dishes, beads, or artificial antigen presenting cells (APCs).

In certain embodiments of this aspect of the invention, the method according to any one of the above claims, wherein said transfection can be achieved by electroporation, transfection using liposomes and/or exosomes, ballistic transfer, transfection using nanowires, cell squeezing techniques, osmotic shock, viral delivery or sonoporation.

In certain embodiments of this aspect of the invention, the isolation step comprises isolation of cells by flow cytometry or magnetic bead isolation.

In certain embodiments of this aspect of the invention, the treatment with HDR enhancing reagents lasts 22 to 26 hours, particularly 24 hours. After the treatment, cells are washed to remove the HDR enhancing reagents.

In certain embodiments of this aspect of the invention, the DNA expression construct is a minicircle plasmid. Within the context of the present specification, the term "minicircle plasmid" refers to a small circular plasmid derivative that has been freed from all prokaryotic vector parts.

In certain embodiments of this aspect of the invention, the first and second culture step last 18 hours to 36 hours, particularly 22 to 26 hours, more particularly 24 hours.

In certain embodiments of this aspect of the invention, the third culture step lasts 5 to 10 days, particularly 6 to 8 days, more particularly 7 days.

In certain embodiments of this aspect of the invention, the first marker gene encodes a fluorescent protein, particularly green fluorescent protein (GFP).

In certain embodiments of this aspect of the invention, the first marker gene encodes a protein expressed at the cell surface, wherein said protein expressed at the cell surface can be detected using a ligand specifically binding to said protein.

The method according to any one of the above claims, wherein said DNA repair construct is linked to an expression cassette encoding a second marker gene, and hematopoietic cells expressing said first and said second marker gene are isolated in said isolation step. Said second marker gene may encode a fluorescent protein or a protein expressed at the cell surface, wherein said protein expressed at the cell surface can be detected using a ligand specifically binding to said protein. The protein encoded by said first marker gene is different from said protein encoded by said second marker gene. The skilled person is aware that providing a "DNA repair construct linked to an expression cassette encoding a second marker gene" can be achieved by providing a DNA plasmid comprising both the DNA repair construct and the an expression cassette encoding a second marker gene.

In certain embodiments of this aspect of the invention, the hematopoietic cell is a T cell.

In certain embodiments of this aspect of the invention, the isolation step comprises isolation of said T cells in the blasting stage. The inventors have shown that HDR efficiency is higher in cells that are in the blasting stage than in cells that are not in the blasting stage (FIG. 2E and FIG. 3E). Thus, isolating cells in the blasting stage can increase the HDR efficiency.

In certain embodiments of this aspect of the invention, the T cell is a naive murine T cell, particularly a naive murine CD4+ T cell. The skilled person is aware that this embodiment refers to a T cell that is naive before the method according to the invention is performed. Afterwards, it can no longer be considered naive.

In certain embodiments of this aspect of the invention, the T cell is a naive human T cell. The skilled person is aware that this embodiment refers to a T cell that is naive before the method according to the invention is performed. Afterwards, it can no longer be considered naive.

According to another aspect of the invention, a hematopoietic cell in which a genomic location of interest has been edited using the method according to any one of the above claims is provided for use in a method of therapy or prevention of a disease.

In certain embodiments of this aspect of the invention, the hematopoietic cell is a T cell.

In certain embodiments of this aspect of the invention, the disease is immunodysregulation polyendocrinopathy enteropathy X-linked syndrome (IPEX; OMIM http://www.omim.org/entry/304790) or an IPEX-like syndrome and said genomic location is a mutation comprised in a gene selected from the Foxp3 gene, the CD25 gene, the StatSb gene, the Stat1 gene and the Itch gene (Verbsky and Chatila, Curr Opin Pediatr. 2013 December; 25(6):708-14). The mutations in said genes prevent the expression or normal function of the gene product. Editing these genomic locatione according to the method of the invention eliminates the mutation and thus restores the gene and the protein expression.

In certain embodiments of this aspect of the invention, the genomic location is a mutation comprised in the Foxp3 gene and said disease is immunodysregulation polyendocrinopathy enteropathy X-linked syndrome. In certain embodiments of this aspect of the invention, the genomic location is the Foxp3$^{K276X}$ mutation. The mutation in the Foxp3 gene prevents the normal function of the gene product. Editing this genomic location according to the method of the invention eliminates the mutation and thus restores the Foxp3 gene and Foxp3 protein expression.

In certain embodiments of this aspect of the invention, the hematopoietic cell is a murine T cell and the genomic location is the Foxp3$^{K276X}$ mutation. This mutation recapitulates a clinically relevant human Foxp3 mutation (Ramsdell et al., Nature reviews. Immunology 14, 343-349 (2014); Lin et al., The Journal of allergy and clinical immunology 116, 1106-1115 (2005)).

Within the context of the present specification, the term "Foxp3 gene" relates to human forkhead box P3, NCBI GENE ID: 50943 or murine forkhead box P3, NCBI GENE ID:20371.

The inventors have shown that it is possible to correct the Foxp3$^{K276X}$ mutation in murine T cells using the method according to the invention (FIG. 4).

In certain embodiments of this aspect of the invention, the genomic location is a mutation comprised in the CTLA-4 gene and the disease is human immune dysregulatory syndrome associated with CTLA-4 mutations (Schubert et al., Science Translational Medicine 5, 215ra174-215ra174 (2013); Kuehn et al., Science (New York, N.Y.) 345, 1623-1627 (2014)).

In certain embodiments of this aspect of the invention, the therapy or prevention of a disease is effected by adoptive transfer of cells which have been edited by a method according to the invention, in particular adoptive transfer of cells in which a genetic defect has been corrected by a method according to the invention.

Adoptive cell therapy has for a long time successfully been used in platelet and erythrocyte transfusions and hematopoietic stem cell transplantation. More recently, adoptive lymphocyte transfer demonstrated clinical efficacy in various disease settings and thus constitutes a promising expansion of applications as a treatment for infections, inflammatory and autoimmune diseases, organ transplantation as well as cancer. It has been proposed that cell-based therapeutics constitute the next "pillar" of medicine. Targeted modifications effected by the method according to the invention allow to customize the transferred cell product to repair genetic defects, increase the efficiency of the transferred cells or equip the cells with additional desired features such as guidance molecules or safety switches. The current invention provides an efficient, reliable and inexpensive method for precise gene editing in hematopoietic cells.

According to another aspect of the invention, rucaparib is provided as HDR enhancing reagent. In certain embodiments of this aspect of the invention, rucaparib is applied at a concentration of 0.5 pM to 2.5 pM, particularly approx. 1 pM. In certain embodiments of this aspect of the invention, rucaparib is applied together with vanillin, in particular together with 50 pM to 500 pM vanillin.

According to another aspect of the invention, a method for high resolution epitope mapping is provided. Said method comprises the following steps:

a. Providing a cell expressing a gene product capable of binding to a ligand. One or several marker comprised in said gene product determine the binding to said ligand and in combination comprise an epitope. The one or several marker may be in linear or non-linear sequence. The gene product is encoded by a nucleotide sequence comprised in the genomic DNA of the cell, and the epitope is encoded by one or several original epitope encoding sequences comprised in the nucleotide sequence.

b. Inducing a double strand break in the coding sequence location by transfecting the cell with a DNA expression construct encoding a CRISPR-associated endonuclease (Cas9) and a guide RNA targeting the original epitope encoding sequence.

c. Providing a DNA repair construct within the cell. The DNA repair construct comprises a transgenic epitope encoding sequence different from said original epitope encoding sequence and a pair of homology arms homologous to the genomic DNA sequences 5' and 3' of the original epitope encoding sequence.

By performing the aforementioned steps, a homology directed repair (HDR) event is induced in the cell, whereby a mutant of the gene product is expressed in the cell.

d. Subsequently, it is assessed whether the mutant is capable of binding to the ligand.

Said (one or several) markers may be amino acids (in instances where the gene product is a polypeptide) or nucleic acids. Said (one or several) markers may comprise carbohydrates, lipids or combinations of proteins and sugars, lipids and other molecules—such as observed in posttranslational modifications or non-classical antigens—attached to said marker amino acids or marker nucleic acids.

Within the context of the present specification, the term "epitope mapping" refers to the process of experimentally identifying and characterizing the binding sites (epitopes) of a ligand that are present on a gene product. The process comprises systematic generation of several variants of a gene product comprising several different epitope variants and systematic testing of the binding of the ligand to the gene product. The method according to the invention allows for the precise characterization of epitopes by mutating single amino acids. The method also allows for ablation of known or suspected epitopes by deletion or mutation of single amino acids. This way, it can be analysed if certain amino acids are necessary and/or sufficient for ligand binding.

Knowing the precise epitope for a given ligand can be important for various reasons: a) optimization of existing ligands, e.g. therapeutic antibodies or chimeric antigen receptors (CARs) b) protection of intellectual property, e.g. a therapeutic antibody c) to determine freedom to operate. Ideally, the protein that is mapped for epitopes should contain all endogenous posttranslational modifications. This is possible by the method of the current invention, which is a cell based assay. Existing assays for epitope mapping have major limitations: the cells used are most likely not the target cells of interest and the candidate epitopes may be expressed as peptides or transgenes and therefore their copy number and expression level most likely is not physiologic and posttranslational modifications may differ. The present invention provides a method for epitope mapping of antigens that are 18 physiologically expressed in a cell of interest, e.g. in a target tumour cell, and comprise all posttranslational modifications In the context of the present specification, the expression "ligand" refers to any molecule capable of specific binding (with a dissociation constant<10 E-7) to a gene product. In the context of the invention, the "gene product" is edited by the inventive method, and binding of a molecule (ligand) to this gene product is tested. The molecule (ligand) can be selected from protein, RNA or even DNA. Thus, the method according to the invention allows to map protein-protein interactions, protein-RNA interactions and protein-DNA interactions.

The skilled person is aware that the expression "guide RNA targeting the original epitope encoding sequence" refers to a guide RNA effecting a DSB directly at the epitope encoding sequence, up to 20 bp in 5' or 3' direction of the epitope encoding sequence or even up to 50 bp in 5' or 3' direction of the epitope encoding sequence.

In instances where this is not feasible to design a guide RNA that directly targets the epitope encoding sequence (due to the requirements of guide RNA design), a guide RNA targeting a sequence up to 20 bp (up to 50 bp) in 5' or 3' direction of the epitope encoding sequence may be used. With a distance greater than 20 bp, the HDR efficiency decreases significantly.

In certain embodiments of this aspect of the invention, the homology arms of the DNA repair construct comprise approximately 2000 basepairs (bp) each. In certain embodiments, the homology arms comprise at least 2000 bp each. The inventors have shown that an increased length of the homology arms increases HDR efficiency (FIG. 4D). If longer templates are used, the amount of HDR enhancing reagent may be reduced. This is desirable in order to minimize possible side effects of HDR enhancing reagents in clinical applications. In certain instances long arms of homology may be more efficient and more desirable than HDR enhancing compounds in others the use of shorter templates, e. g. ssDNA templates combined with HDR enhancing molecules may be more desirable. The inventors have also shown that an increased length of the homology arms enables HDR in instances where distance between the induced DNA break and the mutation site is more than 50 bp (e.g. in instances where it is not possible to design a sgRNA within 50 bp of the mutation site due to sequence limitations) (FIG. 4H). This is an important and surprising finding, as others have described that it is not possible to achieve HDR if the distance between the induced DNA break and the mutation site is more than 50 bp (Paquet et al, Nature. 2016 May 5; 533(7601):125-9). Longer templates can also overcome the need to mutate the PAM sequence in cases where silent mutations are not possible.

Importantly, the method according to the invention allows epitope mapping in cells that endogenously express the gene product of interest, without the need for overexpression. This enables characterization of the epitopes in full-length proteins comprising all posttranslational modifications.

In the context of the present specification, the term "antigen" refers a molecule that is specifically recognized by and bound by a ligand. Antigens can be proteins, posttranslationally modified proteins, lipids or sugars presented in the context of a protein. In the context of epitopes recognized by antibodies or antibody-derived ligands (such as Fab fragments or chimeric antigen receptors) the antigenic determinant can be any structure specifically recognized by the ligand.

The CRISPR associated endonuclease can be provided as DNA or mRNA (encoding the enodonuclease) or as protein. The guide RNA can be provided as DNA (encoding the guide RNA) or as in vitro synthesized RNA. Endonuclease and guide RNA may also be provided in combination in the form of ribonucleoprotein particles (RNPs).

The cellular response to a DNA double strand break is the activation of the DNA repair machinery which mainly consists of the non-homologous end joining (NHEJ) pathway and the HDR pathway. During genomic DNA repair by HDR, the transgenic epitope encoding sequence is copied and inserted into the genomic DNA. The skilled person is aware that the DNA repair construct can be linear (single stranded or double stranded) or circular (e.g. plasmid, minicircle plasmid).

In certain embodiments of this aspect of the invention, no DNA repair construct is provided and DNA repair is achieved via the NHEJ pathway. In some instances this does not abolish expression of the gene product but leads to the expression of a mutated gene product. In these instances, it can be assessed whether the mutant is capable of binding to the ligand.

In certain embodiments of this aspect of the invention, the cell is a eukaryotic cell.

In certain embodiments of this aspect of the invention, the gene product is a polypeptide. In instances where the gene product is a polypeptide, the ligand may be (by way of non-limiting examples) a soluble or membrane-bound antigen receptor of an immune cell, a natural or artificial derivative of an antigen receptor, a B cell antigen receptor (immunoglobulin) or a T cell receptor. The ligand may also be a cell carrying any type of antigen receptor, natural or artificial.

In certain embodiments of this aspect of the invention, the cell carrying the epitope of interest is a physiologically occurring cell, or in other words a healthy cell. In certain embodiments, the cell carrying the epitope of interest may be in a diseased state such as a tumour cell or the cell carrying the antigen may be a synthetic cell carrying designer antigens or any combination thereof. The gene product may be a naturally occurring antigen, an altered antigen including a tumour antigen or an artificially altered or synthesized antigen. In these instances, possible applications are high resolution mapping of the precise binding site of a ligand to an altered tumour antigen.

In personalized tumour therapy, a patients tumour cells may be used to characterize the tumour antigens and to identify the epitopes which best bind to available therapeutic antibodies. Tumour cells from patients could be isolated and then be immortalized to be used for epitope mapping. This information could in turn be used to optimize the ligand itself, either through directed mutagenesis or through mutagenesis of the antigen binding regions of the ligand using a procedure analogous to the one disclosed here. Rather than changing the epitope the ligand itself could be altered to increase the affinity between antigen and ligand. The same procedure could be used to characterize the epitopes of tumour cells which escaped tumour therapy through modification of its antigens. This information could then be used to engineer ligands which are able to recognize the therapy-resistant tumour cells.

In certain embodiments of this aspect of the invention, the gene product is a chimeric antigen receptor (CAR). Within the context of the present specification, the term "chimeric antigen receptor" refers to an engineered receptor comprising domains of T cell receptors and B cell receptors. CARs recognize a wide range of antigens comprising proteins, lipids and sugars. In instances where the gene product is a CAR, the ligand is the respective antigen.

In certain embodiments of this aspect of the invention, the gene product is an antibody (B cell receptor, immunoglobulin). This way, the exact regions of a B cell receptor necessary to bind to a given antigen can be determined. Using this information, the binding properties of the receptor can be engineered, e.g. binding affinity of the antibody could be increased.

In certain embodiments of this aspect of the invention, the gene product is a T cell receptor.

In certain embodiments of this aspect of the invention, the ligand is a polypeptide.

In certain embodiments of this aspect of the invention, the ligand is an antigen receptor. For assessing the binding of the mutant gene product to a specific antigen receptor (antibody), a polyclonal antibody recognizing more than one epitope of the gene product can be used as positive control.

In certain embodiments of this aspect of the invention, the ligand is a T cell receptor (TCR). In such cases an entire T cell or other cell carrying the T cell receptor may be used to probe the TCR/antigen interaction.

In certain embodiments of this aspect of the invention, the ligand is a chimeric antigen receptor (CAR).

In certain embodiments of this aspect of the invention, the homology arms comprise at least 85 basepairs (bp) each. In certain embodiments, the homology arms comprise at least 450 bp each. In certain embodiments, the homology arms comprise approx. 2000 bp each. In certain embodiments, the homology arms at least 2000 bp each. The inventors have shown that an increased length of the homology arms increases HDR efficiency (FIG. 4D). If longer templates are used, the amount of HDR enhancing reagent may be reduced. This is desirable in order to minimize possible side effects of HDR enhancing reagents in clinical applications. In certain instances long arms of homology may be more efficient and more desirable than HDR enhancing compounds in others the use of shorter templates, e.g. ssDNA templates combined with HDR enhancing molecules may be more desirable. The inventors have also shown that an increased length of the homology arms enables HDR in instances where distance between the induced DNA break and the mutation site is more than 50 bp (e.g. in instances where it is not possible to design a sgRNA within 50 bp of the mutation site due to sequence limitations) (FIG. 4H). This is an important and surprising finding, as others have described that it is not possible to achieve HDR if the distance between the induced DNA break and the mutation site is more than 50 bp (Paquet et al, Nature. 2016 May 5; 533(7601):125-9). Longer templates can also overcome the need to mutate the PAM sequence in cases where silent mutations are not possible.

In certain embodiments of this aspect of the invention, in a first screening step, the method according to the invention is performed using short homology arms (at least 85 bp) and HDR enhancing reagents. In a second validation step, the method according to the invention is performed using long homology arms (approx. 2000 bp or longer) in and no HDR enhancing reagents.

In certain embodiments of this aspect of the invention, the cell is kept in a cell culture medium comprising a HDR enhancing reagent for 22 to 26 hours, particularly approx. 24 hours subsequently to step c.

Optimized methods including optimization of various parameters for in vivo HDR-mediated epitope mapping can be applied (FIG. 3).

In certain embodiments of this aspect of the invention, the HDR enhancing reagent is selected from the group comprising vanillin, rucaparib, velaparib, luminespib, L75507, SCR7 and RS-1.

In certain embodiments of this aspect of the invention, the HDR enhancing reagent is vanillin and/or rucaparib. In certain embodiments, the HDR enhancing reagent is vanillin at a concentration of 50 pM to 500 pM and/or rucaparib at a concentration of 0.5 pM to 2.5 pM. In certain embodiments, the HDR enhancing reagent is vanillin at a concentration of approx. 300 pM and/or rucaparib at a concentration of approx. 1 pM.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

Figure 1A:
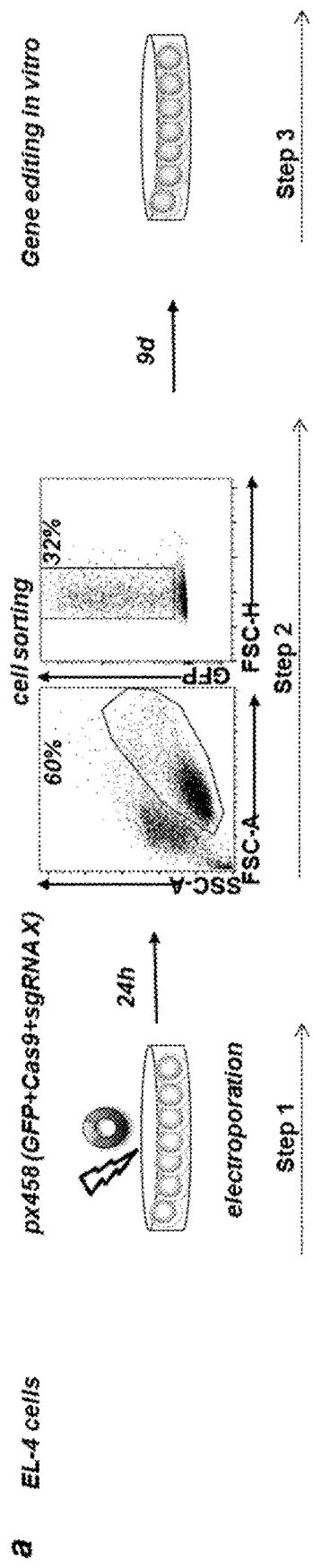
FIG. 1 shows efficient plasmid-based gene ablation in primary T cells.

A) Protocol for plasmid-based gene editing in EL-4 cells. Electroporation of a plasmid encoding a sgRNA targeting the gene X, Cas9 and GFP (step 1). After 24 h successfully transfected cells are purified by flow cytometry based on GFP expression (step 2). Subsequent cell expansion for 9 days for gene editing in vitro (step 3). B) Protocol for plasmid-based gene editing in primary CD4+ T cells. Prior to electroporation cells are activated by anti-CD3 and anti-CD28 mAbs. After 24 h a plasmid encoding a sgRNA targeting the gene X, Cas9 and GFP is electroporated (step 1). 24 h later successfully transfected cells are purified based on GFP expression (step 2) and expanded for 9 days in vitro as shown (step 3). C) Flow cytometry of EL-4 cells transfected as in a, with plasmid encoding CD90.2 targeting sgRNA (sgRNA 90.2, SEQ ID NO 001) or empty vector px458 (control). Flow cytometry histograms (left panel) and quantification of multiple experiments (n=3); error bars represent standard deviation (SD) (right panel). D) Primary T cells transfected as in b, with plasmid encoding CD90.2 targeting sgRNA (sgRNA 90.2, SEQ ID NO 001) or empty vector (control). Flow cytometry histograms (left panel) and quantification of 2 experiments; error bars represent SD (right panel). E) Same conditions as in c but with CD45.2 targeting sgRNA (sgRNA 45.2, SEQ ID NO 003) or empty vector (control). Representative data from 3 experiments; error bars represent SD. F) Same conditions as in d but with CD45.2 targeting sgRNA (sgRNA 45.2, SEQ ID NO 003) or empty vector (control). Representative data from 3 experiments; error bars represent SD. G) EL-4 cells transfected as in a but with 2 plasmids encoding 2 sgRNAs targeting CD90.2 and CD45.2 simultaneously (sgRNA90.2 and sgRNA45.2, SEQ ID NO 001 and SEQ ID NO 003). Flow cytometry of cells transfected with empty px458 vector (left panel) or cells transfected with plasmids encoding sgRNAs targeting CD90.2 and CD45.2 (SEQ ID NO 001 and SEQ ID NO 003) (right panel). Representative data from 2 experiments; error bars represent SD. H) Primary CD4+ T cells transfected as in b, with CD90.2 targeting sgRNA (sgRNA 90.2, SEQ ID NO 001) or empty vector (control). Immediately after purification of GFP+ cells (step 2) $2 \times 10^5$ purified cells were injected i.v. in RAG KO recipients. 10 days later cells from SP and LN were harvested. Flow cytometry histograms for CD90.2 on live CD4+ T cells in LN and SP (left panel) and quantification of multiple recipients (right panel). Two experiments with a total of 6 recipients (right panel).

FIG. 2 shows targeted introduction of point mutations in primary T cells.

A) Bead-enriched naive CD4+ T cells from Balb/c mice were activated for 24 h and subsequently electroporated with empty px458 plasmid (control), with plasmid encoding CD90.1 targeting sgRNA (sgRNA CD90.1, SEQ ID NO 008) alone or sgRNA CD90.1 along with 3 different sizes of ssDNA CD90.2 templates (90 bp: SEQ ID NO 016, 120 bp: SEQ ID NO 017 and 180 bp: SEQ ID NO 018) respectively (step 1, supplementary FIG. 1a). 24 h post electroporation purification of GFP+ cells followed by in vitro culture of purified cells. Nine days later cell harvesting and flow cytometry for CD90.1 and CD90.2. Representative data from one experiment. B) Bead-enriched naive CD4+ T cells from C57B16/N mice activated and electroporated as in (a) but with plasmid encoding CD90.2 targeting sgRNA (sgRNA CD90.2, SEQ ID NO 001) and a 180 bp CD90.1 ssDNA template (SEQ ID NO 013). Cells were cultured for the next 24 h in vitro in order to allow GFP expression. Immediately after purification of GFP+ cells addition of DMSO (left panel) or the NHEJ inhibitor SCR7-X (purchased from XcessBio, for reference see Greco et al., DNA Repair (Amst). 2016 July; 43:18-23), for 24 h (right panel). Nine days later cell harvest and flow cytometry for CD90.2 and CD90.1. Representative data from one experiment. C) EL-4 cells electroporated with plasmid encoding CD90.2 targeting sgRNA (sgRNA CD90.2, SEQ ID NO 001) and a 180 bp CD90.1 ssDNA template (SEQ ID NO 013). Cells were cultured for the next 24 h in vitro in order to allow GFP expression. Immediately after purification of GFP+ cells addition of NHEJ inhibitors SCR7-X, vanillin or rucaparib for 24 h. Nine days in vitro expansion, then cell harvest and flow cytometry for CD90.2 and CD90.1 expression in untreated (left panel) and treated samples (right panels). Representative data from 3 experiments. D) EL-4 cells electroporated with plasmid encoding CD90.2 targeting sgRNA (sgRNA CD90.2, SEQ ID NO 001) and a circular plasmid including a CD90.1 dsDNA template of various length (160 bp: SEQ ID NO 027, 1 kb: SEQ ID NO 026, 2 kb: SEQ ID NO 024, 4 kb: SEQ ID NO 025). Cells were cultured for the next 24 h in vitro in order to allow GFP expression. Immediately after purification of GFP+ cells addition of vanillin (NHEJ inhibitor) for 24 h. Nine days in vitro expansion, then cell harvest and flow cytometry for CD90.2 and CD90.1. Representative flow cytometry plots (left panel) and quantification of multiple experiments of the average frequency of cells that underwent HDR (heterozygous and homozygous) (right panel). (Representative data from n=3 experiments; error bars represent SD). E) Bead-enriched naive CD4+ T cells from C57B16/N mice activated and electroporated with empty px458 plasmid or plasmid encoding CD90.2 targeting sgRNA (sgRNA CD90.2, SEQ ID NO 001) and a plasmid including a 1 kb CD90.1 dsDNA template (SEQ ID NO 026). Cells were cultured for the next 24 h in vitro in order to allow GFP expression. Immediately after purification of GFP+ cells addition of vanillin (NHEJ inhibitor) for 24 h. Nine days in vitro expansion, then cell harvest and flow cytometry for CD90.2 and CD90.1. Flow cytometry plots demonstrate gating on total live cells (left panels) and blasting cells (right panels). Representative data from 2 experiments. F) Quantification of the effect of vanillin on the relative enrichment of HDR frequency (fold change) as a function of dsDNA template length. Experiment as in D. Fold increase of HDR frequency of cells treated with vanillin relative to absence of vanillin for each template. (Representative data from n=3 experiments; error bars represent SD). G) Long templates without NHEJ inhibitor result in higher HDR frequency than short templates with NHEJ inhibitor. Quantification of HDR frequency obtained with short templates (160 bp, 1 kb) plus NHEJ inhibitor (vanillin) and long templates (2 kb, 4 kb) without NHEJ inhibitor. Experiment as in D. (Representative data from n=3 experiments; error bars represent SD). H) Effect of cut-to-mutation distance on HDR efficiency. Two CD90.2 targeting sgRNAs either covering the intended mutation (sgRNA CD90.2, SEQ ID NO 001) (upper panels) or located 50 bp away (sgRNA CD90.2-A, SEQ ID NO 002) (lower panels) were used to edit CD90.2 cells to CD90.1 cells. Experimental setup as in D. A cut-to-mutation distance of 50 bp abolishes HDR with short templates (160 bp, 1 kb). Longer templates (2 kb, 4 kb) overcome this limitation. (Representative data from n=3 experiments; error bars represent SD).

FIG. 3 shows the enrichment of HDR-edited cells through monitoring of isoform switching of a surrogate cell surface marker.

A) Alignment of genomic *Mus musculus* (C57BL6) CD45.1 and CD45.2 gene isoforms. The extracellular domains of CD45.1 and CD45.2 differ by 6 nucleotides (indicated in red) in 3 different regions (designated R1, R2 and R3). CD45.2 region R1 is SEQ ID NO 032, CD45.1 region R1 is SEQ ID NO 033, CD45.2 region R2 is SEQ ID NO 034, CD45.1 region R2 is SEQ ID NO 035, CD45.2 region R3 is SEQ ID NO 036, CD45.1 region R3 is SEQ ID NO 037. sgRNA binding sites (green line), PAM sequence (black line). B) High resolution gene editing-based mapping of the native CD45.1 epitope. Experimental setup as in FIG. 5A. The three candidate regions were cut in primary CD4+ T cells using three different sgRNAs targeting the CD45.2 gene as close as possible to the SNP of interest (sgRNA-CD45.2_R1, sgRNACD45.2_R2 and sgRNACD45.2_R3) and repaired with 3 different 180 bp ssDNA CD45.1 templates (R1, R2, R3). Immediately after purification of GFP+ cells addition of vanillin (NHEJ inhibitor) for 24 h. Nine days later cell harvest and flow cytometry for CD45.2 and CD45.1. The experiment was carried out once with EL-4 cells and once with primary CD4+ T cells. C) Validation of results obtained in B using a longer (1 kb CD45.1 dsDNA) template. The Lys277Glu mutation is necessary and sufficient to switch CD45.2 reactivity to CD45.1 reactivity. Data are displayed as representative flow cytometry plot (left panel) and quantification of multiple experiments (right panel). (Representative data from n=3 experiments; error bars represent SD). D) Enrichment of HDR-edited cells using isoform switching of a surrogate cell surface marker. EL-4 cells electroporated with plasmids encoding 2 sgRNAs (sgRNACD90.2 and sgRNACD45.2_R1) and 2 kb dsDNA templates (CD90.1 and CD45.1) for multiplexed HDR. Cells were cultured for the next 24 h in vitro in order to allow GFP expression. Immediately after purification of GFP+ cells addition of vanillin (NHEJ inhibitor) for 24 h. Cells were expanded nine days in vitro, then harvested and examined by flow cytometry for CD90.2, CD90.1, CD45.2 and CD45.1 expression. Top panel: Pre-gating on CD90.T (green) and CD90.1+(red) i.e. isoform switched cells demonstrates that HDR events at a second locus (Ptprc) are linked within the same cell. CD45 isoform switched cells (lower panels) are more frequent in cells which also switched the CD90 isoform. Representative data from two experiments, once with long templates, once with 180 bp ssDNA templates. E) Selection of zygosity of HDR-edited cells. Experimental data as in d. Top panel: Pre-gating on heterozygous CD90.1+/CD90.2+ cells (solid red line) enriches CD45.1+/CD45.2+ heterozygous cells (left bottom panel). Pre-gating on homozygous CD90.1+/CD90.1+ cells (top panel, dotted red line) enriches homozygous CD45.1+/CD45.1+ cells (bottom panel).

FIG. 4 shows the gene correction of scurfy cells and cells bearing the human Foxp3K276X mutation as well as enrichment of the relative frequency of gene-repaired cells when gating on an isoform-switched surrogate surface marker.

A) Alignment of genomic DNA sequences of wildtype foxp3 (C57BL/6) (SEQ ID NO 038), the Foxp3 locus with a targeted mutation Foxp3K276X (SEQ ID NO 039) which introduces a premature stop codon and the Foxp3 locus of scurfy mice (B6.Cg-Foxp3sf/J) which harbor a spontaneous 2 bp insertion leading to a frame-shift (SEQ ID NO 040). sgRNA binding sites (green line) and PAM sequences (black line). B) Protocol for gene editing of total CD4+ T cells from Foxp3K276X C57BL/6 mice. In vitro activation and electroporation (step 1) with plasmids encoding sgRNA targeting the Foxp3K276X mutation and a circular plasmid containing a 1 kb wildtype (wt) Foxp3 repair template. Successfully transfected cells are isolated based on GFP expression (step 2). Cell expansion in vitro for gene editing in presence of rhIL-2, TGF-p alone or in combination with retinoic acid (RA) and cytokine neutralizing antibodies (anti-IL-4 and anti-IFNy for 7 days (step 3). C) Experimental setup as in B with total CD4+ T cells from control mice (WT) or Foxp3K276X mice. Flow cytometry of CD25 and Foxp3 expression (gated on live CD4+ T cells). Wildtype cells electroporated with empty px458 plasmid differentiate into CD4+ Foxp3+CD25+ T cells (left panel), absence of Foxp3 differentiation in Foxp3K276X cells electroporated with sgRNA Foxp3K276X alone (middle panel) and restoration of Foxp3 protein expression in Foxp3K276X cells electroporated with sgRNA Foxp3K276X and 1 kb Foxp3 dsDNA repair template (right panel). Top row: Foxp3 induction with TGF-p alone, bottom row: Foxp3 induction with TGF-p combined with RA. Compared to TGF-p alone the combination of TGF-p and RA leads to a higher frequency of Foxp3 expressing cells in those cells which have an intact Foxp3 locus (i.e. wildtype and repaired cells). Representative data from 2 experiments with Foxp3K276X cells and one experiment with Foxp$^{sf}$/J cells. D) Enrichment of gene-repaired Foxp3 expressing cells using multiplexed CD45 isoform switching as a surrogate marker. Experimental setup as in b but simultaneous electroporation of plasmids encoding 2 sgRNAs (sgRNA Foxp3K276X and sgRNACD45.2_R1) and two 1 kb dsDNA templates (Foxp3 wildtype and CD45.1). Seven days later flow cytometry of CD45.2, CD45.1, CD25 and Foxp3 (gated on live CD4+ cells). Top panel: Pre-gating on CD45.1-cells (green line) and CD45.1+ cells (red line). Bottom panel: Enrichment of CD25+ Foxp3+ cells in isoform switched CD45.1+ cells. Representative data from 2 experiments with Foxp3K$^{276}$X cells and one experiment with Foxp$^{sf}$/J cells.

FIG. 5 shows supplementary data related to FIG. 2.

A) Protocol for plasmid-based HDR in CD4 T cells. Bead-enriched naive CD4+ T cells are activated in vitro for 24 h and subsequently electroporated with a plasmid encoding a sgRNA targeting the gene X, Cas9 and GFP. In addition, cotransfection of either a ssDNA HDR template or a circular dsDNA plasmid containing a HDR template cloned in pUC57 vector (here shown as template Y) (step 1). After 24 h successfully transfected cells are purified by flow cytometry based on GFP expression (step 2). Immediately after cell sorting 24 h incubation with NHEJ inhibitor. Subsequent in vitro cell expansion for gene editing for 6-9 days with reactivation 4 days post sorting (step 3). EL-4 cells are transfected the same way, except they do not require TOR activation prior to the electroporation or on day 4 post sorting and electroporation parameters are different (see Materials & Methods). B) Genomic CD90.1 and CD90.2 nt and aa sequences. CD90.1 nt: SEQ ID NO 041, CD90.2 nt: SEQ ID NO 042. The CGA (CD90.1) CAA (CD90.2) SNP leading to R108Q is highlighted in red. C) Graphic representation of the experimental readout: Q1: unedited cells or cells with mutations which do not abolish protein expression, e.g. in-frame mutations Q2: cells after NHEJ Q3: edited CD90.2/CD90.1 heterozygous cells Q4: edited homozygous CD90.1 cells or cells with one KO allele and one HDR edited allele. D) Schematic illustration of 3 different sized ssDNA CD90.2 templates (90 bp: SEQ ID NO 016, 120 bp: SEQ ID NO 017 and 180 bp: SEQ ID NO 018) centered on the sgRNA90.1 cut site. E) Effect of different mutations in the template for isoform switching. 180 bp ssDNA CD90.1 templates with no mutations (no mt, SEQ ID NO 013), mutated PAM (mt PAM (1 nt), SEQ ID NO 014) or mutated PAM (2 nt) plus 3 additional mutations (mt PAM (2nt)+3 other nt, SEQ ID NO 014). EL-4 cells were transfected as in a, with a plasmid encoding a sgRNA targeting CD90.2 (sgRNA CD90.2, SEQ ID NO 001) and different 180 bp ssDNA CD90.1 templates. Flow cytometry nine days later. F) The same experiment as in FIG. 2D but data analyzed with a different gating strategy. Representative flow cytometry plots gated on blasting cells and quantification of HDR efficiency across multiple experiments (n=3; error bars represent SD). The frequency of heterozygous (het) and homozygous (homo) cells is higher in blasting cells compared to gating on all lymphocytes. G) Experimental design to determine the effect of the cut-to-mutation distance on HDR efficiency. Binding sites for 2 different sgRNAs targeting CD90.2 relative to the mutation of interest: sgRNACD90.2 (SEQ ID NO 001) binds on the mutation site while sgRNACD90.2-A (SEQ ID NO 002) binds 50 nt away relative to the mutations site. The top bar represents repair templates of different length.

FIG. 6 shows supplementary data related to FIG. 3: Validation of correct CD45.2 to CD45.1 isoform switching by Sanger sequencing. EL-4 cells were electroporated with a plasmid encoding a CD45.2 targeting sgRNA (sgRNACD45.2) and a circular dsDNA 2 kb plasmid template of CD45.1 as described in FIG. 5A. Cells were cultured for nine days in vitro, then harvested and sorted by flow cytometry based on CD45.2 and CD45.1 expression in order to isolate four defined populations: CD45.2+/CD45.T (Q1), CD45.27CD45.T (Q2), CD45.2+/CD45.1+ (Q3) and CD45.27CD45.1+ (Q4). DNA was extracted and PCR amplicons cloned for Sanger sequencing. In each quadrant sequencing results are shown with a description of the mutations to the right of the genomic sequence. Numbers in the bottom right of each quadrant describe the frequencies of wt sequences or NHEJ vs HDR repair. The circled number 1 above the arrow represents the PAM mutation 930G to A which was introduced in the CD45.1 template. The circled number 2 above the arrow represents the mutation of interest (Lys277Glu). No indels were found at both ends of the templates for populations Q3 and Q4 (data not shown). Post sort purity data is shown in FIG. 6B. Left panel: cartoon of the labelling of the 4 quadrants defining the 4 distinct cell populations. Right panel: Shown is an electronic overlay of the four purified populations. The following four defined populations were purified: CD45.2+/CD45.1− (Q1; red), CD45.2−/CD45.1− (Q2; green), CD45.2+/CD45.1+ (Q3; blue) and CD45.2−/CD45.1− (Q4; orange). This demonstrates that isoform/allele switching allows to isolate highly pure distinct populations of cells from a mixed population of genotypes/phenotypes based on the expression of the original and edited alleles.

FIG. 7 shows that two monoclonal antibodies can discriminate isoform Thy1.1 (clone OX-7) from isoform Thy1.2 (clone 53.2-1) in inbred congenic mice which are homozygous for Thy1.2 (A), heterozygous for Thy1.2 and Thy1.1 (B) or homozygous for Thy1.1 (C). The figure also shows that the zygosity of the two isoforms can be determined on a single cell level. The genomic difference between isoform Thy1.1 and isoform Thy1.2 is a single nucleotide difference (nucleotide 14 in SEQ ID NO 041 and SEQ ID NO 042).

FIG. 8 shows the generation of a stable Cas9 expressing murine cell line. A) The presence of genomic Cas9 DNA in these cells was validated by PCR, amplifying Cas9 locus (forward primer: AACAGCCGCGAGAGAATGAA, SEQ ID NO 030 and reverse primer TCGGCCTTGGTCAGAT-TGTC, SEQ ID NO 031) and compared to the Cas9 sequence in Cas9 transgenic (Cas9 Tg mice) or wildtype mice (WT mice). B) sgRNAs for Thy1.2 and CD45.2 were generated by in vitro transcription from a dsDNA template coding for a T7 promoter followed by the sgRNAs and transfected in Cas9 expressing cells lines. In all tested cell lines electroporating in vitro transcribed sgRNAs is sufficient to lead to high homozygous multiplexed gene deletion of Thy1 and CD45 (Q2). Shown are FACS plots for 6 different Cas9 expressing EL-4 cell lines.

FIG. 9 shows the transfection of primary human T cells from peripheral blood or from human cord blood. The experimental conditions correspond to the ones used for mouse cells. For a detailed protocol, see methods section. Briefly, PBMC or naive T cells are isolated from human blood, activated in vitro using anti-CD3 and anti-CD28 antibodies, then electroporated with a plasmid expressing guide RNA, Cas9 (or other) nucleases and a selection marker such as GFP (used as marker for successful electroporation). GFP can be replaced by alternative markers, e.g. tNGFR (truncated nerve growth factor receptor) approved for GMP production. Specific conditions are described in the materials and methods section.

Figure 10:
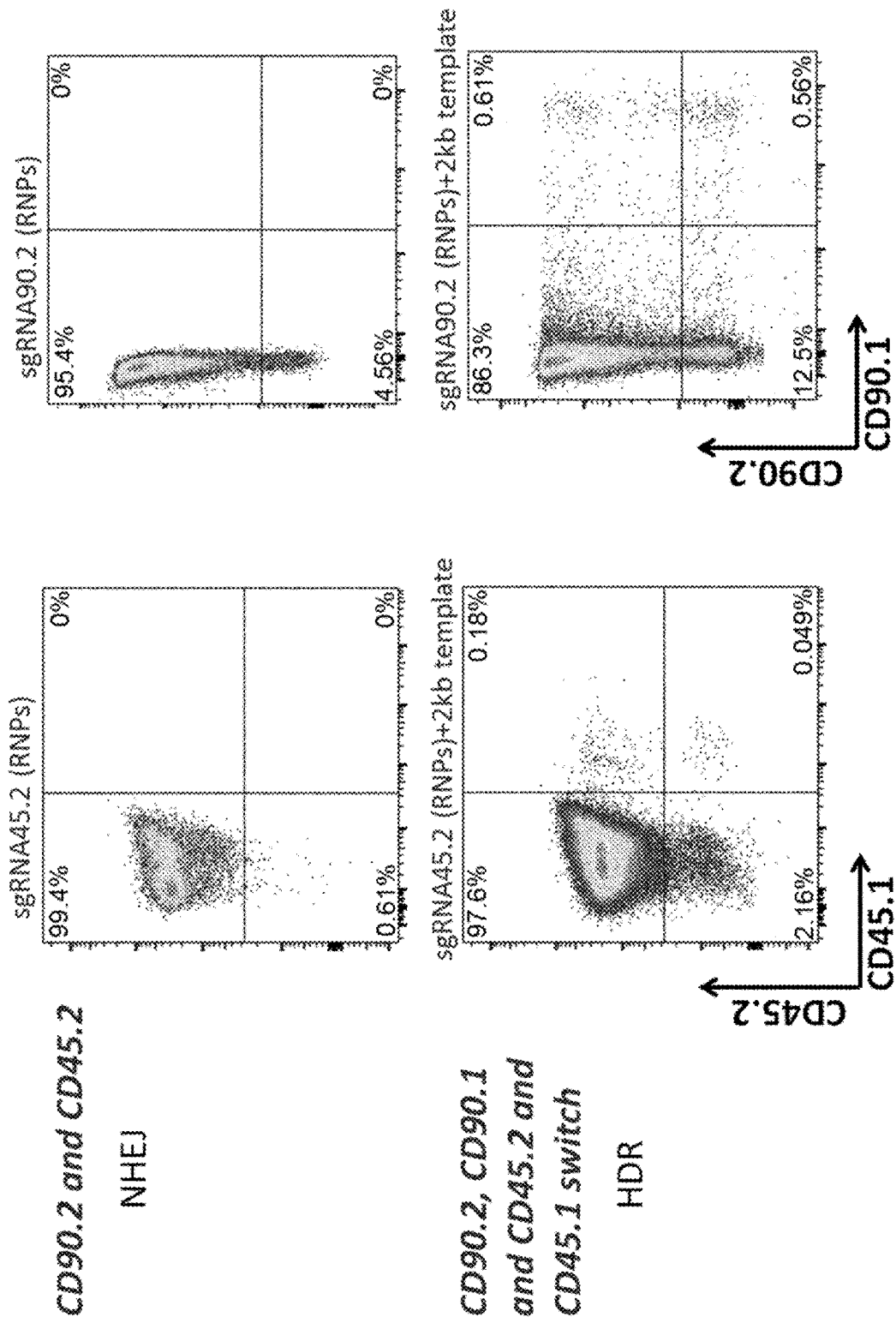

FIG. 10 shows gene editing in EL4 cells using Cas9 ribonucleoprotein particles (RNPs). EL4 cells were transfected with crRNA:tracrRNA/Cas9 complex and +/− HDR 2 kb template in the same way as for the plasmid based approach, except for electroporation conditions (described in methods section).

Figure 11:
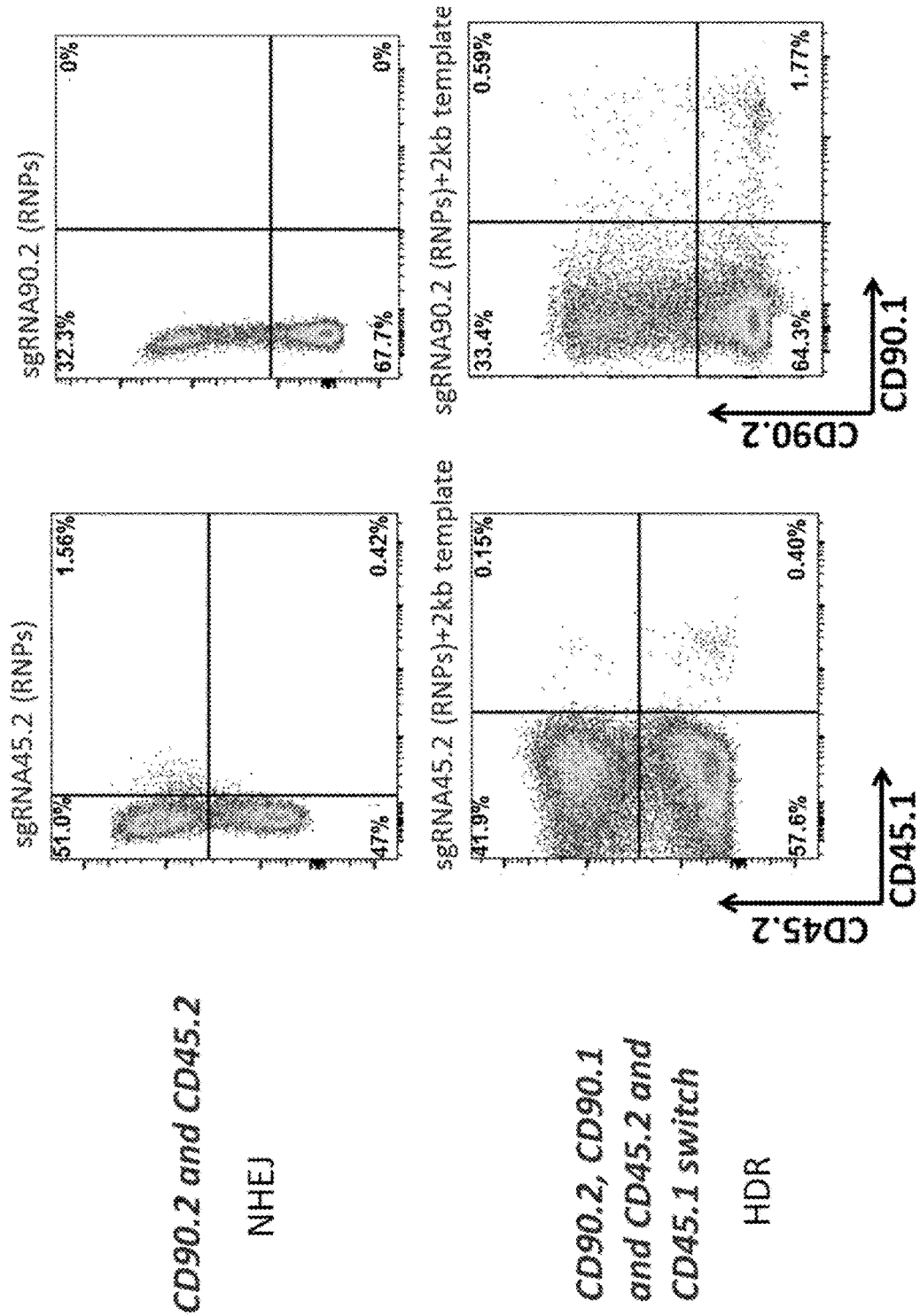

FIG. 11 shows gene editing in primary mouse T cells using Cas9 ribonucleoprotein particles (RNPs). Primary mouse T cells were transfected with crRNA:tracrRNA/Cas9 complex and +/− HDR 2 kb template in the same way as for the plasmid based approach.

Figures 12A, 12B:
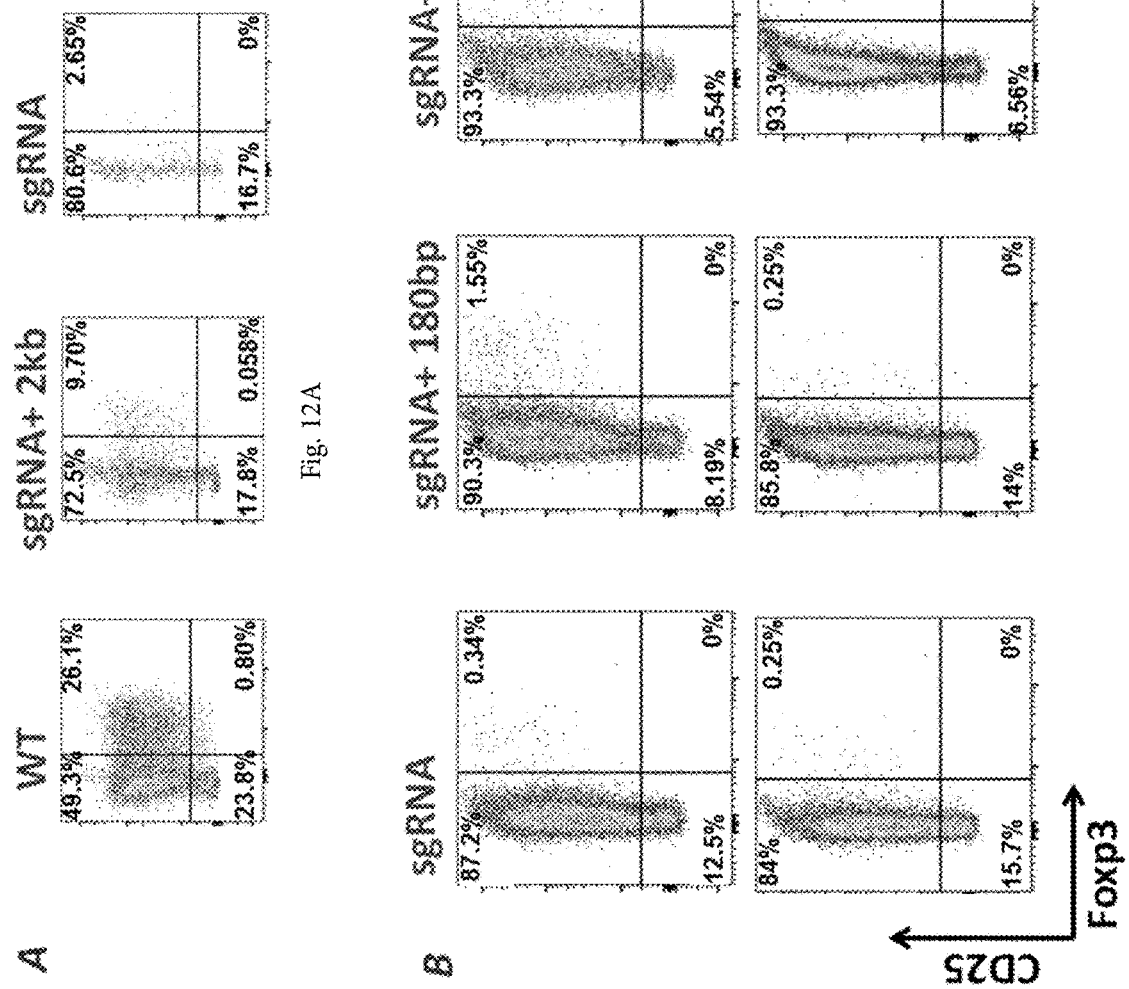

FIG. 12 shows repair of the Foxp3 gene using the plasmid based approach and the RNP based approach. A: CD4 T cells from Foxp3 KO mice were transfected with sgRNA plasmid alone or together with a Foxp3 wildtype HDR template. GFP+ and GFP− cells were sorted 24 h post transfection (plasmid transfection) and immediately after cell sorting expanded until the end of the experiment in the presence of Foxp3 differentiation cocktail. B: CD4 T cells from Foxp3 KO mice were transfected with crRNA:tracrRNA/Cas9 RNP complex alone or +/− HDR templates (180 bp ssDNA or 2 kb plasmid). Total pool of RNPs transfected cells were expanded until the end of the experiment in the presence of Foxp3 differentiation cocktail.

Figure 13A:
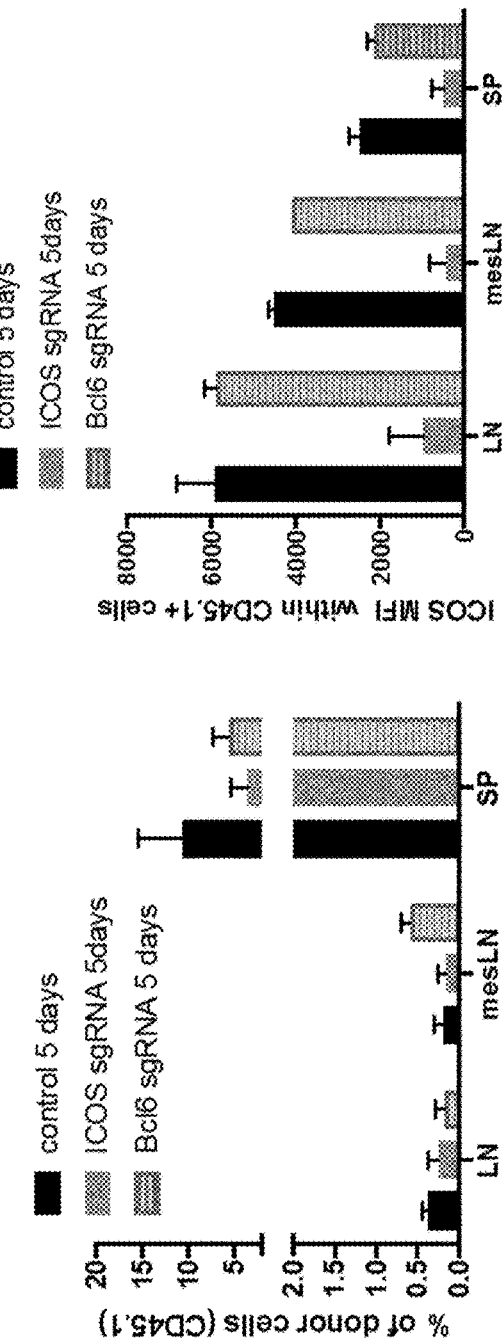
Figure 13B:
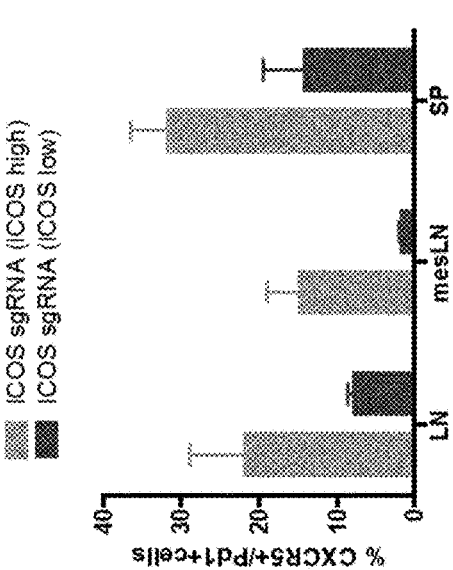
Figure 13C:
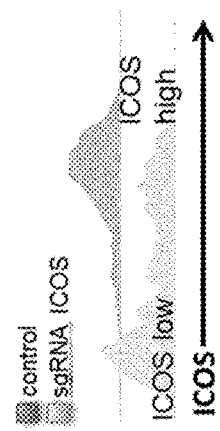

FIG. 13 shows edited cells during lymphocytic choriomeningitis virus (LCMV) transfection. A: Demonstrates that edited/CD45.1+ cells (sgRNA ICOS, sgRNA Bcl6 or control (empty plasmid)) can be recovered in the peripheral lymph nodes (LN), mesenteric LN (mesLN) and spleen (SP) post adoptive T cells transfer and LCMV infection. B: Demonstrates ICOS targeting (decreases in ICOS MFI in different organs relative to the control and sgRNA for Bcl6, another TFH marker). C: Demonstrates impaired T follicular helper cells differentiation (defined by CXCR5 and PD1) in ICOS low (deleted) vs. ICOS (high) population.

Figure 14:
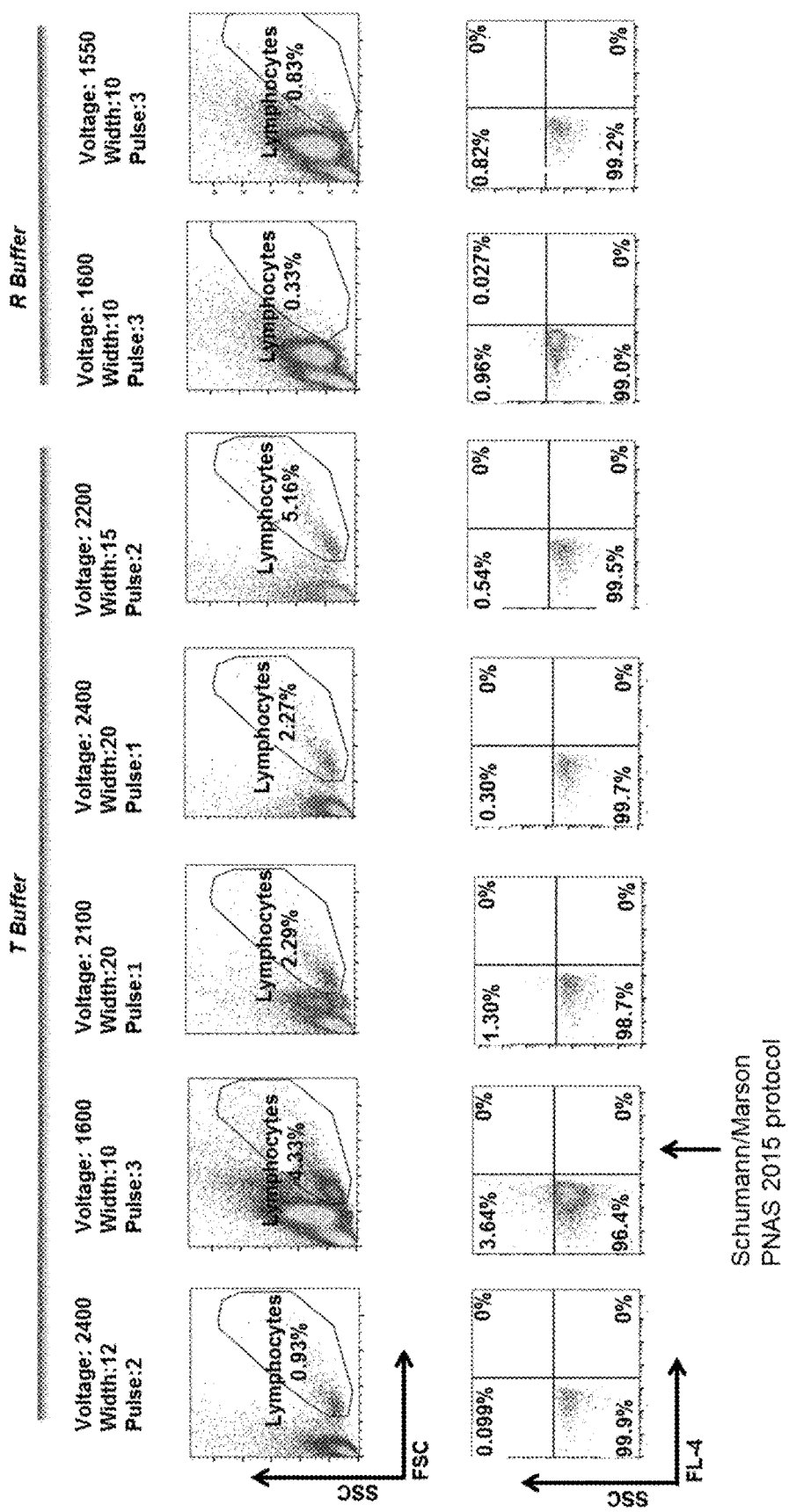

FIG. 14 shows optimization of electroporation conditions for a human CD4+ T cell clone. A human antigen-specific CD4+ T cell clone was activated with cognate peptide and then electroporated with a Neon electroporator to compare different buffers (buffer T, buffer R, both from Thermo Fisher/Invitrogen provided by the Neon kit) and different electroporation conditions (voltage, width, pulse) as indicated. The plasmid used to transfect was p-EGFP-N1 (designated "small (GFP) plasmid"). The 4.7 kb plasmid pEGFP-N1 is from Takara/Clontech. Analysis of live lymphocytes based on FSC/SSC and GFP expression gated on live lymphocytes. Indicated as a reference is the protocol published by Schuman et al., PNAS 2015, doi: 10.1073/pnas. Most conditions killed the majority of cells. Transfection efficiency (read out by GFP expression) among live cells was low with all conditions. Choice of this plasmid: we used this plasmid successfully to optimize electroporation conditions for mouse T cells.

Figure 15:
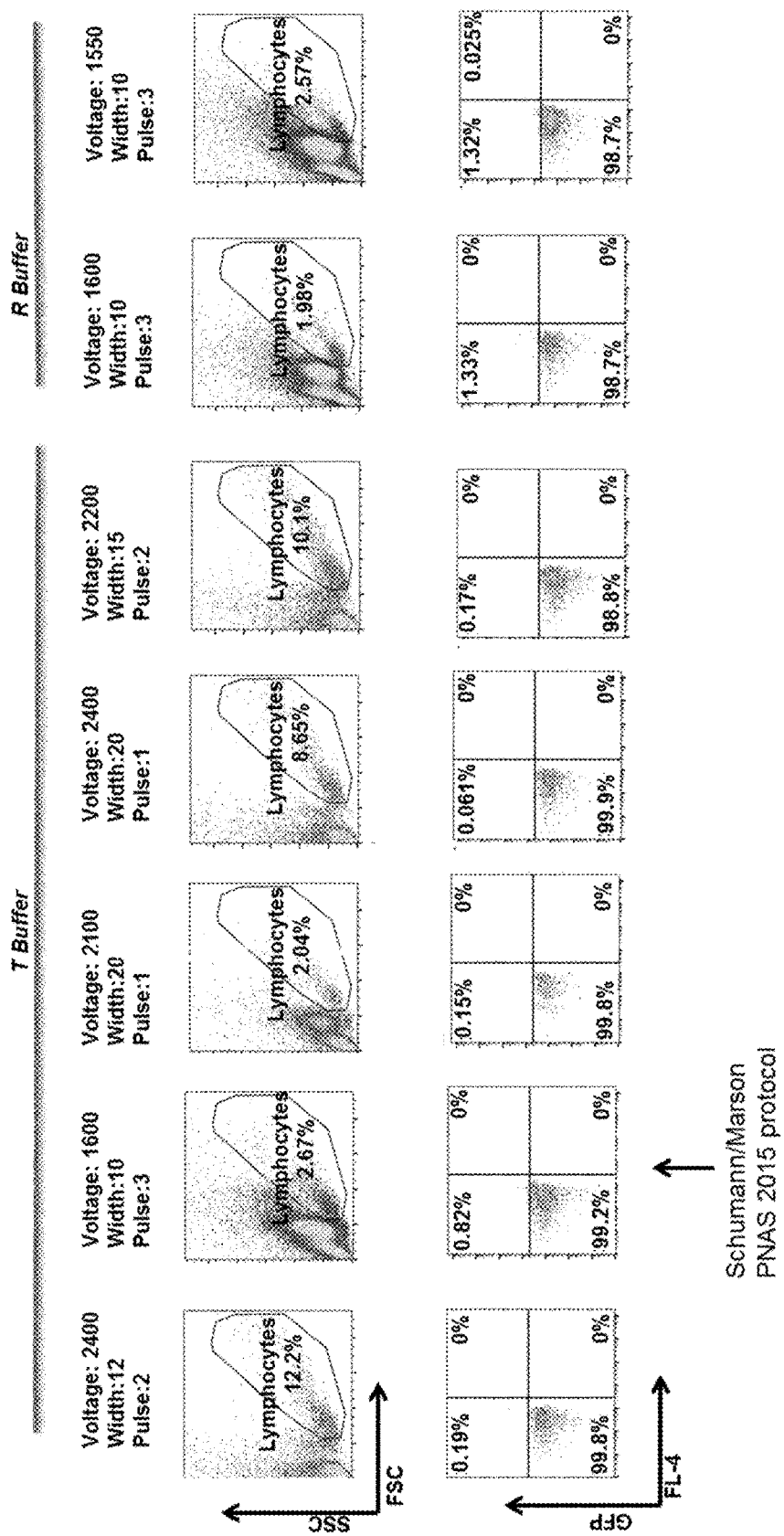

FIG. 15 shows the optimization of electroporation conditions for a human CD4+ T cell clone. Same conditions as in FIG. 14, except that the large Cas9-GFP expression plasmid px458 was used (Addgene pSpCas9(BB)-2A-GFP (PX458) No 48138). Similar to the smaller plasmid most electroporation conditions killed the majority of cells. With the larger plasmid even the best condition (Schumann et al.) did not result in GFP expression.

Figure 16:
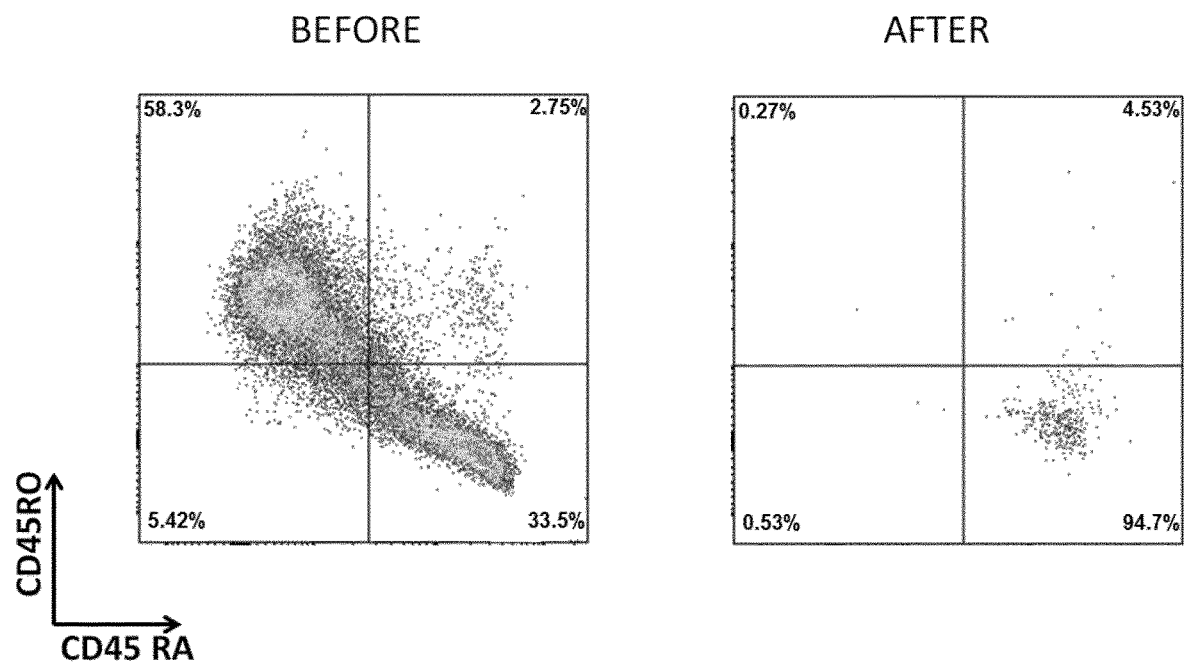

FIG. 16 shows a quality control (purity check) of purification of human naive CD4+ T cells from peripheral blood from adult healthy donors. Isolation of cells as described in Materials & Methods. Purity check before and after enrichment of naive T cells. Before enrichment 33.5% of cells were CD45RO−CD45RA+ naive T cells, after enrichment 94.7% were CD45RA+CD45RO− naive T cells.

Figure 17:
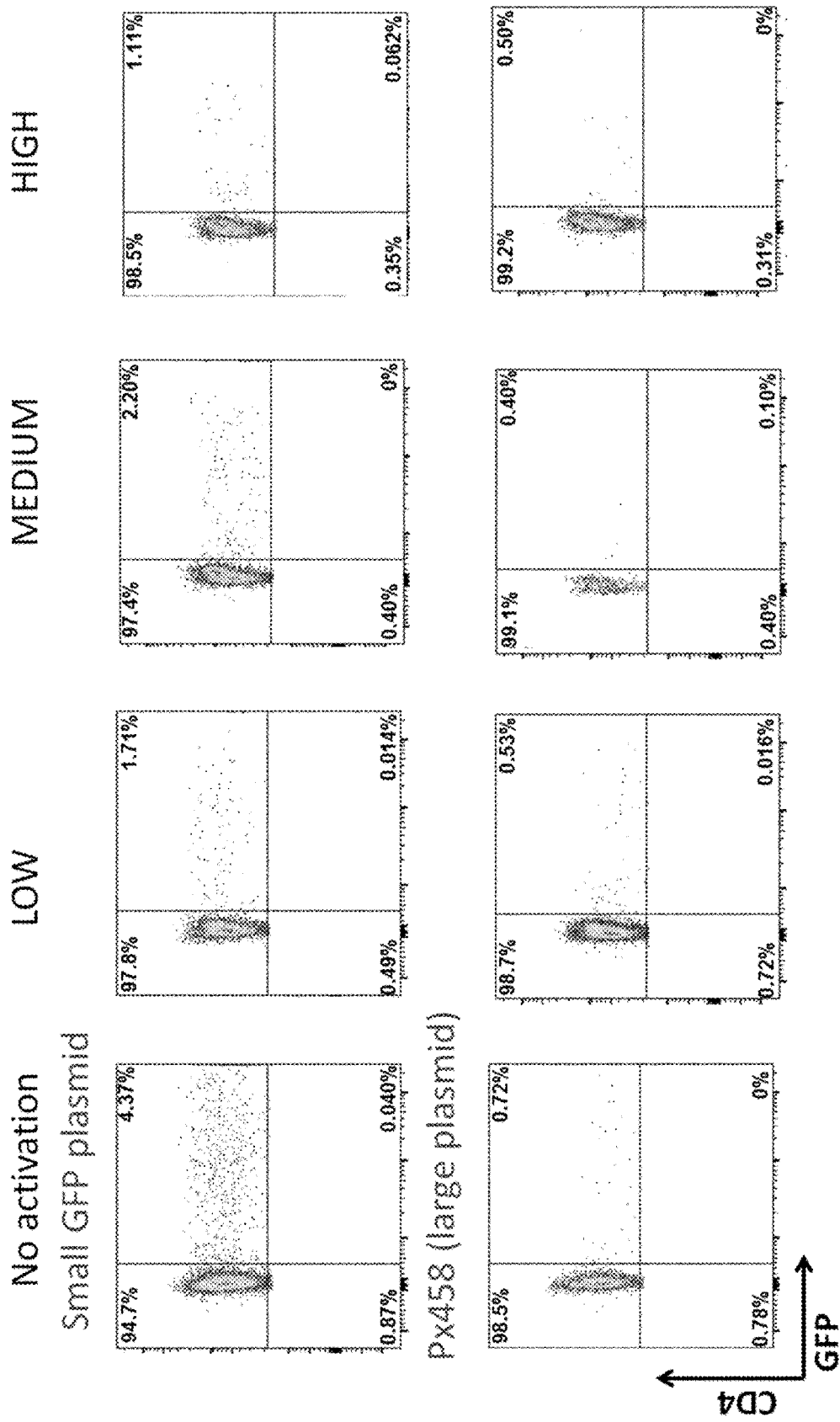

FIG. 17 shows optimization of electroporation conditions for primary human CD4+ T cells. Isolation and activation of primary human CD4+ T cells as described in Materials & Methods. Comparison of transfection efficiency (% GFP+) without T cell activation or with low, medium or high stimulation. Activation conditions as described in Materials & Methods. Comparison of the small plasmid p-EGFP-N1 (top panels) to the large plasmid px458 (bottom panels). Eletroporation settings as described by Schuman et al., PNAS 2015, doi: 10.1073/pnas.

Figure 18:
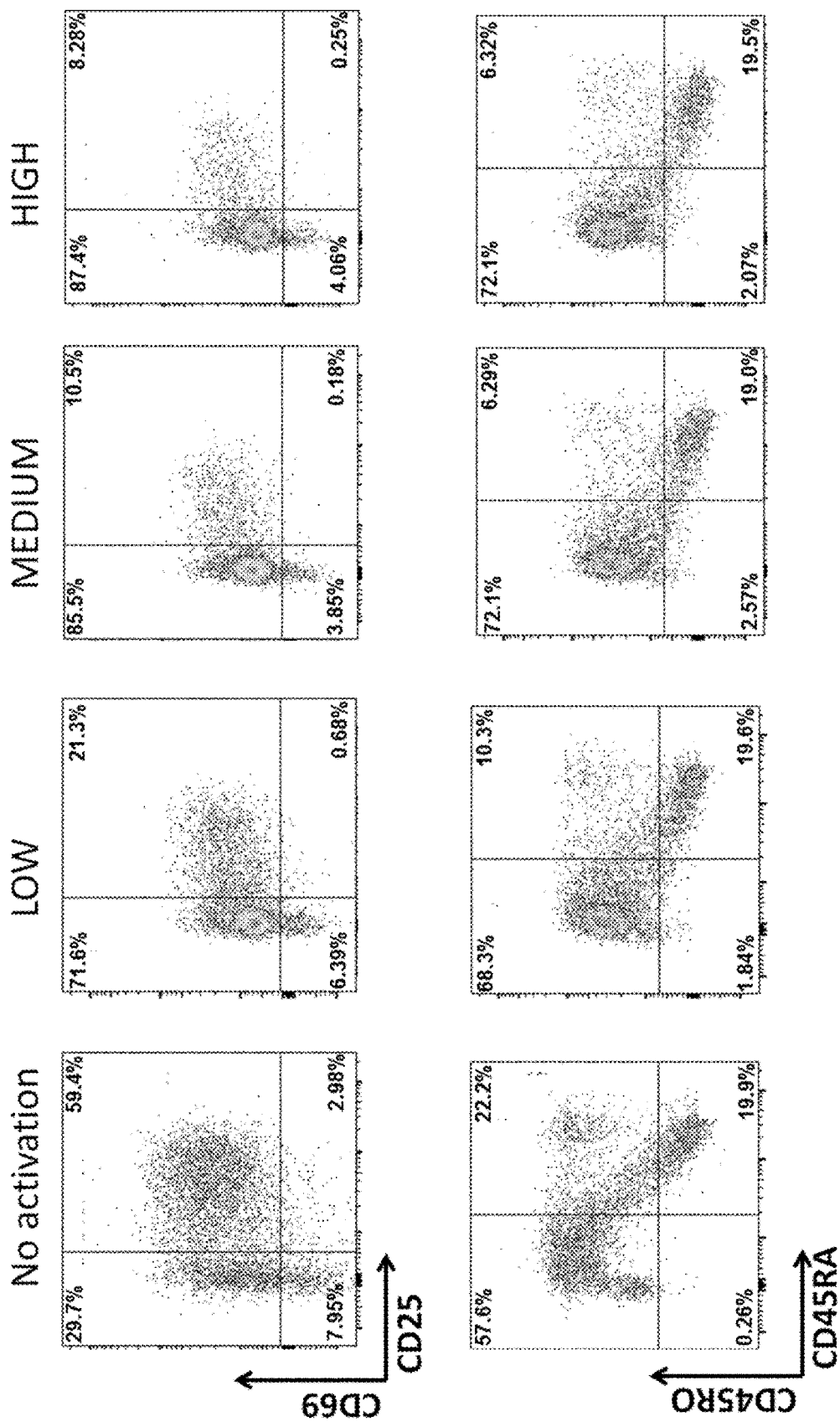

FIG. 18 shows optimization of electroporation conditions for primary human CD4+ T cells. Quality control. Monitoring activation status and comparing the relative distribution of memory (CD45RO+) versus naive (CD45RA+) T cells. Activation conditions as described in Materials & Methods.

Figure 19:
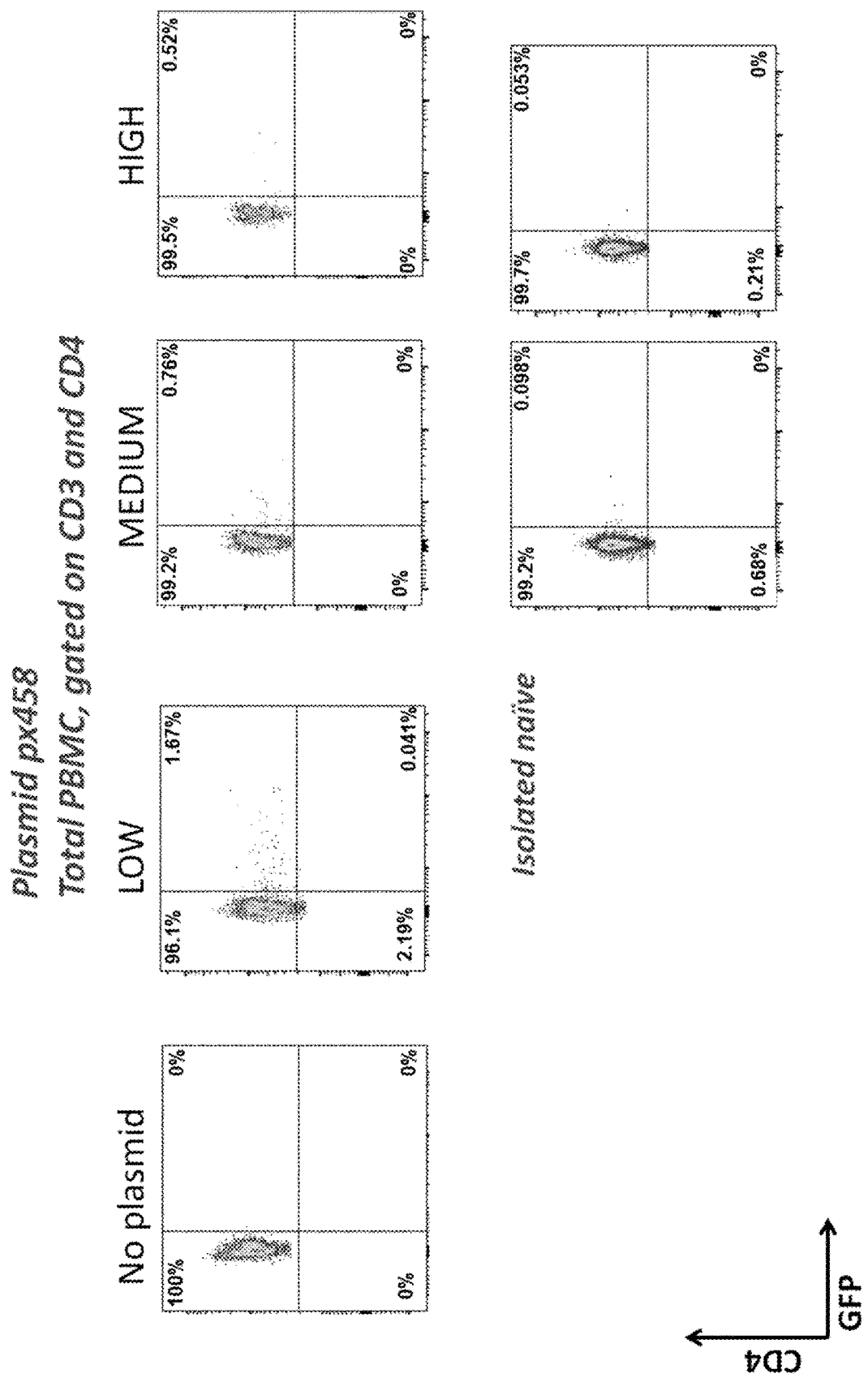

FIG. 19 shows optimization of electroporation conditions for primary human CD4+ T cells. Isolation and activation of primary human CD4+ T cells as described in Materials & Methods. The large px458 plasmid was used. Comparison of transfection efficiency (% GFP+) without T cell activation or with low, medium or high stimulation (total PBMCs, top panels). Comparison to enrichment of naive T cells followed by medium or high activation (bottom panels). Electroporation using the Amaxa Transfection System (Lonza) using program X-001. These conditions yield low or no transfection efficiency.

Figure 20:
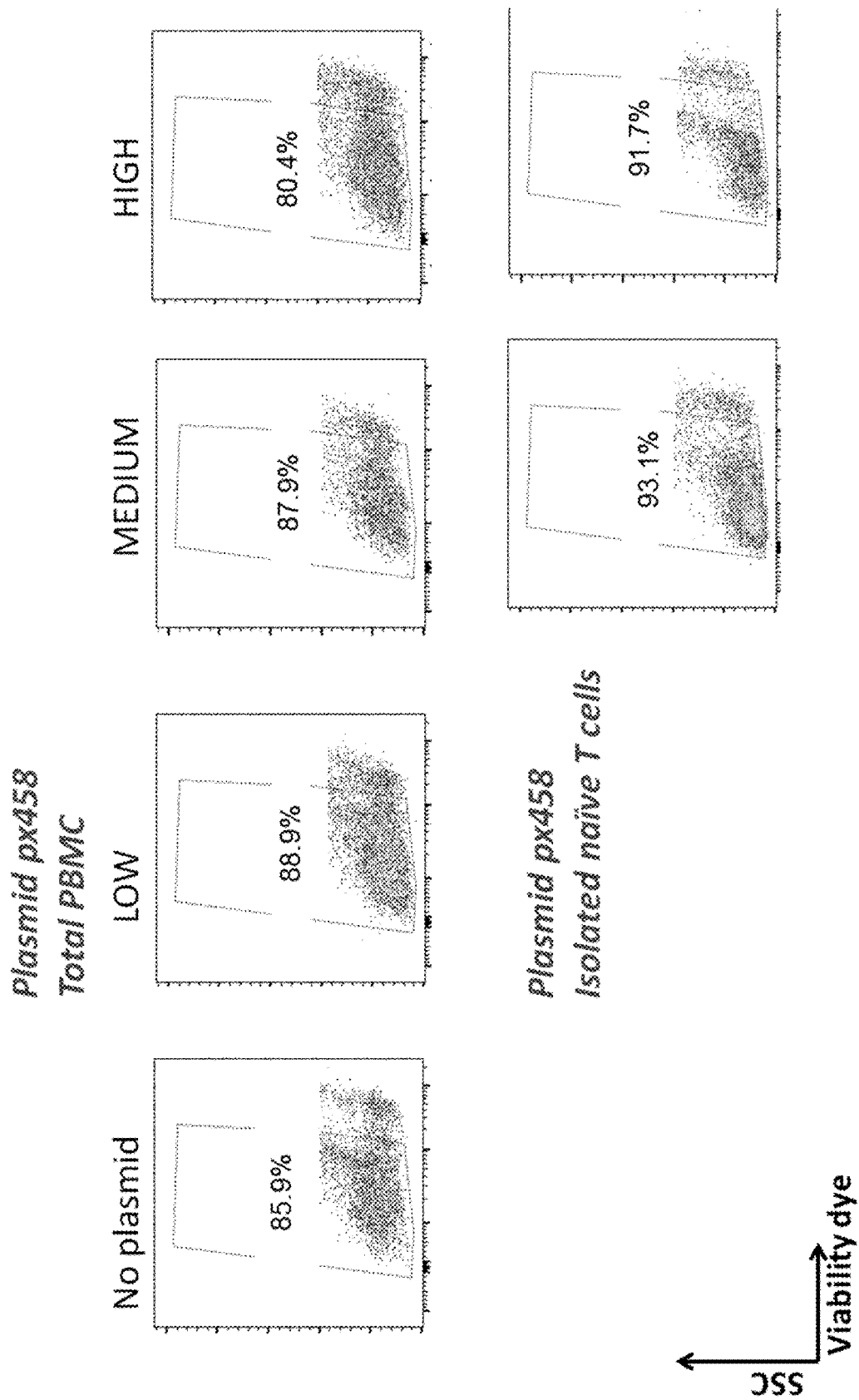

FIG. 20 shows optimization of electroporation conditions for primary human CD4+ T cells. Isolation and activation of primary human CD4+ T cells as described in Materials & Methods. The large px458 plasmid was used. Comparison of viability (gated cells are live) without T cell activation or with low, medium or high stimulation (total PBMCs, top panels) after transfection of plasmid. Comparison to enrichment of naive T cells followed by medium or high activation (bottom panels). Electroporation using the Amaxa Transfection System (Lonza) using program T-020. High viability using these conditions.

Figure 21:
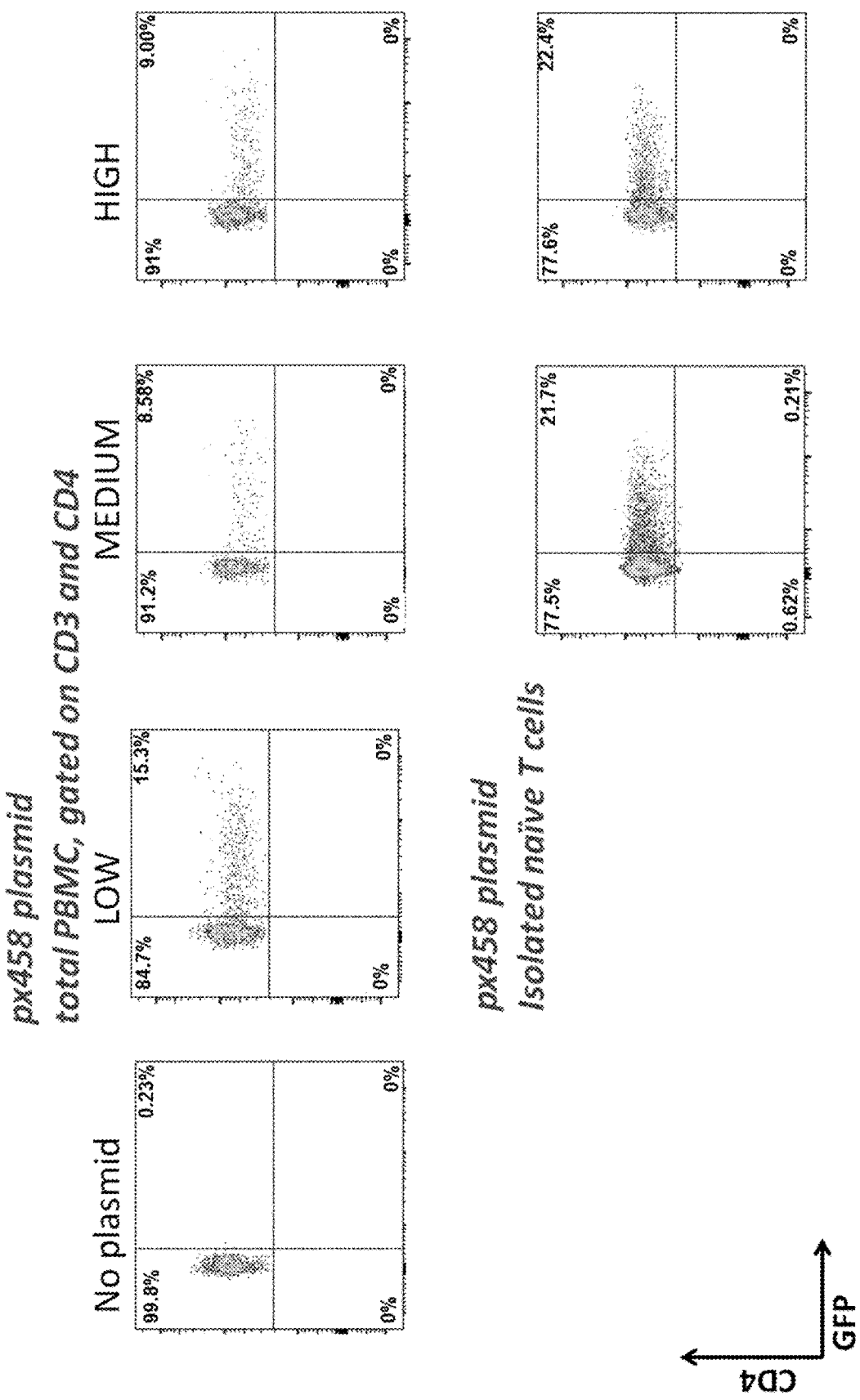
Figure 22:
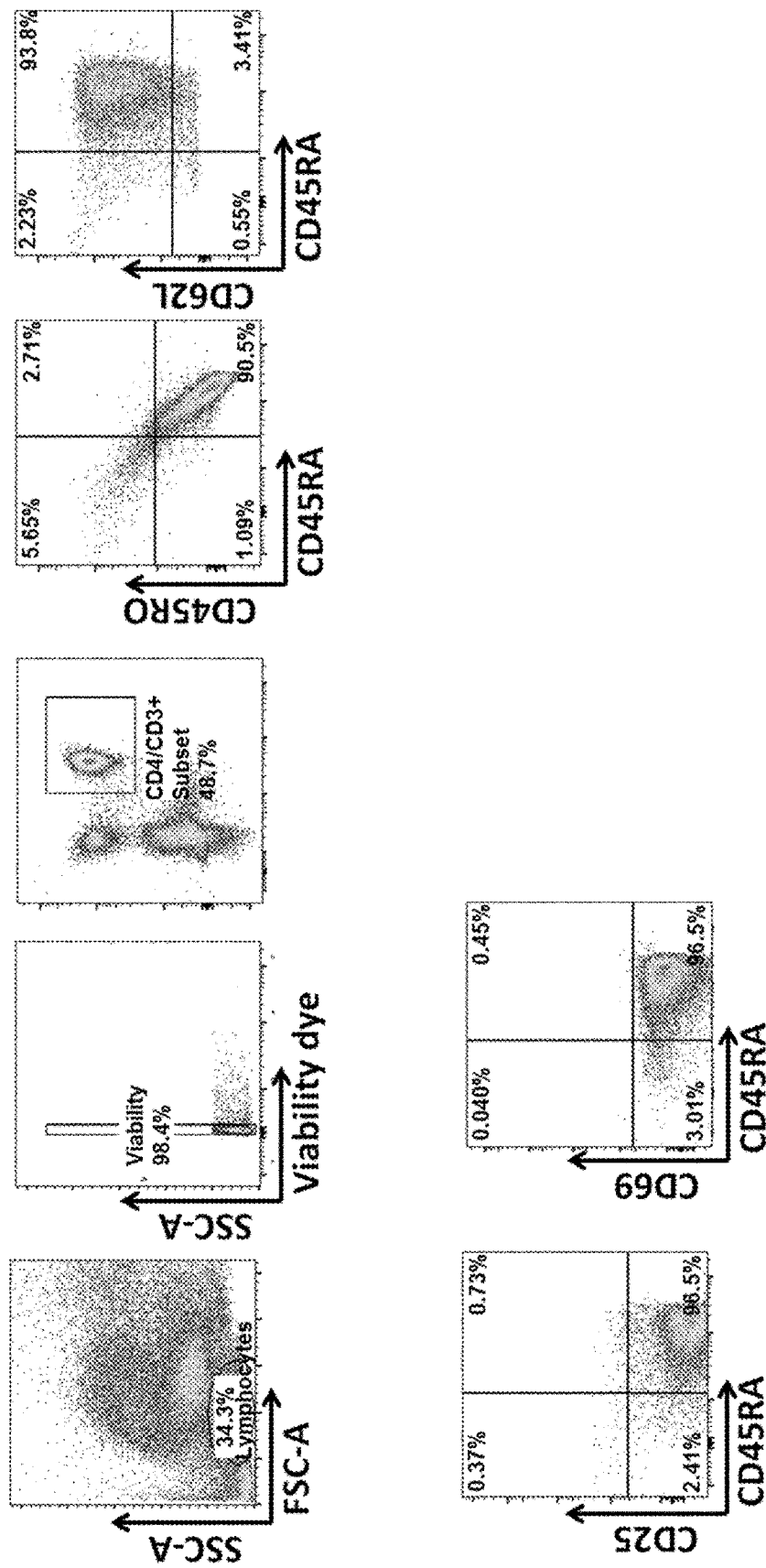

FIG. 21 shows optimization of electroporation conditions for primary human CD4+ T cells. Isolation and activation of primary human CD4+ T cells as described in Materials & Methods. The large px458 plasmid was used. Comparison of transfection efficiency (% GFP+) without T cell activation or with low, medium or high stimulation (total PBMCs, top panels) after transfection of plasmid. Comparison to enrichment of naive T cells followed by medium or high activation (bottom panels). Electroporation using the Amaxa Transfection System (Lonza) using program T-020. High transfection efficiencies using these conditions (8-20%). Enriching naive T cells before activation increases the % GFP+ cells compared to total PBMCs FIG. 22 shows flow cytometric characterization of human cord blood lymphocytes and particularly T cells. The vast majority are naive T cells (CD45RA+CD45RO-).

Figure 23:
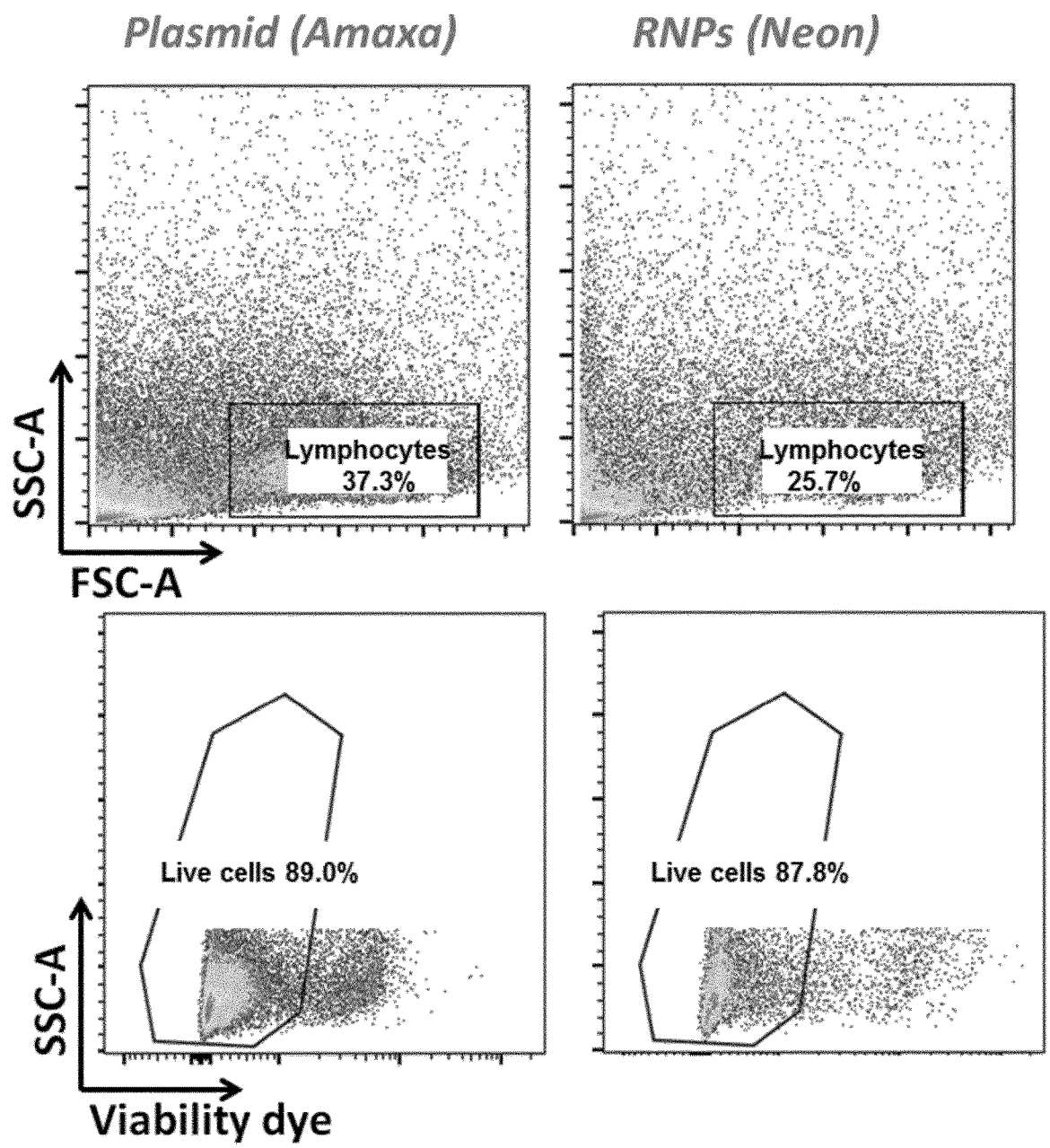

FIG. 23 shows a comparison of cell viability after plasmid transfection versus Cas9 RNP transfection. Starting material: human cord blood without preenrichment of naive CD4+ T cells. Cells were activated using medium activation strength as described in Materials & Methods. Comparison of viability after electroporation with plasmid px458 and Amaxa program T-020 (left panels) to Cas9 RNP electroporation with the Neon electroporator as described in Materials & Methods and Schuman et al., PNAS 2015, doi: 10.1073/pnas (right panels). These electroporation conditions yield comparable viability.

Figure 24:
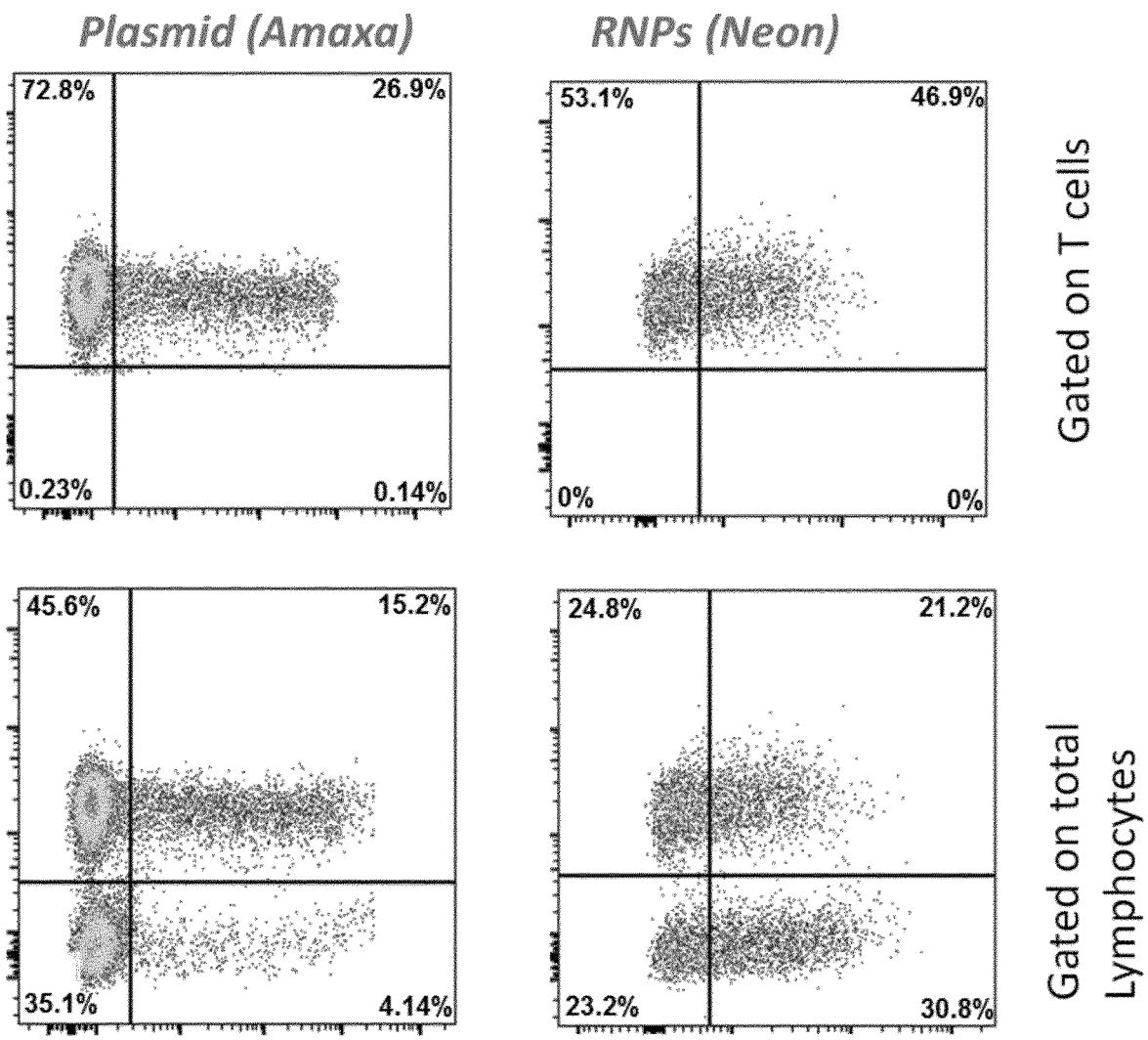

FIG. 24 shows a comparison of transfection efficiencies using plasmid transfection versus Cas9 RNP transfection. Starting material: human cord blood without preenrichment of naive CD4+ T cells. Cells were activated using medium activation strength as described in Materials & Methods. Comparison of transfection efficiency after electroporation with plasmid px458 and Amaxa program T-020 (left panels) to labelled crRNA:tracrRNA-Atto 550/Cas9 RNP electroporation with the Neon electroporator as described in Materials & Methods and Schuman et al., PNAS 2015, doi: 10.1073/pnas (right panels).

Figure 25:
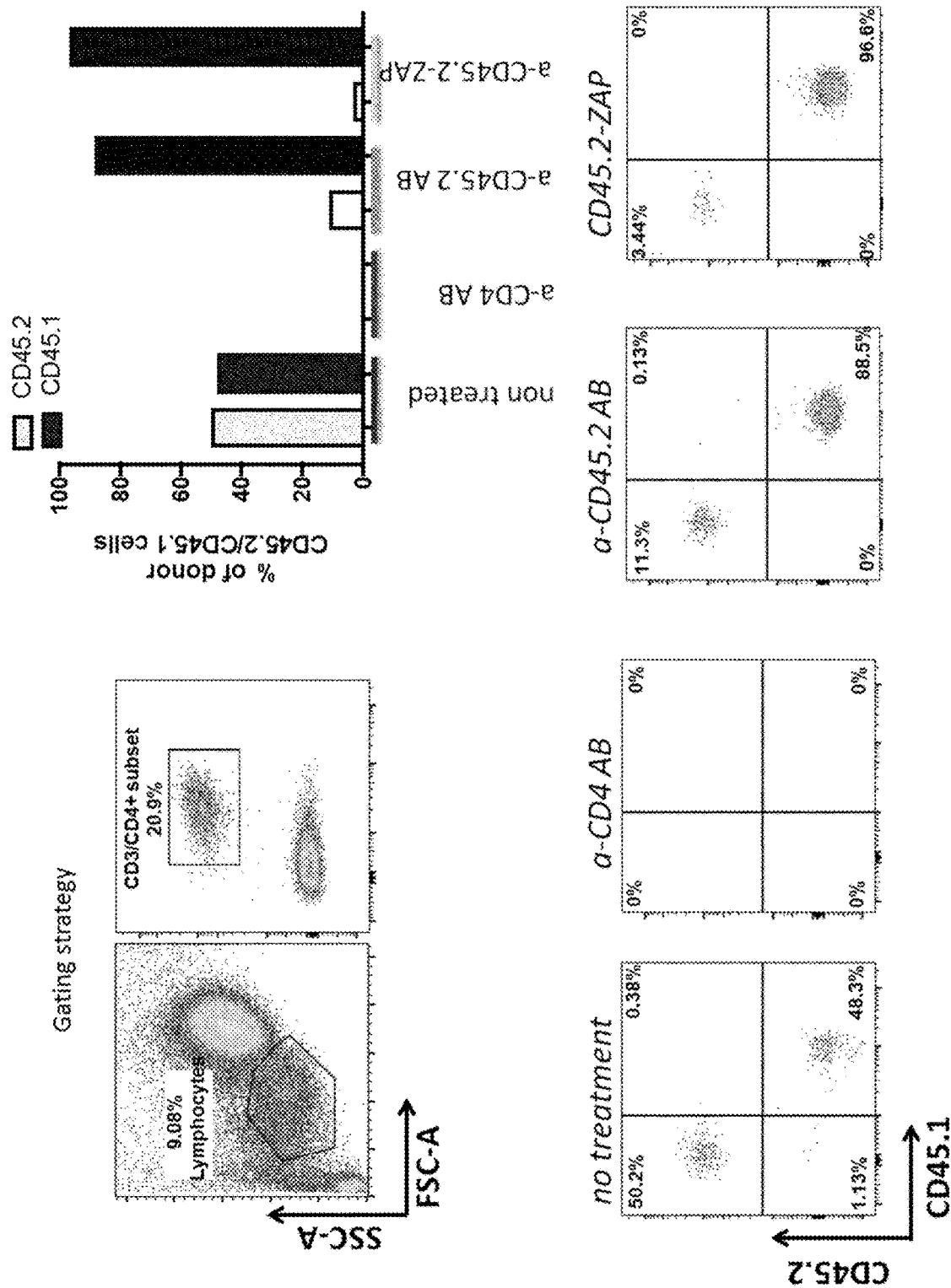

FIG. 25 shows selective depletion of CD45.2+ cells in vivo: peripheral blood. Lymphodeplete RAG KO mice were reconstituted with T cells from homozygous CD45.1+/CD45.1+ and homozygous CD45.2+/CD45.2+ congenic mouse strains mixed at a 1:1 ratio as described in Materials & Methods. Comparison of cell depletion in untreated hosts ("no treatment"), hosts injected with CD4 depleting mAb (clone GK1.5) ("a-CD4 AB") or anti-CD45.2 mAb (clone 104). Anti-CD45.2 mAb was biotinylated but not coupled to toxin (designated "a-CD45.2 AB") or biotinylated and coupled to streptavidin-SAP toxin conjugate (designated "a-CD45.2-ZAP") as described in Materials & Methods. Analysis of peripheral blood one week after depletion. Top panels: Left: Gating strategy: lymphocytes/CD4+CD3+ T cells. Bar graphs (top right panel): quantification of the ratio of CD45.2+/CD45.1+ cells. Bottom panels: representative FACS plots. No treatment: 1:1 ratio of CD45.2+ and CD45.1+ cells remained. Non-selective depletion with anti-CD4 mAb: CD45.1 and CD45.2 cells are both eliminated without discrimination. Depletion with anti-CD45.2 mAb: Selective depletion of CD45.2+ cells leading to a relative increase of CD45.1+ cells. Coupling a toxin to anti-CD45.2 mAb is more efficient but also the uncoupled mAb depletes CD45.2+ cells. This demonstrates that selective depletion of cells with very closely related alleles is possible in vivo.

Figure 26:
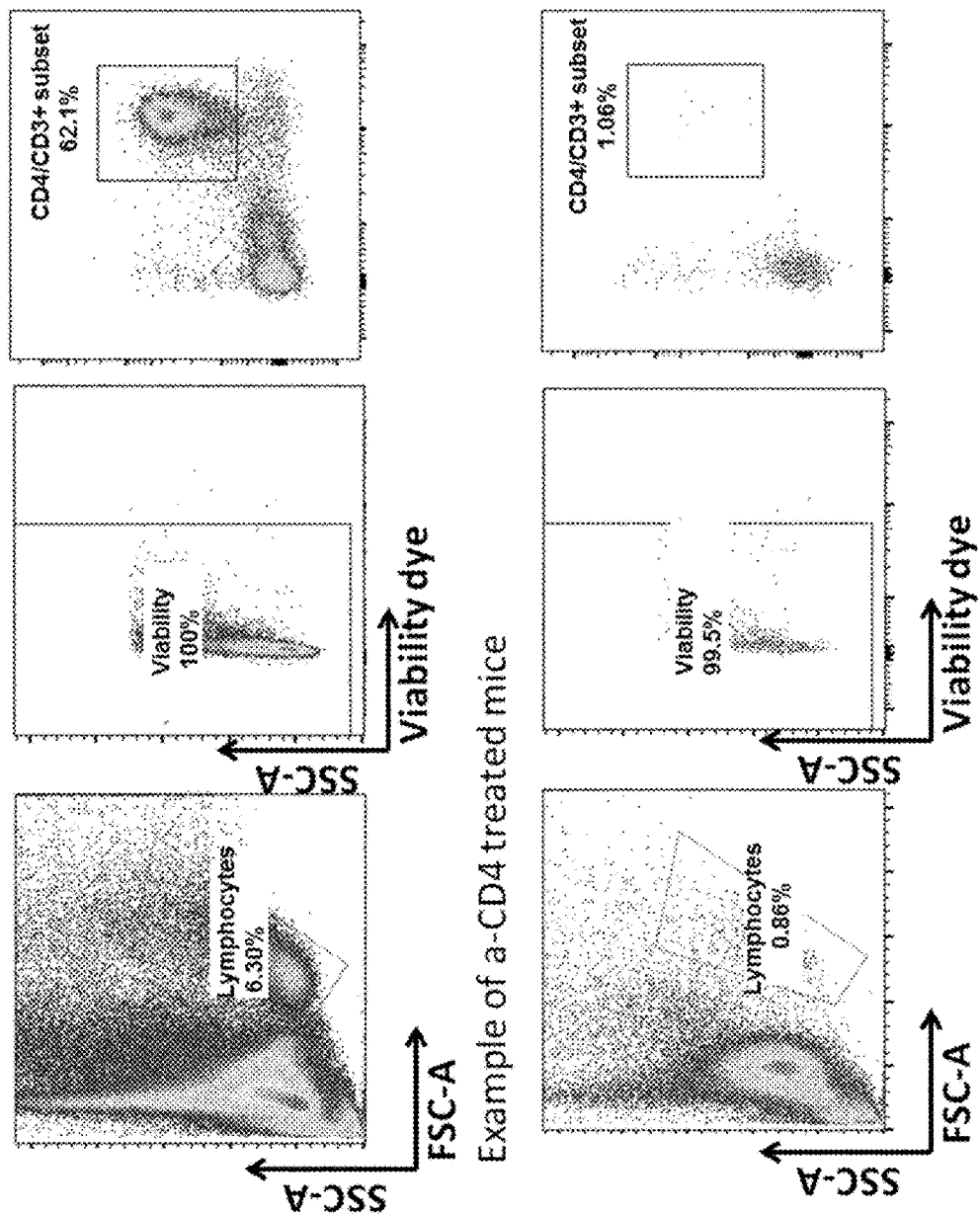

FIG. 26 shows selective depletion of CD45.2+ cells in vivo: lymphoid organs. Same setup as in FIG. 25 but analysis of lymph nodes and spleen. Gating strategy for the analysis of cell depletion. Lymphocyte gate, viability dye, CD3+CD4+ T cells. Host mice treated with depleting anti-CD4 mAb show a strong reduction in lymphocytes visible in the lymphocyte gate but also with CD3 CD4 staining.

Figure 27:
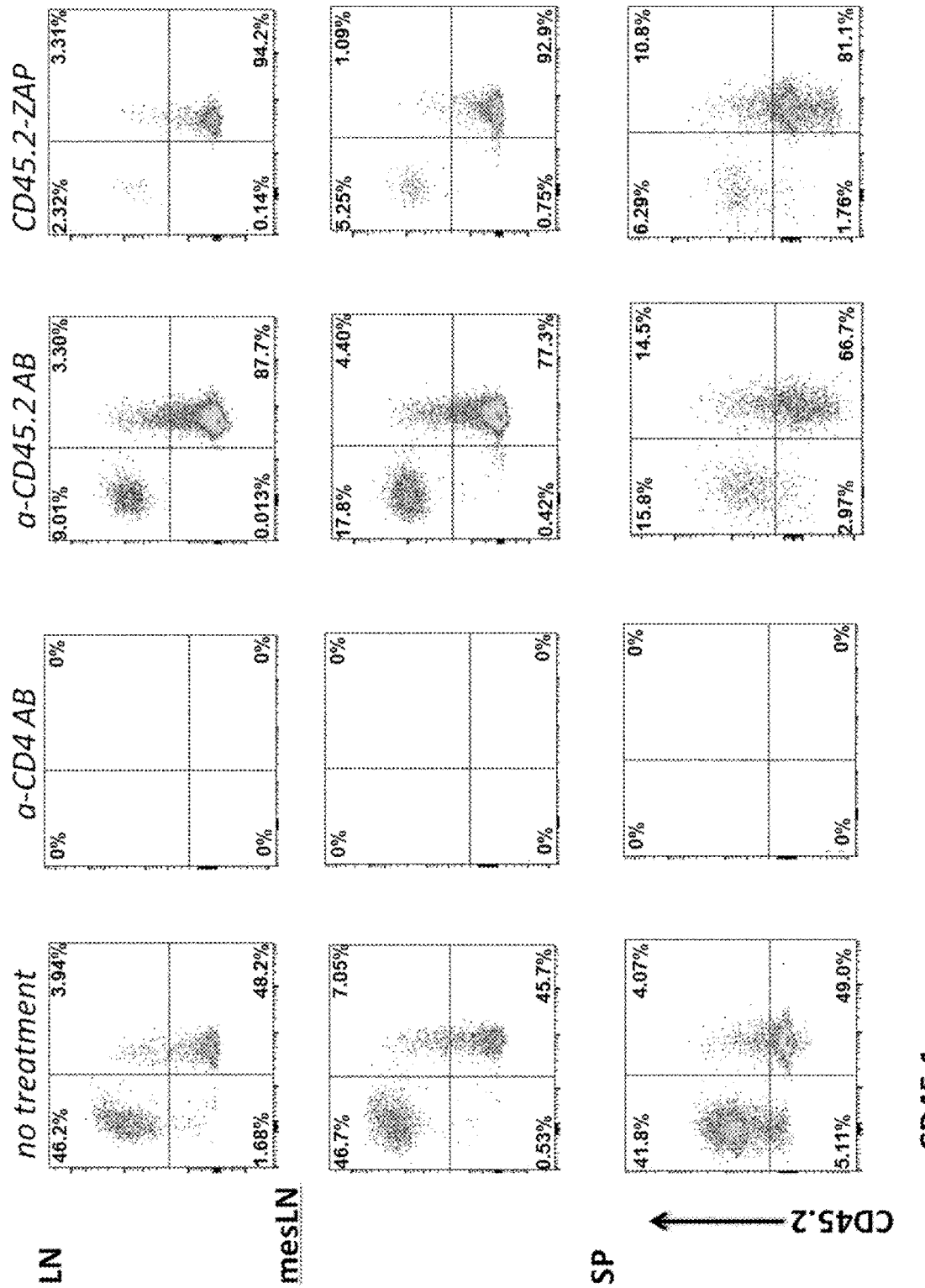

FIG. 27 shows selective depletion of CD45.2+ cells in vivo: lymphoid organs. Same setup as in Fig. xy but analysis of lymph nodes and spleen. Analysis of the presence of CD45.1+ and CD45.2+ T cells in lymph nodes (LN), mesenteric lymph nodes (mesLN) and spleen (SP) as described in Materials & Methods. As observed for peripheral blood, the 1:1 ratio of CD45.1+/CD45.2+ cells persisted in all 3 organs analyzed (no treatment). Non-selective depletion with anti-CD4 mAb depletes CD45.1+ andCD45.2+ T cells in all organs. In contrast, administration of anti-CD45.2 mAb (with or without toxin) selectively depletes CD45.2+ cells leading to a relative enrichment of CD45.1+ cells. Shown are representative flow cytometry plots showing relative numbers. Coupling toxin to CD45.2 mAb leads to more efficient depletion. This demonstrates that selective depletion of cells with very closely related alleles is possible in vivo.

FIG. 28 shows selective depletion of CD45.2+ cells in vivo: Quantification of absolute numbers of T cells in lymphoid organs. Same setup as in FIG. 25 but analysis of lymph nodes (LN) and mesenteric lymph nodes (mesLN).

FIG. 29 shows selective depletion of CD45.2+ cells in vivo: Quantification of absolute numbers of T cells in lymphoid organs. Same setup as in FIG. 25 but analysis of spleen (SP).

FIG. 30 shows selective depletion of CD45.2+ cells in vivo: Quantification of relative numbers of T cells in lymphoid organs. Same setup as in FIG. 25 but analysis of lymph nodes (LN) and mesenteric lymph nodes (mesLN).

FIG. 31 shows Selective depletion of CD45.2+ cells in vivo: Quantification of relative numbers of T cells in lymphoid organs. Same setup as in FIG. 25 but analysis of spleen (SP).

EXAMPLES

Efficient Plasmid-Based Gene Ablation in Primary T Cells

Figure 1B:
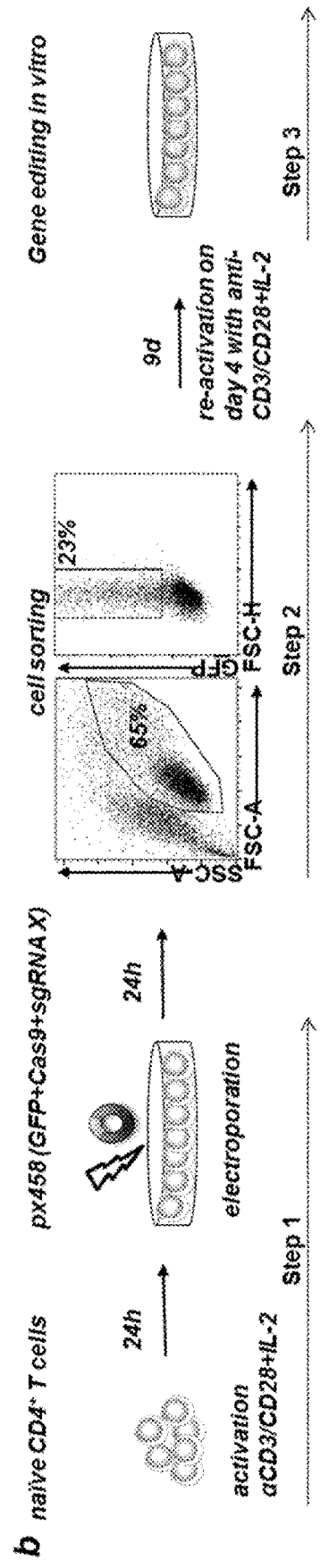
Figure 1D:
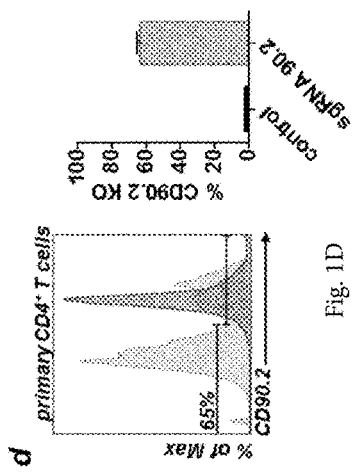
Figure 1F:
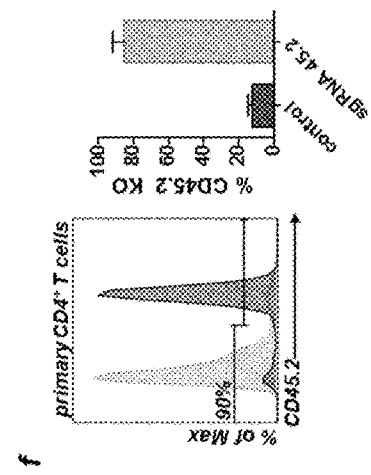
Figure 1H:
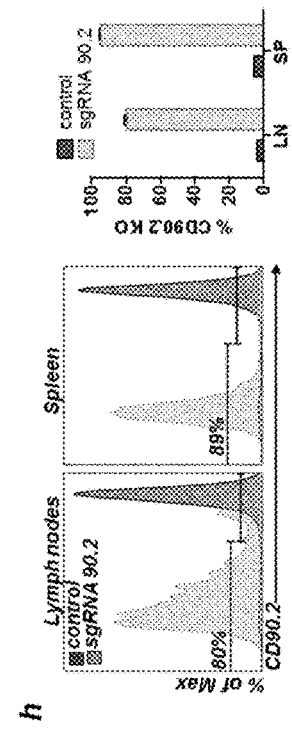
Figure 1C:
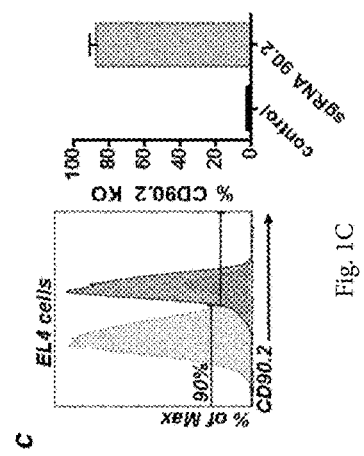
Figure 1E:
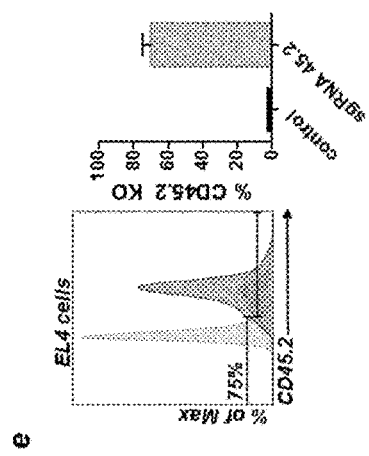
Figure 1G:
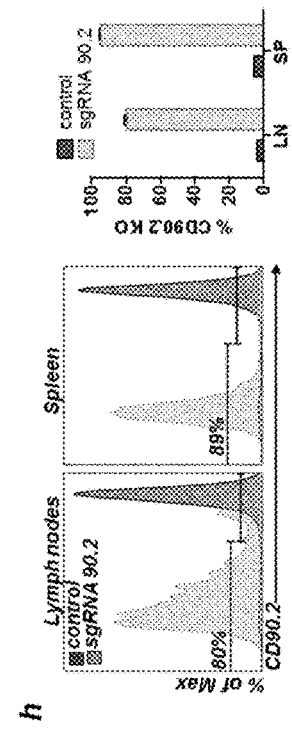

Previous reports successfully used chemically modified guide RNAs (Hendel et al., Nat Biotech 33, 985-989, 2015) or Cas9/sgRNA ribonucleoprotein (RNP) complexes for CRISPR/Cas9-mediated genome editing in human T cells (Schumann, PNAS 112 10437-10442, 2015). DNA based approaches were reported to work poorly if at all. However, many plasmids are waiting to be used if efficient protocols were available (Addgene.org/crispr). In contrast, only very few genome editing nucleases are available as recombinant proteins. Therefore, the inventors aimed to develop a plasmid-based genome editing approach in primary T cells. Based on a successful T cell electroporation protocol (Steiner et al., Immunity 35, 169-181, 2011), the inventors optimized experimental conditions for EL-4 and primary murine CD4+ T cells using a GFP expression plasmid (FIGS. 1A and 1B). The inventors quantified the efficiency of gene editing in single cells for genes encoding cell surface proteins using flow cytometry. Both, in EL-4 cells and primary mouse CD4+ T cells they achieved very high deletion efficiencies for CD90.2 and Ptprc whose gene product, CD45, was lost in the vast majority of cells compared to the control conditions (FIG. 1C-F). Using the aforementioned protocol for multiplexed gene editing almost half of the cells lost CD90.2 and CD45.2 expression simultaneously, indicating homozygous deletion of both genes (FIG. 1G). Next, the inventors wondered if the editing could also occur in vivo. To this end they adoptively transferred (AT) electroporated cells into lymphodeficient RAG KO mice immediately after GFP sorting. Ten days post AT, they observed that CD90.2 deletion on T cells recovered from lymph nodes (LN) and spleen (SP) was comparable to the gene editing in vitro (FIG. 1H). The recovered cells were viable and had expanded substantially. Thus, this plasmid-based approach enables efficient gene ablation in T cells in vitro and in vivo.

Targeted Introduction of Point Mutations in Primary T Cells

Figure 2A:
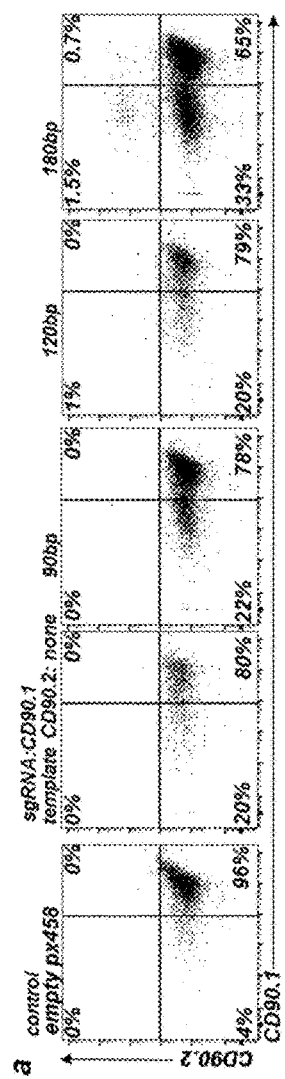
Figure 2B:
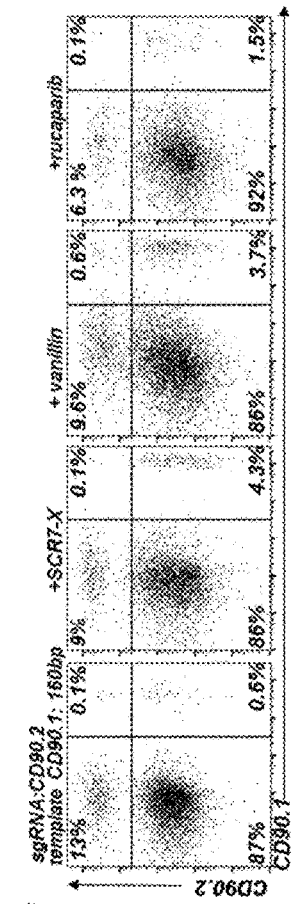
Figure 2C:
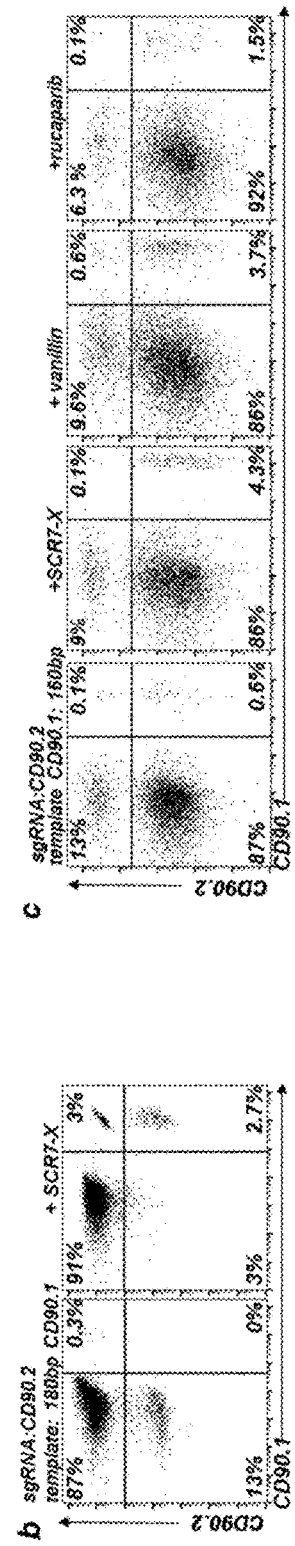

Gene editing-induced DNA double strand breaks (DSBs) are mostly repaired by non-homologous end joining (NHEJ) which results in random indels. In contrast, DSB repair by HDR allows controlled genome editing and is therefore desirable for clinical applications but occurs much more rarely (Wang et al., Annual review of biochemistry 85, 227-264, 2016). However, the absence of suitable assays to readily quantify HDR events hinders improvement of HDR efficiencies in cells in general and particularly in primary cells. In order to allow rapid assessment of HDR efficiencies in primary CD4+ T cells the inventors designed a novel assay (FIG. 5A). Two isoforms of murine CD90 (CD90.1 and CD90.2) differ by a single nucleotide (nt) resulting in a single amino acid (aa) difference (CD90.1: arginine (Arg); CD90.2 glutamine (Gln)) (FIG. 5B) that can be distinguished by two monoclonal antibodies (mAb) (Williams et al., Science (New York, N.Y.) 216, 696-703, 1982). The inventors hypothesized that successful DNA editing from one isoform to the other could be quantitated using the two isoform specific mAbs. To establish the isoform switching assay (ISA) they tested if T cells from Balb/c mice (CD90.1/CD90.1) could be converted to express the CD90.2 isoform by providing 3 different sizes of HDR templates (FIG. 5C). The sgRNA targeting CD90.1 alone resulted in gene deletion in about 20% of successfully transfected cells (FIG. 2A). Provision of a single stranded DNA (ssDNA) template encoding CD90.2 resulted in the detection of a few cells heterozygous for CD90.1/CD90.2 and cells homozygous for CD90.2 (FIG. 2A). The inventors only detected isoform switching with the longest ssDNA used (180 bp, i.e. 90 bp flanking the mutation 5' and 3') but not with the shorter templates (FIG. 2A and FIG. 5C). Thus, isoform switching of endogenous genes can be used to quantify HDR as well as NHEJ in single cells. Given the relatively low HDR efficiency the inventors decided to further optimize the system and tested if the assay works more generally by reversing CD90.2 to CD90.1 isoforms. Using CD4+ T cells from C57BL/6N mice (CD90.2/CD90.2) they confirmed the feasibility of monitoring the introduction of a point mutation by flow cytometry (FIG. 2B). The frequency of heterozygously or homozygously edited T cells remained low however. Therefore they transiently exposed the cells to the DNA ligase IV inhibitor SCR7 that inhibits NHEJ. As reported previously, the presence of SCR7-X increased HDR efficiency >10-fold (FIG. 2B). Next, mutating HDR templates demonstrated that HDR templates with a mutant PAM sequence increased HDR efficiency about 2-fold while additional mutations failed to further increase HDR efficiency (FIG. 5D). Therefore, the inventors used PAM mutated sequences for most of the subsequent experiments. Since inhibiting NHEJ by SCR7-X substantially enhanced HDR (FIG. 2B), the inventors compared several small molecules which interfere with the NHEJ pathway or which directly enhance HDR to find the best HDR enhancing strategy for T cells. Along with SCR7-X, the DNA PK inhibitor vanillin and the PARP1 inhibitor rucaparib yielded the strongest increase in HDR frequency (FIG. 2C). Other compounds (veliparib, L75507 (Ref Yu et al./Qi, Cell Stem Cell 2015), luminespib, RS-1 (Ref Song, Nat Comm, 2016) and the vanillin derivatives A14415, A1359 and L17452 (Ref Durant, Karran, Nucl Acid Research 2003)) increased HDR less or were toxic. Since vanillin resulted in the strongest increase in HDR and in addition was the only water soluble compound, the inventors focused on vanillin for subsequent experiments.

Figure 2D:
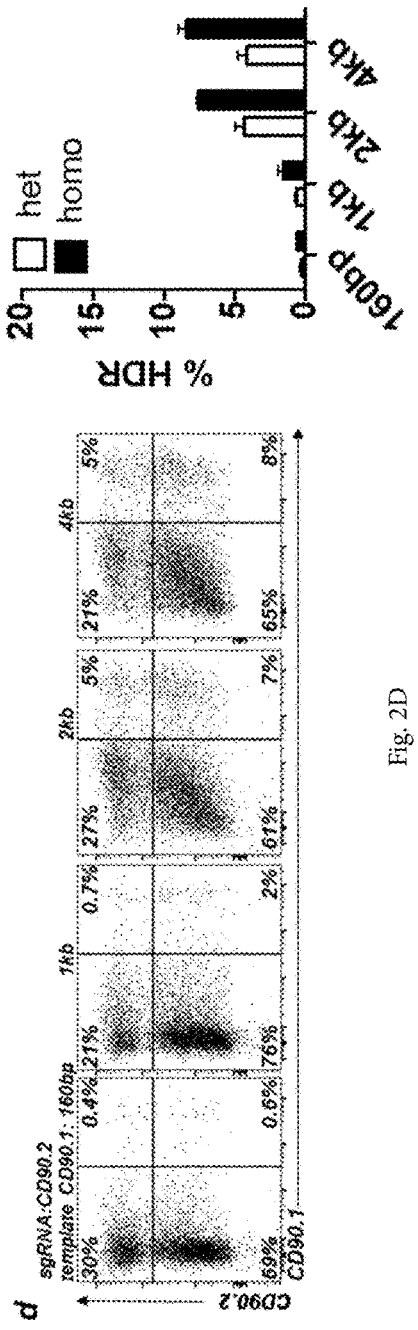

The next parameter the inventors evaluated was the length of the repair template. While recent gene editing reports frequently used relatively short ssDNA templates (usually <200 bp) the results of the inventors (FIG. 2A) suggested that longer templates might result in higher HDR efficiencies. Furthermore, the arms of homology for gene targeting in embryonic stem (ES) cells are usually much longer (several kb). Indeed, increasing the arms of homology of a circular dsDNA (plasmid) CD90.1 HDR template correlated positively with HDR efficiency (FIG. 2D). The largest increase was found between 1 kb and 2 kb homology (FIG. 2D). In addition, the inventors noticed the highest HDR frequencies in large, blasting cells in which more than 30% had undergone HDR with 4 kb of homology (FIG. 5F). Importantly, the optimized conditions yielded similar HDR frequencies in primary mouse CD4+ T cells. Up to a quarter of the blasting primary T cells homozygously expressed CD90.1 (FIG. 2E). Of note, the HDR enhancing effect of vanillin was more pronounced for shorter templates (160 bp, 1 kb) than for the long (2 kb, 4 kb) templates (FIG. 2F). Therefore, the inventors wondered if a long template without NHEJ inhibition could yield a comparable HDR frequency than shorter templates with NHEJ inhibitors. A direct comparison showed that 2 kb and 4 kb templates without vanillin resulted in much higher HDR frequencies than the 160 bp and the 1 kb template in the presence of vanillin (FIG. 2G). Thus, for clinical applications long dsDNA templates might be a valid alternative to NHEJ inhibitors that could have unwanted side effects.

Finally, the inventors examined what effect the cut site relative to the mutation exerts on HDR efficiency (FIG. 2H). To this end, they compared the sgRNACD90.2 that binds directly on the mutation site with a $2^{nd}$ sgRNA (sgRNACD90.2-A) that binds 50 bp away from the mutation (FIG. 5G). Both sgRNAs efficiently induced DSBs with deletion of CD90.2 in the majority of cells (FIG. 2H). In agreement with previous studies (Paquet et al., Nature 533, 125-129, 2016) the use of the distant sgRNA (sgRNACD90.2-A) completely abolished HDR repair with short (160 bp and 1 kb) templates (FIG. 2G). In contrast, the long templates (2 kb, 4 kb) partially restored HDR. Thus, ISA is a simple, rapid and cost-effective system to quantify HDR efficiency. Long dsDNA templates are worth considering in order to increase HDR efficiency, to reduce the requirement for NHEJ inhibitors and to overcome cut-to-mutation limitations.

Enrichment of HDR-Edited Cells through Monitoring of Isoform Switching of a Surrogate Cell Surface Marker To test if the optimized conditions found with the CD90 ISA are more universally applicable, the inventors turned to Ptprc, a gene from which multiple CD45 splice forms are expressed. Two isoforms, CD45.1 and CD45.2 can be discriminated by two mAbs. In contrast to CD90.1 and CD90.2 however, the precise epitope recognized by mAb anti-CD45.1 (clone A20) and mAb anti-CD45.2 (clone 104) is unknown. The extracellular domain of CD45.1 and CD45.2 differs by 6 nt, but it is unknown which epitope is being recognized as allelic difference. One nt substitution is silent while the other five change the aa sequence (FIG. 3A). Therefore, the inventors hypothesized that editing the five candidate nt substitutions individually or as combinations directly in primary T cells could be used to fine map the epitopes being recognized by the two known mAbs. They grouped the five candidate nt into three genomic regions covered by three ssDNA templates (SEQ ID NO 033, SEQ ID NO 035, SEQ ID NO 037) each encoding partial CD45.1 sequences and designed 3 sgRNAs (SEQ ID NO 003, SEQ ID NO 004, SEQ ID NO 005) binding as close as possible to the SNPs (FIG. 3A). Using the T cell HDR protocol they found that all three sgRNAs led to efficient cuts (FIG. 3B). Exchange of a single nt within region R1 enabled binding of mAb CD45.1 and prevented binding of mAb CD45.2 in some cells. In contrast, editing R2 and R3 did not result in anti-CD45.1 binding (FIG. 3B). A longer repair template increased HDR efficiency and confirmed this result (FIG. 3C). Sanger sequencing of all 4 purified populations confirmed correct editing (FIG. 6). Thus, the Lys277Glu substitution is necessary and sufficient to explain reactivity of the CD45.1 epitope with mAb CD45.1 clone A20. These results demonstrate the feasibility of epitope mapping in primary cells, i.e. in the native context of an endogenous antigen.

Figure 3E:
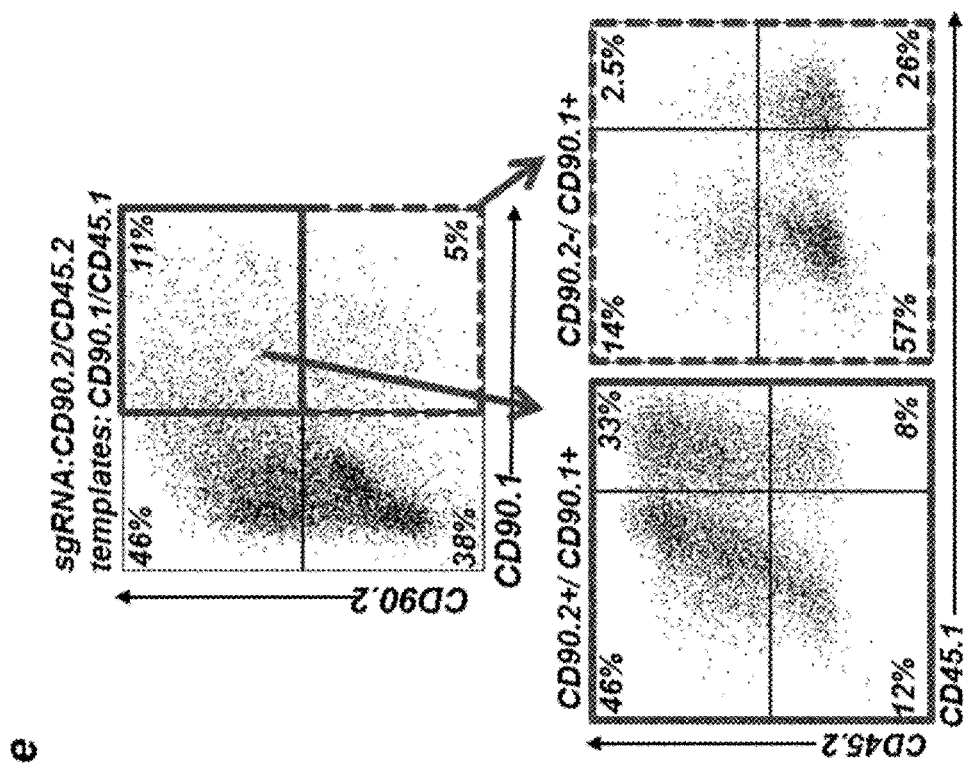
Figure 3D:
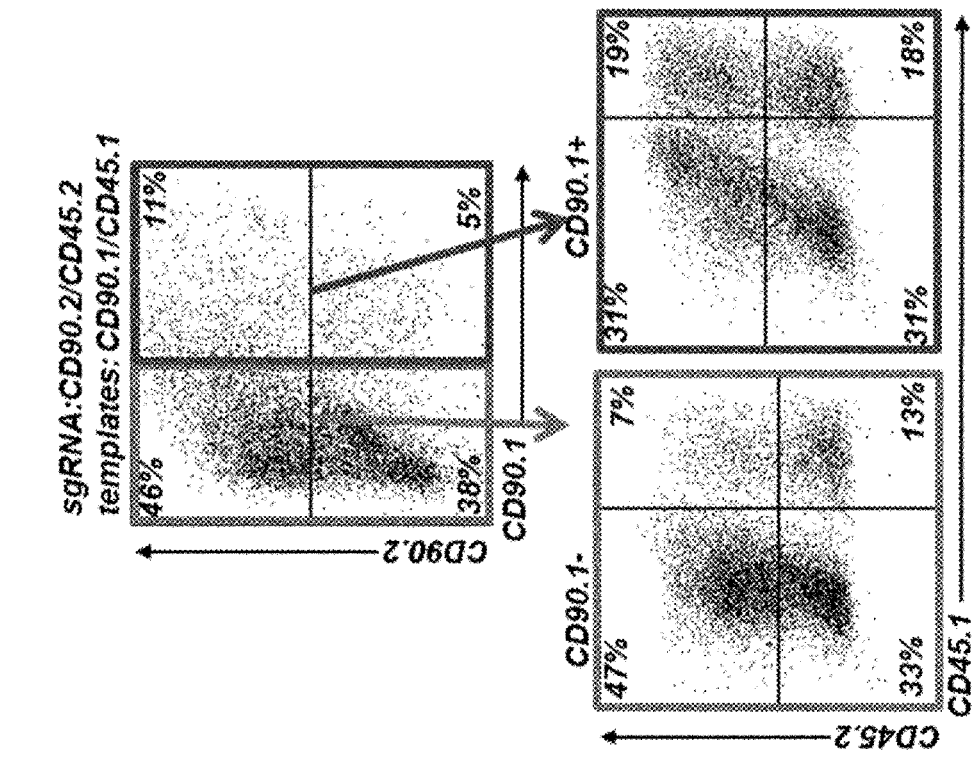

Next, the inventors wondered if the CD90 ISA and CD45 ISA could be combined to quantitate multiplexed HDR in single cells. To this end, they electroporated plasmids encoding sgRNAs targeting CD90.2 and CD45.2 along with repair templates for CD90.1 and CD45.1. Cutting efficiency under these conditions was a bit lower than with fewer plasmids, but HDR for CD90 and CD45 individual alleles was very efficient. The inventors then sought to determine if two HDR events in the same cell are independent from each other or linked. They found a 2-fold enrichment of cells switching CD45.2 to CD45.1 in cells that had switched CD90.2 to CD90.1 compared to cells that remained CD90. V (FIG. 3D). Importantly, a third of the CD90.2$^+$/CD90.1$^+$ heterozygous cells were also heterozygous for CD45.2$^+$/CD45.1$^+$ (FIG. 3E). Similarly, the highest relative frequency of homozygous CD45.1* cells was found among cells that were also homozygous for CD90.1+ (FIG. 3E). Thus, isoform switching at one locus is linked to isoform switching at another locus. Unexpectedly, this link is quantitative with respect to the zygosity of HDR, i.e. a cell which underwent monoallelic HDR is more likely to undergo monoallelic HDR at a second locus and a cell which did bi-allelic HDR is more likely to have used bi-allelic HDR to repair a second locus. The inventors therefore propose that assessment of a surrogate marker HDR gene editing event could be exploited to enrich and/or select for zygosity of HDR gene editing at a second gene locus of interest for which no marker is available.

Gene Correction of Scurfy Cells

Finally, the inventors sought to apply the newly developed T cell editing protocol to correct a monogenic disease. The prototypic mutations causing human immunodysregulation polyendocrinopathy enteropathy X-linked (IPEX) syndrome are mutations in the Foxp3 gene which encodes a transcription factor critical for T regulatory cell (Treg) function and maintenance of immune regulation (Josefowicz, et al., Annual review of immunology 30, 531-564, 2012). Mutations in murine Foxp3 lead to a very similar syndrome termed scurfy (Ramsdell et al., Nature reviews. Immunology 3314, 343-349, 2014). A 2 bp insertion in Foxp3 exon 8 results in a frameshift leading to the scurfy phenotype. Affected mice die within weeks after birth due to multi-organ failure caused by a complete breakdown of immune tolerance resulting in uncontrolled activation of the immune system, tissue infiltration and immune-mediated destruction of multiple organs. Foxp3-deficient mice with a genetically marked Foxp3 locus contain Treg "wanna-be's" indicating that cells destined to become Foxp3+ Treg which are actively transcribing the Foxp3 locus are present in scurfy mice but due to the absence of Foxp3 they cannot be identified as Treg and they lack suppressive function. Thus, the inventors hypothesized that gene correction of scurfy T cells should lead to restoration of Foxp3 protein expression.

Figures 4A, 4B:
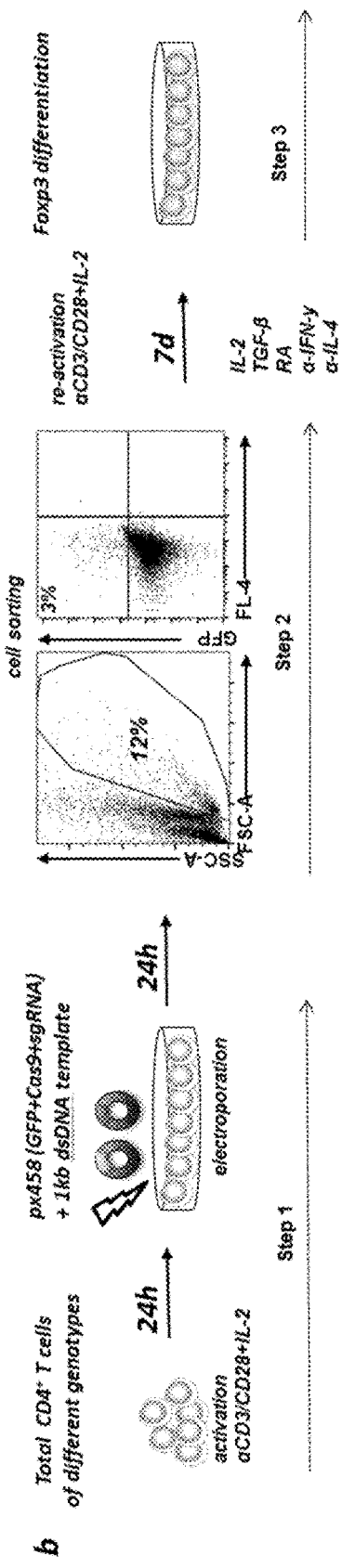
Figures 4C, 4D:
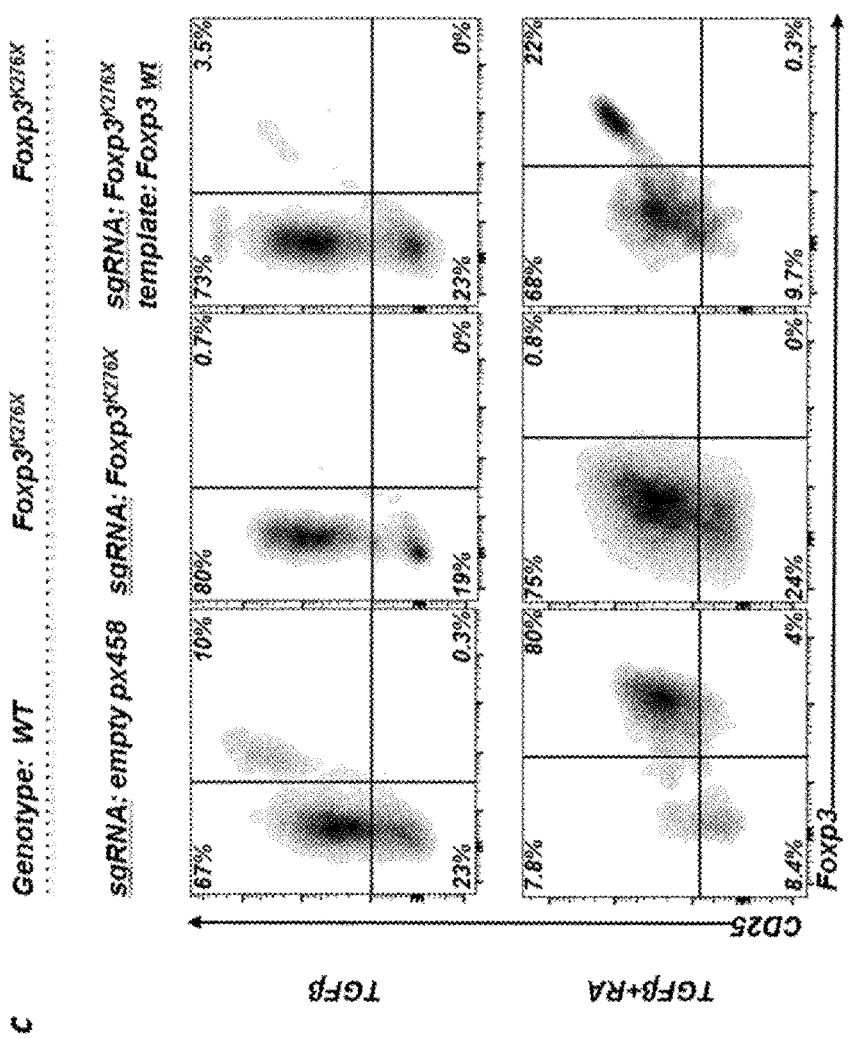

To test their hypothesis they used T cells from scurfy mice and gene targeted mice that bear a Foxp3$^{K276X}$ mutation ("Foxp3 KO") that recapitulates a known human IPEX disease-causing Foxp3 mutation (Ramsdell, Nature reviews. Immunology 14, 343-349, 2014). Therefore, repairing this mutation is clinically relevant. Both mutations abolish Foxp3 protein expression. They adjusted the HDR-based gene repair approach to T cells from diseased mice and examined the in vitro Treg differentiation potential of gene-corrected Foxp3 KO cells by providing the Foxp3 inducing signals TGFr alone or combined retinoic acid (RA) and TGFn (Chen et al., The Journal of Experimental Medicine 198, 1875-1886, 2003) (FIG. 4B). After gene repair and stimulation with TGFn alone 10% of wildtype T cells became CD25$^+$Foxp3$^+$ while no Foxp3$^+$ cells were detected in Foxp3$^{K276X}$ CD4+ T cells transfected with sgRNAFox3$^{K276X}$ alone, in contrast, the Foxp3 wildtype repair template restored Foxp3 expression in 3.5% of the cells (FIG. 4C, top panel). Exposing electroporated T cells to TG Fr+RA resulted in 80.2% Foxp3 expression in wild-type T cells, no detectable Foxp3 expression in Foxp3$^{K276X}$ CD4+ T cells without HDR repair template and 22.1% Foxp3+ T cells in Foxp3$^{K276X}$ CD4$^+$ T cells repaired with the wildtype Foxp3 HDR template (FIG. 4c, lower panel). Comparable results were obtained with scurfy cells (data not shown). Finally, the inventors sought to enrich correctly repaired cells using multiplexed HDR as described in FIG. 3D. They used CD45 as a surrogate cell surface marker to monitor isoform switching. Indeed, CD25$^+$Foxp3$^+$ cells were substantially enriched among CD45.1+ cells compared to CD45. T cells (FIG. 4D). In summary, the inventors established conditions to repair Foxp3 in primary T cells and demonstrate the applicability of multiplexing HDR to enrich gene-corrected cells.

Methods

Gene editing in primary murine CD4* T cells

Naive CD4+ T cells were purified (>96% purity) from C57BL6N or Balb/c mouse spleen (SP) and lymph nodes (LN) using the EasySep™ Mouse Naive CD4+ T Cell Isolation Kit (STEMCELL Technologies Inc). Complete RPMI media (CM RPMI) was generated by supplementing RPMI (Sigma) with 10% heat-inactivated FCS (Atlanta biologicals), 2 mM Glutamax (Gibco), 50 pM r-mercaptoethanol (Gibco), 10 mM HEPES (Sigma) and non-essential amino acids (Gibco). For T cell activation, 2×10⁶ naive CD4⁺ T cells were plated in a 24-well plate (Corning) coated with monoclonal antibodies (mAb) anti-CD3 (hybridoma clone 2C11, 1 pg/ml) and anti-CD28 (hybridoma clone PV-1, 0.5 pg/ml, both BioXcell) for 24 h at 37° C. with 5% $CO_2$ in the presence of 50 IU/ml recombinant human Interleukin-2 (rhIL-2) (RD systems) in the presence of plate-bound monoclonal antibodies (mAb) anti-CD3 (hybridoma clone 2C11, 1 pg/ml) and anti-CD28 (hybridoma clone PV-1, 0.5 pg/ml) (BioXcell). 24 h later T cells were harvested and washed with PBS. 2×10⁶ activated T cells were electroporated with the Invitrogen Neon© Transfection System at the following conditions: voltage (1550 V), width (10 mS), pulses (3) (Invitrogen), 100 pl tip, buffer R (for all electroporations buffer R was used). Cells were transfected with 6.5 pg of empty plasmid px458 (Addgene plasmid number 48138) or the plasmids described in Figure legends and Suppl. Table 1. (Addgene plasmid numbers 82670-82677). For HDR cells were co-transfected with 12 pg (or 1200 ng, 600 ng, 250 ng) HDR template (if plasmid: Suppl. Table 3; Addgene 82661-82669) or 10 pl of 10 pM stock ssDNA template from (IDT). After electroporation cells were plated in 24-well plate in 650 pl CM RPMI with 50 IU/ml rhIL-2 in the presence of plate-bound mAbs at half the concentrations used for the initial activation, i.e. anti-CD3 (0.5 pg/ml) and anti-CD28 (0.25 pg/ml). Cells were transfected with 6.5 pg of empty plasmid px458 (Addgene plasmid number 48138) or the plasmids comprising the dsDNA repair template. For HDR cells were co-transfected with 12 pg (or 1200 ng, 600 ng, 250 ng) HDR template (if plasmid) or 10 pl of 10 pM stock ssDNA template from (IDT). GFP⁺ and GFP' cells were sorted 24 h post transfection using a FACSAria Cell Sorter to >98% purity (BD Biosciences). Immediately after sorting cells were plated in 96 well flat bottom plates without activating antibodies in 250 pl CM RPMI supplemented with 50 U rhIL-2/ml. For the HDR experiments sorted ceils were cultured in the presence of NHEJ inhibitors or HDR enhancers for the following 24 h in order to enhance the HDR (as indicated in figure legends). Cells were re-activated with plate bound anti-CD3 (0.5 pg/ml) and anti-CD28 (0.25 pg/ml) on day 4 post GFP sorting and expanded for the following 9 days in culture until the end of the experiment.

Gene Editing in EL-4 Cells

EL-4 cells were purchased from ATCC (ATCC TIB-39™) and were grown in RPMI (Sigma) supplemented with 10% heat inactivated fetal bovine serum (Atlanta biologicals), 2 mM Glutamax (Gibco) and 50 pM p-mercaptoethanol (Gibco). FACS analysis confirmed homozygous CD90.2 and CD45.2 expression by EL4 cells comparable to that of primary T cells. 2×10⁶ EL-4 cells were electroporated with the Invitrogen Neon Transfection System at the following conditions: voltage (1080 V), width (50 ms), number of pulses (1) 100 pl tip (Invitrogen). After electroporation cells were plated in 24 well plates in 650 pl CM RPMI. Amount of plasmids and concentrations of HDR templates were the same as for primary T cells described above. GFP⁺ and GFP' cells were sorted 24 h post transfection using a FACSAria Cell Sorter to a purity of >98% (BD Biosciences). Immediately after sorting cells were plated in 96 well flat bottom plates. For the HDR experiments, sorted cells were cultured in the presence of NHEJ inhibitors or HDR enhancers for the following 24 h in order to enhance the HDR. Cells were then expanded for the next 9 days in culture.

Foxp3 Repair Protocol

Although the majority of T cells from $Foxp3^{K276X}$ C57BL/6 mice are phenotypically highly activated, T cells had to be re-activated in vitro for electroporation. Without in vitro re-activation we did not obtain GFP expressing T cells after electroporation (data not shown). We adjusted the protocol used to electroporate primary T cells from healthy mice by reducing the TCR stimulation in order to obtain a good balance between cell viability and transfection rate. In addition, we used total CD4+ T cells as a starting population because of the low numbers of naive T cells (data not shown). Total CD4+ T cells were purified from $Foxp3^{K276X}$ (C57BL/6) or B6.Cg-$Foxp3^{s/}$7J (C57BL/6; data not shown) from pooled SP and LN using the EasySep™ CD4+ T Cell Isolation Kit (>96% purity) (STEMCELL Technologies Inc). For T cell activation, 2×10⁶ CD4+ T cells were plated in a 24-well plate coated with anti-CD3 (clone 2C11; 0.5 pg/ml) and anti-CD28 (clone PV-1; 0.25 pg/ml) (BioXcell) for 24 h at 37° C. with 5% $CO_2$, with 501 U rhIL-2/ml (RD systems). 24 h later T cells were harvested and washed with PBS. 2×10⁶ activated T cells were electroporated with the Invitrogen Neon® Transfection System at the following conditions: voltage (1550V), width (10 ms), number of pulses (3) (Invitrogen). Cells were transfected with 6.5 pg of plasmid (p240J_TJ_sgRNAFoxp3K276X and p236JLTJ sgRNAFoxp3sf/J; Addgene numbers 82675 and 82676) and 12 pg of the dsDNA wildtype Foxp3 repair template (Addgene 82664). After electroporation cells were plated in 24 well plate with 50 IU/ml of rhiL-2 in the presence of plate bound mAbs at half the concentrations used for the initial activation, i.e. 0.25 pg/ml anti-CD3 and 0.12 pg/ml anti-CD28 in 650 pl CM RPMI. GFP⁺ and GFP~ cells were sorted 24 h post transfection using a FACSAria Cell Sorter to a purity >98% (BD Biosciences). Immediately after cell sorting the purified cells were re-activated with plate bound anti-CD3 (0.5 pg/ml) and anti-CD28 (0.25 pg/ml) and expanded until the end of the experiment in the presence of rhIL-2 (250 IU/ml), TGFn (5 ng/ml, RD Systems), anti-IFNy (10 mg/ml, BioXcell), anti-IL-4 (10 mg/ml, BioXcell) and Retinoic Acid (10 mM, Sigma) as indicated in the figure legend.

Mice

C57BL/6N (Charles River stock No: 027) were purchased at the Charles River laboratory. Balb/c (Jackson laboratory Stock No: 000651) mice were a generous gift from Werner Krenger (Basel University Hospital). $Foxp3^{K276X}$ C57BL/6 (Jackson laboratory Stock No: 019933) mice were a generous gift from Ed Palmer (Basel University Hospital). B6.Cg-$Foxp3^{s/}$/J mice were purchased from the Jackson laboratory (Stock No: 004088). B6.12957-Rag/j (Jackson laboratory Stock No: 002216) mice were obtained from the Swiss Immunological Mouse Repository (SwImMR). All animal work was done in accordance with the federal and cantonal laws of Switzerland. The Animal Research Commission of the Canton of Basel-Stadt, Switzerland, approved animal research protocols.

Flow Cytometry and Antibodies

Cells were stained and then acquired on a BD Fortessa (BD Biosciences) and analyzed with FlowJo software (Tree Star). Surface phenotype staining was done with the following fluorochrome-conjugated mAbs: anti-CD90.2 (clone 53-2.1), anti-CD90.1 (clone OX7), anti-CD45.2 (clone 104), anti-CD45.1 (clone A20), (all eBioscience), anti-CD4 (clone RM4-5), anti-CD25 (clone PC61), (both Biolegend). The expression of Foxp3 (clone FJK-16 s) (eBioscience) was determined by intracellular staining performed according to the manufacturers' protocols. Prior to staining of the surface antibodies cells were stained for live/dead discrimination with Zombie UV dye (Biolegend).

Design of sgRNA

DNA sequences of all sgRNAs, primers and HDR templates used in this paper are listed as 5'-3' sequences in the Supplementary information. sgRNAs were designed using the CRISPRtool (http://crispr.mit.edu) and sgRNA Scorer 1.0 sg (https://crispr.med.harvard.edu). The sgRNA sequences with their respective scores are listed in Suppl. Table 1. For CD45 epitope mapping two sgRNAs were designed per candidate region and results obtained with the ones closest to the SNP of interest are shown in the main figures. However, all 6 tested sgRNAs cut efficiently and region R1 switched epitopes with both sgRNAs (data not shown). The cut-to-mutation difference did not play a role.

Cloning of sgRNAs into px458 Plasmid pSpCas9(BB)-2A-GFP (PX458) was a gift from Feng Zhang (Addgene plasmid #48138). Cloning into px458 was modified from Schumann et al., PNAS 112 10437-10442 (2015). The px458 plasmid was digested with BbsI for 1.5 h at 37° C. followed by heat inactivation for 20 min at 65° C. The digested plasmid was gel-purified using the Nucleospin gel and PGR clean-up purification kit according to the manufacturer's recommendations (Macherey-Nagel). The forward and reverse oligonucleotides (oligo) of each sgRNA were diluted at 100 pM in $H_2O$. To phosphorylate and anneal the oligos, 2 pl of each oligo were mixed with T4 ligation buffer and T4 PNK to a final volume of 20 pl and incubated for 30' at 37° C. (phosphorylation) followed by 5' at 95° C. and then ramping down the temperature to 20° C. at -1° C./min (annealing). The annealed and phosphorylated oligos were diluted 1:200 in $H_2O$. Ligation reactions for each sgRNA were performed by mixing 100 ng of the digested and purified px458 plasmid with 2 pl of the diluted phosphorylated and annealed oligos, T4 ligation buffer and T4 ligase in a final volume of 20 pl. Ligation was carried out for 1 h at 22° C. Bacterial transformation was performed by mixing 5 pl of the ligation reaction with 50 pl ice-cold chemically competent JM109 bacteria. The mixture was incubated on ice for 30 min, followed by a heat-shock at 42° C. for 30" and a subsequent 2' incubation on ice. Then, 200 pl of SOC medium (Sigma) was added and bacteria were grown for 1 h at 37° C. All the transformation reaction was plated on LB plates containing 50 pg/ml ampicillin. The plates were incubated overnight at 37° C. Colonies were checked for correct insertion of the sgRNA by PCR colony screening followed by sequencing. Plasmids are available from Addgene.org (Addgene plasmid numbers 82670-82677).

PCR Colony Screening for Cloning into Addgene Plasmid px458

Bacteria from 2 colonies per plate were picked with a pipette tip and mixed in PCR tubes with $H_2O$, REDTaq® ReadyMix™ PCR Reaction Mix (Sigma) and specific primers (forward primer GAGGGCCTATTTCCCATGATTCC, SEQ ID NO 028; reverse primer TCTTCTCGAAGACCCGGTG, SEQ ID NO 029). PCR was performed using an annealing temperature of 64.9° C. and 35 cycles. Positive colonies (with sgRNA insertion) will display no PCR amplicon whereas negative colonies will show a 264 bp amplicon.

Plasmid Sequencing

Two colonies were picked from each LB plate using a pipette tip and inoculated into a 5 ml culture of LB medium supplemented with 50 pg/ml ampicillin. The cultures were grown overnight at 37° C. Plasmid DNA from the culture was isolated by GenElute Plasmid Miniprep kit (Sigma) following the manufacturer' recommendations. Correct insertion of the sgRNA was verified by sequencing the plasmid DNA using a U6-forward primer (ACTAT-CATATGCTTACCGTAAC, SEQ ID NO 0043). HDR repair templates DNA repair templates were designed as homologous genomic DNA sequences flanking the sgRNA binding sites. Unless noted otherwise the sgRNAs were centered as much as possible with respect to the repair templates resulting in symmetric arms of homology. Silent mutations (i.e. not altering the amino acid sequence) were introduced into the PAM sequences unless noted otherwise. Short ssDNA templates were purchased from IDT. Lyophilized ssDNA oligos were reconstituted to 10 pM in ddH2O. For specific sequences see Suppl. Table 2. dsDNA templates for CD90.1, CD45.1 and Foxp3 (160 bp, 1 kb, 2 kb and/or 4 kb) were purchased from Genscript as synthetic DNA cloned into pUC57 (for specific sequences see Suppl. Table 3). Maxi preps (Sigma) were prepared for each of the plasmids prior to the use in the experiments. For all HDR experiments circular HDR template plasmids were used since we obtained better results compared to the use of linearized plasmids (data not shown). Plasmids containing HDR templates are available from Addgene.org (Addgene plasmid numbers 82661-82669).

Small Molecules

The following NHEJ inhibitors were used to enhance HDR: vanillin (Durant, Nucl Acid Res, 2003) reconstituted in $H_2O$, 300 pM final concentration (Sigma cat #V1104); SCR7-X in DMSO, 1 pM final (Xcess Biosciences cat #M60082). Since we purchased SCR7-X from Xcess Biosciences we refer to this compound as "SCR7-X" as recently suggested (Greco et al., DNA Repair 2016). Rucaparib/AG-014699/PF-01367338, in DMSO, 1 pM final (Selleckchem cat #S1098); veliparib/ABT-888 in DMSO, 5 pM final (Selleckchem cat #S1004); RS-1 (Song et al., Nat Comm 2016), in DMSO, 7.5 pM final (MerckMillipore cat #553510); RS-1 in DMSO, 7.5 pM final, (Sigma cat #R9782); Luminespib/AUY-922/NVP-AUY922 in DMSO, 1 pM final (Selleckchem cat #S1069); L-755,507 in DMSO, 5 pM final (Tocris cat #2197); vanillin derivatives (Durant, Nucl Acid Res, 2003) 6-nitroveratraldehyde in DMSO, 3 pM final (Maybridge cat #11427047), 4,5-dimethoxy-3-iodobenzaldehyde in DMSO, 3 pM final (Maybridge cat #11328426); 6-bromoveratraldehyde in DMSO, 3 pM final (Maybridge cat #11480124).

Genomic DNA Sequencing

Genomic DNA from different sorted cell populations (e.g. $CD45.2^+$/CD45.T, $CD45.2^+$/$CD45.1^+$, $CD45.27CD45.1^+$, and CD45.27CD45.T) was extracted by incubating the cells with the extraction buffer (WOrnM Tris pH 8.5, 5 mM Na-EDTA, 0.2% SDS, 200 mM NaCl and 100|jg/ml Proteinase K; all from Sigma) for 1 h at 56° C. After 15' heat inactivation of the proteinase K at 95° C., the samples were mixed with an equal volume of isopropanol and inverted several times to facilitate DNA precipitation. After a 2' centrifugation, the supernatant was removed and, the pellet washed with 70% ethanol. DNA was pelleted by centrifugation, air dried, resuspended in milliQ water and the concentration was measured with a NanoDrop device (Witec). PCR primers including BamHI (forward TAAGCAG-GATCCATTCCTTAGGACCACCACCTG, SEQ ID NO 044) and SalI (reverse TGCTTAGTCGACACACCGCGA-TATAAGATTTCTGC, SEQ ID NO 045) overhangs were purchased (Microsynth) to amplify a region of 2 kb for the HDR experiment where the sgRNA location is centered within the PCR product. PCRs with 2-6 ng of the different genomic DNA samples were performed using the Phusion polymerase (Thermo Scientific). For the 2 kb fragment the optimal annealing temperature used was 68.1° C. The PCR products were loaded on a 1.5% agarose gel and the bands were purified using the Nucleospin gel and PCR clean-up purification kit according to the manufacturer's recommendations (Macherey-Nagel). The purified PCR products (160 ng) were digested with BamHI and SalI using BamHI buffer for 1.5 h at 37° C. The digested PCR products were loaded on a 1.5% agarose gel and the bands were purified using the Nucleospin gel and PCR cleanup purification kit according to the manufacturer's recommendations. 90 ng of the digested and purified 2 kb PGR amplicons were ligated for 1 h at 22° C. with 50 or 100 ng pGEM3Z plasmid which had been BamHI/SalI digested and purified (Promega), respectively. Transformation was performed by mixing 10 pl of the ligation reaction with 50 pl ice-cold chemically competent JM109 bacteria (purchased from Promega or made using the RbCI protocol http://openwetware.org/wiki/RbCLcompetent cell). The mixture was incubated on ice for 30', followed by a heat-shock at 42° C. for 30" and a subsequent 2' incubation on ice. Then, 200 pl of SOC medium (Sigma) was added and bacteria were grown for 1 h at 37° C. All the transformation reaction was plated on LB plates containing 50 pg/ml ampicillin, 0.1 mM IPTG (Promega) and 35 pg/ml x-Gal (Promega). The plates were incubated overnight at 37° C. From each plate 12 colonies were picked using a pipette tip and inoculated into a 5 ml culture of LB medium supplemented with 50 pg/ml ampicillin. The cultures were grown overnight at 37° C. Plasmid DNAfrom the culture was isolated by GenElute Plasmid Miniprep kit (Sigma) following the manufacturer's recommendations. DNA was sent for sequencing using the T7, SP6 and an internal primer (GAGAAAGCAACCTCCGGTGT, SEQ ID NO 0046) for the 2 kb fragments. Sequences were analyzed using Lasergene (DNASTAR Inc.).

Human T-Cell Isolation and Antibodies:

Human primary T cells were isolated from buffy coats (Blutspendezentrum, Basel) of healthy donors using Lymphoprep™ (Stemcell Technologies) density gradient. Naive $CD4^+$ T cells were pre-enriched with an Easysep Human naive $CD4^+$ T-cell enrichment kit (Stemcell Technologies) according to the manufacturer's protocol. Alternatively, cord blood was used as source for PBMCs, without using naive T cells isolation step, given the high frequencies of naive T cells. Pre and post naive CD4+ T cells enrichment samples were stained with following antibodies in order to assess the purity: aCD4-FITC (OKT-4), aCD25-APC (BC96), aCD45RA-BV711 (H1100), aCD45RO-BV450 (UCHL1), aCD62L-BV605 (DREG-56), aCD3-PerCP (HIT3a) and Zombie-UV viability dye, all purchased at Biolegend.

In brief, for 1 buffy coat of 50 ml: prepare 2×50 ml Falcon tubes with filter and add 16 ml of Lympoprep to each tube, spin @300 g for 1 min. Distribute the blood equally to both 50 ml filter tubes and top up with PBS to 50 ml. Spin @2000 rpm (acc 4, decc 1) for 15 min. Remove some of the serum and discard it. Carefully pool the white buffy coats to a fresh 50 ml Falcon tube. Add sterile PBS to the enriched PBMC fraction to approximately 50 ml and spin @300 g for 5 min. Discard the supernatant and resuspend pellet with 10 ml PBS and top up to 50 ml and spin @300 g for 5 min. Lyse the red blood cells, if needed, with red blood cell lysis buffer, before purification step.

Human T-Cell Transfection Protocol:

Naive $CD4^+$ T cells or total PBMCs from blood or cord blood were used for transfection. For T cell activation, $2 \times 10^6$ cells were plated in a 24-well plate (Corning) coated with monoclonal antibodies (mAbs) a-CD3 (hybridoma clone OKT3, 5 (high), 2.5 (medium), 1 (low) pg/ml) and a-CD28 (hybridoma clone CD28. 2.5 (high), 1 (medium), 0.5 (low) pg/ml, both from Biolegend) for 24 h at 37° C. with 5% $CO_2$ in the presence of 50 IU/ml recombinant human Interleukin-2 (rhIL-2) (RD systems). 24 h later T cells were harvested and washed with PBS. $2 \times 10^6$ activated T cells were electroporated with the Amaxa Transfection System, T-020 program (for plasmid) or using Neon® Transfection System (ThermoFisher) at the following conditions: voltage (1600V), width (10 ms), pulses (3) 100 pl tip, buffer R (for RNPs). Cells were transfected with 6.5 pg of empty plasmid px458 (Addgene plasmid number: 48138) or crRNA:tracerRNA-Atto 550 (IDT) and Cas9 (Berkeley) complex. After electroporation cells were plated in 24-well plate in 650 pl complete media with 50 IU rhIL-2/ml in the presence of platebound mAbs at half the concentrations used for the initial activation, i.e. anti-CD3 (2.5, 1.25, 0.5 pg/ml) and anti-CD28 (1.25, 0.5, 0.25 pg/ml). The expression of $GFP^+$ or $Atto550^+$ cells were assessed 24 h later by using Fortessa analyzer (BD Biosciences).

Cas9 RNP Assembly:

The delivery of a Cas9 ribonucleoprotein (RNP) complex, containing an Alt-R CRISPR crRNA and Atto 550 labeled tracrRNA (both from IDT) and a Cas9 nuclease (from Berkeley), into primary mouse/human T cells or EL4 cells using the Neon® Transfection System (ThermoFisher) were adapted from IDT provided protocol (https://eu.idtdna.com/pages/docs/default-source/CRISPR/idt protocol nep-of-jurkat-rnp-rt crs-10061-prv2-1.pdf?sfvrsn=20). In brief, the RNA oligo (crRNA and tracrRNA) were resuspended in Nuclease-Free IDTE Buffer at final concentrations of 200 pM each. The two RNA oligos were mixed in equimolar concentrations to a final complex concentration of 44 pM. The complex then were heated at 95° C. for 5 min and then cooled down to room temperature (15-25° C.) on a bench top. The 36 pM Cas9 protein was pre-mixed slowly with the crRNA:tracrRNA complex and incubated at room temperature for 10-20 min before the transfection. Fresh crRNA: tracrRNA complexes were made for each experiment as per IDT recommendations.

EL4 cells with RNPs are transfected using Neon® Transfection System (ThermoFisher) at the following conditions: voltage (1380V), width (50 ms), pulses (1) 100 pl tip, buffer R (for RNPs)

Primary T cells with RNPs are transfected using Neon® Transfection System (ThermoFisher) at the following conditions: voltage (1550V), width (10 ms), pulses (3) 100 pl tip, buffer R (for RNPs)

CD45.2 Depletion Experiment:

$CD4^+$ T cells were isolated from C57BL6 (CD45.2) mice and C57BL6 congenic (CD45.1) mice using EasySep Mouse $CD4^+$ T Cell Isolation Kit (Stemm cell Technologies). RAG KO mice were reconstituted with 1:1 ration of $10 \times 10^6 CD45.2$ and CD45.1 donor $CD4^+$ T cells. Sarnes day as T cells transfer, mice also received intraperitoneal injections of PBS (non treated group) or a depleting a-CD4 Ab (clone GK1.5, 250 pg) for 3 consecutive days. CD45.2-ZAP immunotoxins were prepared by combining CD45.2 biotinylated antibody (160 kDa MW, Biolegend) with streptavidin-SAP conjugate (2.8 saporin molecules per streptavidin, 135 kDa MW, Advanced Targeting Systems) in a 1:1 molar ratio and subsequently diluted in PBS immediately before use, same as described in the initial publication: (https://www.ncbi.nlm.nih.gov/pmc/articles/PMC5179034/). In vivo administration of immunotoxin or the control with non-conjugated CD45.2 antibody was performed by intravenous injections. One week later, blood, peripheral lymph nodes (LN), mesenteric LN (mesLN) and spleen (SP) were collected and cells were stained with the following fluorochrome-conjugated mAbs: anti-CD45.2 (104), anti-CD45.1 (A20), anti-CD4 (RM4-5), anti-CD3 (145-2C11) all from Biolegend. Samples were acquired on a BD Fortessa (BD Biosciences) and analyzed with FlowJo software (Tree Star).

Experimental conditions FIG. 7. Blood from C57BL6/N Thy1.2+ (a), C57BL6 Thy1.1+/Thy1.2+ (b) or C57BL6 Thy1.1+ (c) mice was drawn and examined for expression of Thy1.2 (using mAb clone 53-2.1) and Thy1.1 (using mAb clone OX-7) by FACS. The FACS plots represent gating on total, lysed blood cells. Cells were acquired on BD Fortessa and analyzed with FlowJo software (Tree Star), d) shows an alignment of *Mus musculus* (C57BL6) genomic sequence of Thy1.2 and Thy1.1 isoforms. The two isoforms differ by a single nucleotide as indicated by the square.

Experimental conditions FIG. 8. EL.-4 cells were electroporated with a plasmid (px459) encoding a mammalian expression cassette for Cas9 and an antibiotic selection marker (puromycine) but without an sgRNA. After antibiotic selection cells were single cell sorted to establish subclones. The presence of Cas9 was verified by PCR on genomic DNA extracted from each sublonce. As a positive control genomic DNA from Cas9 transgenic mice was used (A). Cas9 functionality was tested by transfecting in vitro transcribed sgRNAs targeting CD45.2 and CD90.2. In all 6 tested clones cotransfection of both sgRNAs led to biallelic deletion of both genes in 48.3-61% of the cells (B).

Experimental conditions FIG. 13. CD4 cells from SM+ Ly5.1 were transfected with empty px458 plasmid, or plasmids containing sgRNA for IGOS and BCl6. GFP+ cells were sorted 48 h after initial activation step. SOK cells were IV injected in C57BL6 Ly5.2 recipients. 5 days post T cells transfer 15 C57BL6 recipients were IP injected with $2^*10^5$ PFU of Armstrong LCMV virus. 7 days post LCMV administration, mice were euthanized and LN, mesLN, SP were isolated and examined for TFH markers by FACS.

The invention claimed is:

1. A method for in vivo selective depletion of edited primary hematopoietic cells or non-edited primary hematopoietic cells in a subject in need thereof, said method comprising:
   (a) providing edited primary hematopoietic cells in which a genomic location has been edited to express a second isoform of a surface protein, which is different from a first isoform of said surface protein with regard to an amino acid marker, said first isoform being expressed in non-edited cells of the subject,
   (b) transferring said edited primary hematopoietic cells in said subject,
   (c) selectively depleting non-edited or edited primary hematopoietic cells carrying said first or second isoform of the surface protein, by use of an antibody or antibody-like molecule,
   wherein said non-edited or edited primary hematopoietic cells are depleted in said subject based on their expression of the first or second isoform of the surface protein.

2. The method of claim 1, wherein the first and second isoforms are functionally identical but can be distinguished by specific ligands.

3. The method of claim 1, wherein the first and second isoforms are native and engineered isoforms, respectively, and can be discriminated by two different ligands that specifically and selectively bind to the native and engineered isoform, respectively.

4. The method of claim 1, wherein the second isoform comprises an artificial mutation or a rare but naturally occurring mutation such as a single nucleotide polymorphism, engineered to change the antigenicity of the surface protein and provide an altered epitope.

5. The method of claim 2, wherein said specific ligands are antibodies that specifically and selectively bind to the first or second isoform or CARs that specifically and selectively bind to the first or second isoform.

6. The method of claim 2, wherein said second isoform is an engineered CD19 isoform altered from the native CD19 isoform with an altered epitope of CD19 native epitope.

7. The method of claim 2, wherein said second isoform is an engineered CD45 isoform altered from the native CD45 isoform with an altered epitope of CD45 native epitope.

* * * * *